US009051382B2

(12) United States Patent
Trentmann et al.

(10) Patent No.: US 9,051,382 B2
(45) Date of Patent: Jun. 9, 2015

(54) HUMAN NEUTROPHIL GELATINASE-ASSOCIATED LIPOCALIN (HNGAL) MUTEINS THAT BIND HEPCIDIN AND NUCLEIC ACID ENCODING SUCH

(75) Inventors: Stefan Trentmann, Allershausen (DE); Gabriele Matschiner, Munich (DE); Arne Skerra, Freising (DE); Andreas Hohlbaum, Paunzhausen (DE); Martin Huelsmeyer, Wolfersdorf (DE); Hendrik Gille, Munich (DE); Hans-Juergen Christian, Moosburg (DE); Kristian Jensen, Landshut (DE); Rachida Siham Bel Aiba, Munich (DE)

(73) Assignee: PIERIS AG, Freising-Wiehenstephan (DE)

( * ) Notice: Subject to any disclaimer, the term of this patent is extended or adjusted under 35 U.S.C. 154(b) by 117 days.

(21) Appl. No.: 13/816,808

(22) PCT Filed: Aug. 16, 2011

(86) PCT No.: PCT/EP2011/064086

§ 371 (c)(1), (2), (4) Date: May 24, 2013

(87) PCT Pub. No.: WO2012/022742

PCT Pub. Date: Feb. 23, 2012

(65) Prior Publication Data

US 2013/0244955 A1 Sep. 19, 2013

Related U.S. Application Data

(60) Provisional application No. 61/374,199, filed on Aug. 16, 2010.

(51) Int. Cl.

| | |
|---|---|
| ***C12P 21/06*** | (2006.01) |
| ***C07K 14/435*** | (2006.01) |
| ***A61K 38/16*** | (2006.01) |
| ***A61K 38/17*** | (2006.01) |
| ***C07H 21/04*** | (2006.01) |
| ***C07K 14/47*** | (2006.01) |
| ***C07K 16/26*** | (2006.01) |
| *C12N 15/09* | (2006.01) |
| *C12P 21/02* | (2006.01) |

(52) U.S. Cl.

CPC ............... *C07K 14/435* (2013.01); *C07K 14/47* (2013.01); *C07K 16/26* (2013.01); *C07K 2317/76* (2013.01); *C07K 2317/92* (2013.01); *C07K 2318/20* (2013.01)

(58) Field of Classification Search

None

See application file for complete search history.

(56) References Cited

U.S. PATENT DOCUMENTS

| | | | |
|---|---|---|---|
| 5,728,553 | A | 3/1998 | Goodey et al. |
| 6,177,074 | B1 | 1/2001 | Glue et al. |
| 6,403,564 | B1 | 6/2002 | Ganguly et al. |
| 6,500,930 | B2 | 12/2002 | Adamson |
| 6,620,413 | B1 | 9/2003 | De Sauvage et al. |
| 6,696,245 | B2 | 2/2004 | Winter et al. |
| 7,250,297 | B1 | 7/2007 | Beste et al. |
| 2003/0069395 | A1 | 4/2003 | Sato et al. |

FOREIGN PATENT DOCUMENTS

| | | | |
|---|---|---|---|
| EP | 0 330 451 | A2 | 8/1989 |
| EP | 0 361 991 | A2 | 4/1990 |
| WO | WO 99/16873 | A1 | 4/1999 |
| WO | WO 99/64016 | A1 | 12/1999 |
| WO | WO 00/75308 | A1 | 12/2000 |
| WO | WO 03/029462 | A1 | 4/2003 |
| WO | WO 03/029463 | A2 | 4/2003 |
| WO | WO 03/029471 | A1 | 4/2003 |
| WO | WO 2005/019254 | A1 | 3/2005 |
| WO | WO 2005/019255 | A1 | 3/2005 |
| WO | WO 2005/019256 | A2 | 3/2005 |
| WO | WO 2006/056464 | A2 | 6/2006 |
| WO | WO 2007/038619 | A2 | 4/2007 |
| WO | WO 2008/011158 | A2 | 1/2008 |
| WO | WO 2008/097461 | A2 | 8/2008 |
| WO | WO 2009/058797 | A1 | 5/2009 |
| WO | WO 2009/094551 | A1 | 7/2009 |
| WO | WO 2009/139822 | A1 | 11/2009 |
| WO | WO 2010/017070 | A1 | 2/2010 |

OTHER PUBLICATIONS

Wells, Biochemistry, 1990 vol. 29, pp. 8509-8517.*
Bork, Genome Research, 2000, vol. 10, pp. 398-400.*
Skolnick et al., Trends in Biotech, 2000, vol. 18, No. 1, pp. 34-39.*
Doerks et al., Trends in Genetics, 1998, vol. 14, pp. 248-250.*
Tokuriki and Tawflik, Current Opinion in Structural Biology, 2009, vol. 19, pp. 596-604.*
Hohlbaum et al, 53rd ASH Annual Meeting and Exposition Dec. 10-13, 2011.*
Wang et al. (Nuc. Acids Res, 1999, vol. 27, pp. 4609-4618.*
Kaufman et al Blood, 1999, vol. 94, pp. 3178-3184.*
Malyszko et al, Kidney Blood Press Research; 2010; vol. 33, pp. 157-165.*
Altschul et al., “Gapped BLAST and PSI-BLAST: a new generation of protein database search programs,” Nucl. Acids Res., 1997, 25(17):3389-3402.

(Continued)

*Primary Examiner* — Bridget E Bunner
*Assistant Examiner* — Fozia Hamud
(74) *Attorney, Agent, or Firm* — Foley & Lardner, LLP

(57) ABSTRACT

The present invention relates to novel, specific-binding therapeutic and/or diagnostic proteins directed against Hepcidin, which proteins preferably are muteins of a lipocalin protein. The invention also relates to nucleic acid molecules encoding such proteins and to methods for generation and use of such proteins and nucleic acid molecules. Accordingly, the invention also is directed to pharmaceutical and/or diagnostic compositions comprising such a lipocalin proteins, including uses of these proteins.

13 Claims, 18 Drawing Sheets

(56) References Cited

OTHER PUBLICATIONS

Altuvia et al., "Ranking Potential Binding Peptides to MHC Molecules by a Computational Threading Approach," J. Mol. Biol., 1995, 249:244-250.
Amstutz et al., "In vitro display technologies: novel developments and applications," Curr. Opin. Biotechnol., 2001, 12:400-405.
Bachmann, Barbara J., "Linkage Map of *Escherichia coli* K-12, Edition 8," Microbiol. Rev., Jun. 1990, 54(2):130-197.
Beste et al., "Small antibody-like proteins with prescribed ligand specificities derived from the lipocalin fold," Proc. Natl. Acad. Sci. USA, Mar. 1999, 96:1898-1903.
Bittker et al., "Nucleic acid evolution and minimization by nonhomologous random recombination," Nat. Biotechnol., Oct. 2002, 20:1024-1029.
Breustedt et al., "Comparative ligand-binding analysis of ten human lipocalins," Biochim. Biophys. Acta, 2006, 1764:161-173.
Bruckdorfer et al., "From Production of Peptides in Milligram Amounts for Research to Multi-Tons Quantities for Drugs of the Future," Curr. Pharm. Biotechnol., 2004, 5:29-43.
Bullock et al., "XL1-Blue: A High Efficiency Plasmid Transforming recA *Escherichia coli* Strain with Beta-Galactosidase Selection," Biotechniques, 1987, 5(4):376-378.
Dennis et al., "Albumin Binding as a General Strategy for Improving the Pharmacokinetics of Proteins," J. Biol. Chem., Sep. 20, 2002, 277(38):35035-35043.
Fling et al., "Peptide and Protein Molecular Weight Determination by Electrophoresis Using a High-Molarity Tris Buffer System without Urea," Anal. Biochem., 1986, 155:83-88.
Fuertges et al., :The Clinical Efficacy of Poly(Ethylene Glycol)-Modified Proteins,: J. Control. Release, 1990, 11:139-148.
Gaillard et al., "Targeted delivery across the blood-brain barrier," Expert Opin Drug Deliv., 2005, 2(2):299-309.
Gaillard et al., "Diphtheria toxin receptor-targeted brain drug delivery," International Congress Series., 2005, 1277:185-198.
Gebauer et al., "Engineered protein scaffolds as next-generation antibody therapeutics," Current Opinion in Chemical Biology, 2009, 13:245-255.
Goetz et al., "Ligand Preference Inferred from the Structure of Neutrophil Gelatinase Associated Lipocalin," Biochemistry, 2000, 39:1935-1941.
Holliger et al., "'Diabodies': Small bivalent and bispecific antibody fragments," PNAS USA, Jul. 1993, 90:6444-6448.
Ill et al., "Design and construction of a hybrid immunoglobulin domain with properties of both heavy and light chain variable regions," Protein Engineering, 1997, 10(8):949-957.
Kim et al., "High-Affinity Recognition of Lanthanide(III) Chelate Complexes by a Reprogrammed Human Lipocalin 2," J. Am. Chem. Soc., 2009, 131:3565-3576.
König et al., "Use of an albumin-binding domain for the selective immobilization of recombinant capture antibody fragments on ELISA plates," J. Immunol. Methods, 1998, 218:73-83.
Lowman, H.B. "Bacteriophage display and discovery of peptides leads for drug development," Annu. Rev. Biophys. Biomol. Struct., 1997, 26:401-424.
Malyszko et al., "Neutrophil Gelatinase-Associated Lipocalin and Hepcidin: What Do They Have in Common and Is There a Potential Interaction?," Kidney Blood Press Res., 2010, 33:157-165.
Martin et al., "The affinity-selection of a minibody polypeptide inhibitor of human interleukin-6," The EMBO Journal, 1994, 13(22):5303-5309.
Mateo et al., "Removal of Amphipathic Epitopes from Genetically Engineered Antibodies: Production of Modified Immunoglobulins with Reduced Immunogenicity," Hybridoma, 2000, 19(6):463-471.
Murakami et al., "Random insertion and deletion of arbitrary Number of bases for codon-based random mutation of DNAs," Nat. Biotechnol., Jan. 2002, 20:76-81.
Nemeth et al., "The N-terminus of hepcidin is essential for its interaction with ferroportin: structure-function study," Blood, Jan. 1, 2006, 107(1):328-333.
Osborn et al., "Pharmacokinetic and Pharmacodynamic Studies of a Human Serum Albumin-Interferon-α Fusion Protein in Cynomolgus Monkeys," J. Pharmacol. Exp. Ther., 2002, 303(2):540-548.
"Pieris Announces Preclinical In Vitro and In Vivo Data for its Anticalin® PRS-080 Hepcidin Antagonist Drug Program," Pieris AG: News and Events, May 23, 2001, XP002661794, retrieved from the Internet on Oct. 20, 2011, http://www.pieris-ag.com;news-events/2001-05-23-Pieris-Announces-Preclinical-In-Vitro-and-In-Vivo-Data.php, one page.
Pini et al., "Phage Display and Colony Filter Screening for High-Throughput Selection of Antibody Libraries," Comb. Chem. High Throughput Screen., 2002, 5:503-510.
Rodi et al., "Phage-display technology—finding a needle in a vast molecular haystack," Curr. Opin. Biotechnol., 1999, 10:87-93.
Sasu et al., "Antihepcidin antibody treatment modulates iron metabolism and is effective in a mouse model of inflammation-induced anemia," Blood, Apr. 29, 2010, 115(17):3616-3624.
Schiweck et al., "Fermenter Production of an Artificial Fab Fragment, Rationally Designed for the Antigen Cystatin, and Its Optimized Crystallization Through Constant Domain Shuffling," Proteins: Structure, Function and Genetics, 1995, 23:561-565.
Schlehuber et al., "A Novel Type of Receptor Protein, Based on the Lipocalin Scaffold, with Specificity for Digoxigenin," J. Mol. Biol., 2000, 297:1105-1120.
Schlehuber et al., "Duocalins, engineered ligand-binding proteins with dual specificity derived from the lipocalin fold," Biol. Chem., Sep. 2001, 382:1335-1342.
Schmidt et al., "Molecular Interaction Between the Strep-tag Affinity Peptide and its Cognate Target, Streptavidin," J. Mol. Biol., 1996, 255:753-766.
Schoenfeld et al., "An engineered lipocalin specific for CTLA-4 reveals a combining site with structural and conformational features similar to antibodies," PNAS, May 19, 2009, 106(20:8198-8203.
Silverman et al., "Multivalent avimer proteins evolved by exon shuffling of a family of human receptor domains," Nature Biotechnology, Dec. 2005, 23(12):1556-1561.
Skerra, Arne, "Use of the tetracycline promoter for the tightly regulated production of a murine antibody fragment in *Escherichia coli*," Gene, 1994, 151:131-135.
Skerra, Arne, "'Anticalins': a new class of engineered ligand-binding proteins with antibody-like properties," J. Biotechnol., 2001, 74:257-275.
Skerra, Arne, "Lipocalins as a scaffold," Biochimica et Biophysica Acta, 2000, 1482:337-350.
Skerra et al., "Use of the *Strep*-Tag and Streptavidin for Detection and Purification of Recombinant Proteins," Methods in Enzymology, 2000, vol. 326, pp. 271-304.
Studier et al., "Use of Bacteriophage T7 RNA Polymerase to Direct Selective High-level Expression of Cloned Genes," J. Mol. Biol., 1976, 189:113-130.
Traunecker et al., "Bispecific single chain molecules (Janusins) target cytotoxic lymphocytes on HIV infected cells," The EMBO Journal, 1991, 10(12):3655-3659.
Traunecker et al., "Janusin: New Molecular Design for Bispecific Reagents," Int. J. Cancer, 1992, Supplement 7, 51-52.
Vajo et al., "Genetically Engineered Insulin Analogs: Diabetes in the New Millenium," Pharmacol. Rev., 2000, 52(1):1-9.
Venturi et al., "High Level Production of Functional Antibody Fab Fragments in an Oxidizing Bacterial Cytoplasm," J. Mol. Biol., 2002, 315:1-8.
Vogt et al., "Bacterially produced apolipoprotein D binds progesterone and arachidonic acid, but not bilirubin or E-3M2H," Journal of Molecular Recognition, 2001, 14:79-86.
Wilson et al., "The use of mRNA display to select high-affinity protein-binding peptides," Proc. Natl. Acad. Sci. USA, Mar. 27, 2001, 98(7):3750-3755.
Yanisch-Perron et al., "Improved M13 phage cloning vectors and host strains: nucleotide sequences of the M13mp18 and pUC19 vectors," Gene, 1985, 33:103-119.
Zaccolo et al., "An Approach to Random Mutagenesis of DNA Using Mixtures of Triphosphate Derivatives of Nucleoside Analogues," J. Mol. Biol., 1996, 255:589-603.

* cited by examiner

```
                                                                 Bio-CCAGGACAACCAATTCCATGGGAAGTGGTATGTGGTAGGT (SEQ ID NO:24)
CCCAGGACTCCACCTCAGACC (SEQ ID NO:32)
                                                                                        GAAGTGGTATGTGGTAGGTNNKGCAGGGAATNNKNNKCTC
CAGGACTCCACCTCAGACCTGATCCCAGCCCCACCTCTGAGCAAGGTCCCTCTGCAGCAGAACTTCCAGGACAACCAATTCCAtGGGAAGTGGTATGTGGTAGGTCTCGCAGGGAATGCAATTCTC
+---------+---------+---------+---------+---------+---------+---------+---------+---------+---------+---------+---------+------
GTCCTGAGGTGGAGTCTGGACTAGGGTCGGGGTGGAGACTCGTTCCAGGGAGACGTCGTCTTGAAGGTCCTGTTGGTTAAGGTACCCTTCACCATACACCATCCAGAGCGTCCCTTACGTTAAGAG

GlnAspSerThrSerAspLeuIleProAlaProProLeuSerLysValProLeuGlnGlnAsnPheGlnAspAsnGlnPheHisGlyLysTrpTyrValValGlyLeuAlaGlyAsnAlaIleLeu
 1                          10                            20                         28    30                    36               40 41

                                                   (SEQ ID NO:16)
AGAGAAGACAAAGACCCGNNKAAGATGNNKGCCACCATCTATGAGCTG          CAAGAGCTACAATGTCACANNKGTCNNKTTTNNKNNKAAGAAGTGTNNKTACNNKATCNNKACTTTTGTT
AGAGAAGACAAAGACCCGCAAAAGATGTATGCCACCATCTATGAGCTGAAAGAAGACAAGAGCTACAATGTCACCTCCGTCCTGTTTAGGAAAAAGAAGTGTGACTACTGGATCAGGACTTTTGTT
----+---------+---------+---------+---------+---------+---------+---------+---------+---------+---------+---------+---------+-
TCTCTTCTGTTTCTGGGCGTTTTCTACATACGGTGGTAGATACTCGACTTTCTTCTGTTCTCGATGTTACAGTGGAGGCAGGACAAATCCTTTTTCTTCACACTGATGACCTAGTCCTGAAAACAA
                                        CGGTGGTAGATACTCGACTTTCTTCTATTCTCGATGTTACAGTGG (SEQ ID NO:40)                       TGAAAACAA
ArgGluAspLysAspProGlnLysMetTyrAlaThrIleTyrGluLeuLysGluAspLysSerTyrAsnValThrSerValLeuPheArgLysLysLysCysAspTyrTrpIleArgThrPheVal
                  49 50     52                     60                         68    70   72 73          77    79 80 81

(SEQ ID NO:39)
CCAGGTTCC        GGCGAGTTCACGCTGGGCNNKATTAAGAGTNNKCCTGGANNKACGAGTNNKCTCGTCCGAGTGGTGAG (SEQ ID NO:18)        GCTATGGTGTTCTTCAAGNNKGTT
CCAGGTTcCCAGCCAGGCGAGTTCACGCTGGGCAACATTAAGAGTTACCCTGGATTAACGAGTTACCTCGTCCGAGTGGTGAGCACCAACTACAACCAGCATGCTATGGTGTTCTTCAAGAAAGTT
--------+---------+---------+---------+---------+---------+---------+---------+---------+---------+---------+---------+-------
GGTCCAAGGGTCGGTCCGCTCAAGTGCGACCCGTTGTAATTCTCAATGGGACCTAATTGCTCAATGGAGCAGGCTCACCACTCGTGGTTGATGTTGGTCGTACGATACCACAAGAAGTTCTTTCAA
GGTCCAAGGGTCGGTCCGCTCAAGTGCGACCCG (SEQ ID NO:21)                  GAGCAGGCTCACCACTCGTGGTTGATGTTGGTCGTACGATACCACAAGAAGTTC (SEQ ID NO:22)
ProGlySerGlnProGlyGluPheThrLeuGlyAsnIleLysSerTyrProGlyLeuThrSerTyrLeuValArgValValSerThrAsnTyrAsnGlnHisAlaMetValPhePheLysLysVal
     87       90                96         100      103      106      110                                   120          125

NNKCAAAACAGGGAGNNKTTCNNKATCACCCTCTACGGGAGAAC (SEQ ID NO:19)
TCTCAAAACAGGGAGTACTTCAAGATCACCCTCTACGGGAGAACCAAGGAGCTGACTTCGGAACTAAAGGAGAACTTCATCCGCTTCTCCAAATCTCTGGGCCTCCCTGAAAACCACATCGTCTTC
--+---------+---------+---------+---------+---------+---------+---------+---------+---------+---------+---------+---------+---
AGAGTTTTGTCCCTCATGAAGTTCTAGTGGGAGATGCCCTCTTGGTTCCTCGACCGAAGCCTTGATTTCCTCTTGAAGTAGGCGAAGAGGTTTAGAGACCCGGAGGGACTTTTGGTGTAGCAGAAG
                              GTGGGAGATGCCCTCTTGGTTCCTCGACCGAAGCCTTGATTTCCTCTTGAAGTAGGCGAAGAGG (SEQ ID NO:41)
                                                                          CTTGAAGTAGGCGAAGAGGTTTAGAGACCCGGAGGGACTT-Bio (SEQ ID NO:25)
SerGlnAsnArgGluTyrPheLysIleThrLeuTyrGlyArgThrLysGluLeuThrSerGluLeuLysGluAsnPheIleArgPheSerLysSerLeuGlyLeuProGluAsnHisIleValPhe
127      130  132   134               140                              150                                 160

CCTGTCCCAATCGACCAGTGTATCGACGGCAGCGCTTGGTCCCACCCGCAGTTCGAAAAATAA (SEQ ID NO:42)
------+---------+---------+---------+---------+---------+------
GGACAGGGTTAGCTGGTCACATAGCTGCCGTCGCGAACCAGGGTGGGCGTCAAGCTTTTTATT (SEQ ID NO:44)
                              TGCCGTCGCGAACCAGGGTGGGCGTCA (SEQ ID NO:33)
ProValProIleAspGlnCysIleAspGlySerAlaTrpSerHisProGlnPheGluLysEnd (SEQ ID NO:43)
   170                           180     Strep-tagII     188
```

Fig. 1

```
  1 CCAATTCCATGGGAAATGGTATGTCGTGGGCnnnGCCGGAAATnnnnnnCTGCGTGAGGATAAGGATCCGnnnAAAATGnnnGCGACCAT 90
    +---------+---------+---------+---------+---------+---------+---------+---------+---------
    GGTTAAGGTACCCTTTACCATACAGCACCCGGACCGGCCTTTACGGTAAGACGCACTCCTATTCCTAGGCGTCTTTTACATACGCTGGTA
     GlnPheHisGlyLysTrpTyrValValGlyXaaAlaGlyAsnXaaXaaLeuArgGluAspLysAspProXaaLysMetXaaAlaThrIle
                                 8           12 13                        21        24

 91 TTACGAGTTGAAAGAAGATAAATCATATAACGTCACCnnnGTGnnnTTTnnnnnnAAGAAATGCnnnTACnnnATTnnnACCTTTGTGCC 180
    +---------+---------+---------+---------+---------+---------+---------+---------+---------
    AATGCTCAACTTTCTTCTATTTAGTATATTGCAGTGGAGGCACAACAAAGCGTTTTTCTTTACGCTGATGACCTAAGCATGGAAACACGG
     TyrGluLeuLysGluAspLysSerTyrAsnValThrXaaValXaaPheXaaXaaLysLysCysXaaTyrXaaIleXaaThrPheValPro
                                       40     42     44 45          49     51     53

181 GGGGAGCCAGCCGGGCGAGTTTACTTTAGGCnnnATTAAAAGTnnnCCGGGCnnnACATCAnnnTTGGTCCGCGTCGTGAGCACCAACTA 270
    +---------+---------+---------+---------+---------+---------+---------+---------+---------
    CCCCTCGGTCGGCCCGCTCAAATGAAATCCGTTGTAATTTTCAATGGGCCCGGACTGTAGTATGAACCAGGCGCAGCACTCGTGGTTGAT
     GlySerGlnProGlyGluPheThrLeuGlyXaaIleLysSerXaaProGlyXaaThrSerXaaLeuValArgValValSerThrAsnTyr
                                68           72         75         78

271 CAACCAGCATGCCATGGTGTTCTTCAAGnnnGTGnnnCAGAACCGCGAGnnnTTTnnnATCACACTGTACGGGCGCACGAAAGAACTGAC 360
    +---------+---------+---------+---------+---------+---------+---------+---------+---------
    GTTGGTCGTACGGTACCACAAGAAGTTCTTTCACAGGGTCTTGGCGCTCATGAAATTCTAGTGTGACATGCCCGCGTGCTTTCTTGACTG
     AsnGlnHisAlaMetValPhePheLysXaaValXaaGlnAsnArgGluXaaPheXaaIleThrLeuTyrGlyArgThrLysGluLeuThr
                              97     99               104    106

361 AAGCGAGCTGAAGGAAAATTTTATCCGCTTTTCCAAATCTCTGG 404 (SEQ ID NO:45)
    +---------+---------+---------+---------+---
    TTCGCTCGACTTCCTTTTAAAATAGGCGAAAAGGTTTAGAGACC (SEQ ID NO: 47)
     SerGluLeuLysGluAsnPheIleArgPheSerLysSerLeu  (SEQ ID NO: 46)
```

| | 1 | 2 | 3 | 4 | 5 | 6 | 7 | 8 | 9 | 10 | 11 | 12 |
|---|---|---|---|---|---|---|---|---|---|---|---|---|
| phNGAL98 | Q | D | S | T | S | D | L | I | P | A | P | P |
| (phNGAL98) | Gln | Asp | Ser | Thr | Ser | Asp | Leu | Ile | Pro | Ala | Pro | Pro |
| SEQ ID NO:2 | Q | D | S | T | S | D | L | I | P | A | P | P |
| SEQ ID NO:3 | Q | D | S | T | S | D | L | I | P | A | P | P |
| SEQ ID NO:4 | Q | D | S | T | S | D | L | I | P | A | P | P |
| SEQ ID NO:5 | Q | D | S | T | S | D | L | I | P | A | P | P |
| SEQ ID NO:1 | Q | D | S | T | S | D | L | I | P | A | P | P |
| SEQ ID NO:6 | Q | D | S | T | S | D | L | I | P | A | P | P |
| SEQ ID NO:7 | Q | D | S | T | S | D | L | I | P | A | P | P |
| SEQ ID NO:14 | Q | D | S | T | S | D | L | I | P | A | P | P |

| | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|
| phNGAL98 | L | S | K | V | P | L | Q | Q | N | F | Q | D | N | Q | F | H | G | K |
| (phNGAL98) | Leu | Ser | Lys | Val | Pro | Leu | Gln | Gln | Asn | Phe | Gln | Asp | Asn | Gln | Phe | His | Gly | Lys |
| SEQ ID NO:2 | L | S | K | V | P | L | Q | Q | N | F | Q | D | N | Q | F | H | G | K |
| SEQ ID NO:3 | L | S | K | V | P | L | Q | Q | N | F | Q | D | N | Q | F | H | G | K |
| SEQ ID NO:4 | L | S | K | V | P | L | Q | Q | N | F | Q | D | N | Q | F | H | G | K |
| SEQ ID NO:5 | L | S | K | V | P | L | Q | Q | N | F | Q | D | N | Q | F | H | G | K |
| SEQ ID NO:1 | L | S | K | V | P | L | Q | Q | N | F | Q | D | N | Q | F | H | G | K |
| SEQ ID NO:6 | L | S | K | V | P | L | Q | Q | N | F | Q | D | N | Q | F | H | G | K |
| SEQ ID NO:7 | L | S | K | V | P | L | Q | Q | N | F | Q | D | N | Q | F | H | G | K |
| SEQ ID NO:14 | L | S | K | V | P | L | Q | Q | N | F | Q | D | N | Q | F | H | G | K |

| | 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|---|
| | | | | | | * | | | | * | * | | | | | | |
| phNGAL98 | W | Y | V | V | G | L | A | G | N | A | I | L | R | E | D | K | D |
| (phNGAL98) | Trp | Tyr | Val | Val | Gly | Leu | Ala | Gly | Asn | Ala | Ile | Leu | Arg | Glu | Asp | Lys | Asp |
| SEQ ID NO:2 | W | Y | V | V | G | T | A | G | N | S | I | L | R | E | D | K | D |
| SEQ ID NO:3 | W | Y | V | V | G | V | A | G | N | G | L | L | R | E | D | K | D |
| SEQ ID NO:4 | W | Y | V | V | G | V | A | G | N | E | M | L | R | E | D | K | D |
| SEQ ID NO:5 | W | Y | V | V | G | A | A | G | N | S | L | L | R | E | D | K | D |
| SEQ ID NO:1 | W | Y | V | V | G | L | A | G | N | E | V | L | R | E | D | K | D |
| SEQ ID NO:6 | W | Y | V | V | G | L | A | G | N | E | I | L | R | E | D | K | D |
| SEQ ID NO:7 | W | Y | V | V | G | L | A | G | N | R | V | L | R | E | D | K | D |
| SEQ ID NO:14 | W | Y | V | V | G | L | A | G | N | E | V | L | R | E | D | K | D |

| | 48 | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|---|
| | | * | | | * | | | | | | | | | | | | |
| phNGAL98 | P | Q | K | M | Y | A | T | I | Y | E | L | K | E | D | K | S | Y |
| (phNGAL98) | Pro | Gln | Lys | Met | Tyr | Ala | Thr | Ile | Tyr | Glu | Leu | Lys | Glu | Asp | Lys | Ser | Tyr |
| SEQ ID NO:2 | P | Q | K | M | W | A | T | I | Y | E | L | K | E | D | K | S | Y |
| SEQ ID NO:3 | P | L | K | M | H | A | T | I | Y | E | L | K | E | D | K | S | Y |
| SEQ ID NO:4 | P | L | K | M | L | A | T | I | Y | E | L | K | E | D | K | S | Y |
| SEQ ID NO:5 | P | M | K | M | W | A | T | I | Y | E | L | K | E | D | K | S | Y |
| SEQ ID NO:1 | P | M | K | M | W | A | T | I | Y | E | L | E | E | D | K | S | Y |
| SEQ ID NO:6 | P | L | K | M | W | A | T | I | Y | E | L | K | E | D | K | S | Y |
| SEQ ID NO:7 | P | Q | K | M | F | A | T | I | Y | E | L | K | E | D | K | S | Y |
| SEQ ID NO:14 | P | M | K | M | W | A | T | I | Y | E | L | E | E | D | K | S | Y |

FIG. 3B

| | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|
| | | | | * | | * | | * | * | | | | * | | * | | * |
| phNGAL98 | N | V | T | S | V | L | F | R | K | K | K | C | D | Y | W | I | R |
| (phNGAL98) | Asn | Val | Thr | Ser | Val | Leu | Phe | Arg | Lys | Lys | Lys | Cys | Asp | Tyr | Trp | Ile | Arg |
| SEQ ID NO:2 | N | V | T | R | V | F | F | E | G | K | K | C | R | Y | V | I | E |
| SEQ ID NO:3 | N | V | T | R | V | L | F | V | R | K | K | C | R | Y | Y | I | S |
| SEQ ID NO:4 | N | V | T | R | V | M | F | E | Y | K | K | C | V | Y | L | I | E |
| SEQ ID NO:5 | N | V | T | R | V | N | F | G | G | K | K | C | S | Y | L | I | E |
| SEQ ID NO:1 | N | V | T | I | V | M | F | L | A | K | K | C | E | Y | L | F | Q |
| SEQ ID NO:6 | N | V | T | R | V | Q | F | G | E | K | K | C | G | Y | G | I | E |
| SEQ ID NO:7 | N | V | T | G | V | D | F | R | T | K | K | C | L | Y | S | I | G |
| SEQ ID NO:14 | N | V | T | I | V | M | F | L | A | K | K | C | E | Y | L | F | Q |

| | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|
| | | | | | | | | | | | | | | | * | | | | * |
| phNGAL98 | T | F | V | P | G | S | Q | P | G | E | F | T | L | G | N | I | K | S | Y |
| (phNGAL98) | Thr | Phe | Val | Pro | Gly | Ser | Gln | Pro | Gly | Glu | Phe | Thr | Leu | Gly | Asn | Ile | Lys | Ser | Tyr |
| SEQ ID NO:2 | T | F | V | P | G | S | Q | P | G | E | F | T | L | G | K | I | K | S | A |
| SEQ ID NO:3 | T | F | V | P | G | S | Q | P | G | E | F | T | L | G | R | I | K | S | E |
| SEQ ID NO:4 | T | F | V | P | G | S | Q | P | G | E | F | T | L | G | T | I | K | S | V |
| SEQ ID NO:5 | T | F | V | P | G | S | Q | P | G | E | F | T | L | G | S | I | K | S | R |
| SEQ ID NO:1 | T | F | V | P | G | S | Q | P | G | E | F | T | L | G | D | I | K | S | S |
| SEQ ID NO:6 | T | F | V | P | G | S | Q | P | G | E | F | T | L | G | S | I | K | S | V |
| SEQ ID NO:7 | T | F | V | P | G | S | Q | P | G | E | F | T | L | G | V | I | K | S | Q |
| SEQ ID NO:14 | T | F | V | P | G | C | Q | P | G | E | F | T | L | G | D | I | K | S | S |

| | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|
| | | | * | | | * | | | | | | | | | |
| phNGAL98 | P | G | L | T | S | Y | L | V | R | V | V | S | T | N | Y |
| (phNGAL98) | Pro | Gly | Leu | Thr | Ser | Tyr | Leu | Val | Arg | Val | Val | Ser | Thr | Asn | Tyr |
| SEQ ID NO:2 | P | G | G | T | S | I | L | V | R | V | V | S | T | N | Y |
| SEQ ID NO:3 | P | G | R | T | S | F | L | V | R | V | V | S | T | N | Y |
| SEQ ID NO:4 | P | G | L | T | S | G | L | V | R | V | V | S | T | N | Y |
| SEQ ID NO:5 | P | G | A | T | S | V | L | V | R | V | V | S | T | N | Y |
| SEQ ID NO:1 | P | G | R | T | S | G | L | V | R | V | V | S | T | N | Y |
| SEQ ID NO:6 | P | G | G | T | S | R | L | V | R | V | V | S | T | N | Y |
| SEQ ID NO:7 | P | G | W | T | S | Y | L | V | R | V | V | S | T | N | Y |
| SEQ ID NO:14 | P | G | R | T | S | G | L | V | R | V | V | S | T | N | Y |

FIG. 3C

| | | | | | | | | | | * | | * | | | |
|---|---|---|---|---|---|---|---|---|---|---|---|---|---|---|---|
| | 116 | 117 | 118 | 119 | 120 | 121 | 122 | 123 | 124 | 125 | 126 | 127 | 128 | 129 | 130 |
| phNGAL98 | N | Q | H | A | M | V | F | F | K | K | V | S | Q | N | R |
| (phNGAL98) | Asn | Gln | His | Ala | Met | Val | Phe | Phe | Lys | Lys | Val | Ser | Gln | Asn | Arg |
| SEQ ID NO:2 | N | Q | H | A | M | V | F | F | K | V | V | W | Q | N | R |
| SEQ ID NO:3 | N | Q | H | A | M | V | F | F | K | M | V | W | Q | N | R |
| SEQ ID NO:4 | N | Q | H | A | M | V | F | F | K | R | V | W | Q | N | R |
| SEQ ID NO:5 | N | Q | H | A | M | V | F | F | K | L | V | T | Q | N | R |
| SEQ ID NO:1 | N | Q | H | A | M | V | F | F | K | T | V | W | Q | N | R |
| SEQ ID NO:6 | N | Q | H | A | M | V | F | F | K | F | V | W | Q | N | R |
| SEQ ID NO:7 | N | Q | H | A | M | V | F | F | K | T | V | W | Q | N | R |
| SEQ ID NO:14 | N | Q | H | A | M | V | F | F | K | T | V | W | Q | N | R |

| | | * | | * | | | | | | | | | | | | |
|---|---|---|---|---|---|---|---|---|---|---|---|---|---|---|---|---|
| | 131 | 132 | 133 | 134 | 135 | 136 | 137 | 138 | 139 | 140 | 141 | 142 | 143 | 144 | 145 | 146 |
| phNGAL98 | E | Y | F | K | I | T | L | Y | G | R | T | K | E | L | T | S |
| (phNGAL98) | Glu | Tyr | Phe | Lys | Ile | Thr | Leu | Tyr | Gly | Arg | Thr | Lys | Glu | Leu | Thr | Ser |
| SEQ ID NO:2 | E | L | F | W | I | T | L | Y | G | R | T | K | E | L | T | S |
| SEQ ID NO:3 | E | V | F | W | I | T | L | Y | G | R | T | K | E | L | T | S |
| SEQ ID NO:4 | E | V | F | W | I | T | L | Y | G | R | T | K | E | L | T | S |
| SEQ ID NO:5 | E | V | F | W | I | T | L | Y | G | R | T | K | E | L | T | S |
| SEQ ID NO:1 | E | V | F | W | I | T | L | Y | G | R | T | K | E | L | T | S |
| SEQ ID NO:6 | E | V | F | W | I | T | L | Y | G | R | T | K | E | L | T | S |
| SEQ ID NO:7 | E | V | F | W | I | T | L | Y | G | R | T | K | E | L | T | S |
| SEQ ID NO:14 | E | V | F | W | I | T | L | Y | G | R | T | K | E | L | T | S |

| | 147 | 148 | 149 | 150 | 151 | 152 | 153 | 154 | 155 | 156 | 157 | 158 | 159 | 160 | 161 | 162 | 163 |
|---|---|---|---|---|---|---|---|---|---|---|---|---|---|---|---|---|---|
| phNGAL98 | E | L | K | E | N | F | I | R | F | S | K | S | L | G | L | P | E |
| (phNGAL98) | Glu | Leu | Lys | Glu | Asn | Phe | Ile | Arg | Phe | Ser | Lys | Ser | Leu | Gly | Leu | Pro | Glu |
| SEQ ID NO:2 | E | L | K | E | N | F | I | R | F | S | K | S | L | G | L | P | E |
| SEQ ID NO:3 | E | L | K | E | N | F | I | R | F | S | K | S | L | G | L | P | E |
| SEQ ID NO:4 | E | L | K | E | N | F | I | R | F | S | K | S | L | G | L | P | E |
| SEQ ID NO:5 | E | L | K | E | N | F | I | R | F | S | K | S | L | G | L | P | E |
| SEQ ID NO:1 | E | L | K | E | N | F | I | R | F | S | K | S | L | G | L | P | E |
| SEQ ID NO:6 | E | L | K | E | N | F | I | R | F | S | K | S | L | G | L | P | E |
| SEQ ID NO:7 | E | L | K | E | N | F | I | R | F | S | K | S | L | G | L | P | E |
| SEQ ID NO:14 | E | L | K | E | N | F | I | R | F | S | K | S | L | G | L | P | E |

FIG. 3D

| | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|
| phNGAL98 | N | H | I | V | F | P | V | P | I | D | Q | C | I | D | G |
| (phNGAL98) | Asn | His | Ile | Val | Phe | Pro | Val | Pro | Ile | Asp | Gln | Cys | Ile | Asp | Gly |
| SEQ ID NO:2 | N | H | I | V | F | P | V | P | I | D | Q | C | I | D | G |
| SEQ ID NO:3 | N | H | I | V | F | P | V | P | I | D | Q | C | I | D | G |
| SEQ ID NO:4 | N | H | I | V | F | P | V | P | I | D | Q | C | I | D | G |
| SEQ ID NO:5 | N | H | I | V | F | P | V | P | I | D | Q | C | I | D | G |
| SEQ ID NO:1 | N | H | I | V | F | P | V | P | I | D | Q | C | I | D | G |
| SEQ ID NO:6 | N | H | I | V | F | P | V | P | I | D | Q | C | I | D | G |
| SEQ ID NO:7 | N | H | I | V | F | P | V | P | I | D | Q | C | I | D | G |
| SEQ ID NO:14 | N | H | I | V | F | P | V | P | I | D | Q | C | I | D | G |

| | 179 | 180 | 181 | 182 | 183 | 184 | 185 | 186 |
|---|---|---|---|---|---|---|---|---|
| phNGAL98 | S | A | W | S | H | P | Q | F |
| (phNGAL98) | Ser | Ala | Trp | Ser | His | Pro | Gln | Phe |
| SEQ ID NO:2 | S | A | W | S | H | P | Q | F |
| SEQ ID NO:3 | S | A | W | S | H | P | Q | F |
| SEQ ID NO:4 | S | A | W | S | H | P | Q | F |
| SEQ ID NO:5 | S | A | W | S | H | P | Q | F |
| SEQ ID NO:1 | S | A | W | S | H | P | Q | F |
| SEQ ID NO:6 | S | A | W | S | H | P | Q | F |
| SEQ ID NO:7 | S | A | W | S | H | P | Q | F |
| SEQ ID NO:14 | S | A | W | S | H | P | Q | F |

FIG. 3E

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| phNGAL98 | Q | D | S | T | S | D | L | I | P | A | P | P | L | S | K | V |
| SEQ ID NO:1 | Q | D | S | T | S | D | L | I | P | A | P | P | L | S | K | V |
| | | | | | | | | | | | | | | | | |
| SEQ ID NO:8 | Q | D | S | T | S | D | L | I | P | A | P | P | L | S | K | V |
| SEQ ID NO:9 | Q | D | S | T | S | D | L | I | P | A | P | P | L | S | K | V |
| SEQ ID NO:10 | Q | D | S | T | S | D | L | I | P | A | P | P | L | S | K | V |
| SEQ ID NO:11 | Q | D | S | T | S | D | L | I | P | A | P | P | L | S | K | V |
| SEQ ID NO:12 | Q | D | S | T | S | D | L | I | P | A | P | P | L | S | K | V |
| SEQ ID NO:13 | Q | D | S | T | S | D | L | I | P | A | P | P | L | S | K | V |

FIG. 3F

| | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|
| phNGAL98 | P | L | Q | Q | N | F | Q | D | N | Q | F | H | G | K | W | Y | V |
| SEQ ID NO: 1 | P | L | Q | Q | N | F | Q | D | N | Q | F | H | G | K | W | Y | V |
| SEQ ID NO: 8 | P | L | Q | Q | N | F | Q | D | N | Q | F | H | G | K | W | Y | V |
| SEQ ID NO: 9 | P | L | Q | Q | N | F | Q | D | N | Q | F | H | G | K | W | Y | V |
| SEQ ID NO: 10 | P | L | Q | Q | N | F | Q | D | N | Q | F | H | G | K | W | Y | V |
| SEQ ID NO: 11 | P | L | Q | Q | N | F | Q | D | N | Q | F | H | G | K | W | Y | V |
| SEQ ID NO: 12 | P | L | Q | Q | N | F | Q | D | N | Q | F | H | G | K | W | Y | V |
| SEQ ID NO: 13 | P | L | Q | Q | N | F | Q | D | N | Q | F | H | G | K | W | Y | V |

| | | | * | | | | * | * | | | | | | | | * | |
|---|---|---|---|---|---|---|---|---|---|---|---|---|---|---|---|---|---|
| | 34 | 35 | 36 | 37 | 38 | 39 | 40 | 41 | 42 | 43 | 44 | 45 | 46 | 47 | 48 | 49 | 50 |
| phNGAL98 | V | G | L | A | G | N | A | I | L | R | E | D | K | D | P | Q | K |
| SEQ ID NO: 1 | V | G | L | A | G | N | E | V | L | R | E | D | K | D | P | M | K |
| SEQ ID NO: 8 | V | G | L | A | G | N | E | V | L | R | E | D | K | D | P | M | K |
| SEQ ID NO: 9 | V | G | L | A | G | N | E | V | L | R | E | D | K | D | P | M | K |
| SEQ ID NO: 10 | V | G | L | A | G | N | E | I | L | R | E | D | K | D | P | M | K |
| SEQ ID NO: 11 | V | G | L | A | G | N | E | I | L | R | E | D | K | D | P | M | K |
| SEQ ID NO: 12 | V | G | L | A | G | N | E | V | L | R | E | D | K | D | P | M | K |
| SEQ ID NO: 13 | V | G | L | A | G | N | E | V | L | R | E | D | K | D | P | M | K |

| | | * | | | | | | | | | | | | | | | |
|---|---|---|---|---|---|---|---|---|---|---|---|---|---|---|---|---|---|
| | 51 | 52 | 53 | 54 | 55 | 56 | 57 | 58 | 59 | 60 | 61 | 62 | 63 | 64 | 65 | 66 | 67 |
| phNGAL98 | M | Y | A | T | I | Y | E | L | K | E | D | K | S | Y | N | V | T |
| SEQ ID NO: 1 | M | W | A | T | I | Y | E | L | E | E | D | K | S | Y | N | V | T |
| SEQ ID NO: 8 | M | W | A | T | I | Y | E | L | E | E | D | K | S | Y | N | V | T |
| SEQ ID NO: 9 | M | W | A | T | I | Y | E | L | E | E | D | K | S | Y | N | V | T |
| SEQ ID NO: 10 | M | W | A | T | I | Y | E | L | E | E | D | R | S | Y | N | V | T |
| SEQ ID NO: 11 | M | W | A | T | I | Y | E | L | E | E | D | K | S | Y | N | V | T |
| SEQ ID NO: 12 | M | W | A | T | I | Y | E | L | E | E | D | K | S | Y | N | V | T |
| SEQ ID NO: 13 | M | W | A | T | I | Y | E | L | E | E | D | K | S | Y | N | V | T |

| | * | | * | | * | * | | | | * | | * | | * | | | | |
|---|---|---|---|---|---|---|---|---|---|---|---|---|---|---|---|---|---|---|
| | 68 | 69 | 70 | 71 | 72 | 73 | 74 | 75 | 76 | 77 | 78 | 79 | 80 | 81 | 82 | 83 | 84 | 85 |
| phNGAL98 | S | V | L | F | R | K | K | K | C | D | Y | W | I | R | T | F | V | P |
| SEQ ID NO: 1 | I | V | M | F | L | A | K | K | C | E | Y | L | F | Q | T | F | V | P |
| SEQ ID NO: 8 | I | V | M | P | L | A | E | K | C | E | Y | L | F | Q | T | F | V | P |
| SEQ ID NO: 9 | I | V | M | S | L | A | K | K | C | E | Y | L | F | Q | T | F | V | P |
| SEQ ID NO: 10 | I | V | M | F | L | A | K | K | C | E | Y | L | F | Q | T | F | V | P |
| SEQ ID NO: 11 | I | V | M | F | L | A | K | K | C | E | Y | L | F | Q | T | F | V | P |
| SEQ ID NO: 12 | I | V | M | F | L | A | E | E | C | E | Y | L | F | Q | T | F | V | P |
| SEQ ID NO: 13 | I | V | M | P | L | A | E | K | C | E | Y | L | F | Q | T | F | V | P |

FIG. 3G

| | 86 | 87 | 88 | 89 | 90 | 91 | 92 | 93 | 94 | 95 | 96 | 97 | 98 | 99 | 100 | 101 | 102 | 103 |
|---|---|---|---|---|---|---|---|---|---|---|---|---|---|---|---|---|---|---|
| | | | | | | | | | | | * | | | | * | | | * |
| phNGAL98 | G | S | Q | P | G | E | F | T | L | G | N | I | K | S | Y | P | G | L |
| SEQ ID NO:1 | G | S | Q | P | G | E | F | T | L | G | D | I | K | S | S | P | G | R |
| SEQ ID NO:8 | G | S | Q | P | G | E | F | T | L | G | G | I | K | S | G | P | G | R |
| SEQ ID NO:9 | G | S | Q | P | G | E | F | T | L | G | D | I | K | S | S | P | G | R |
| SEQ ID NO:10 | G | S | Q | P | G | E | F | T | L | G | D | I | K | S | S | P | G | R |
| SEQ ID NO:11 | G | S | Q | P | G | E | F | T | L | G | D | I | K | S | S | P | G | R |
| SEQ ID NO:12 | G | S | Q | P | G | E | F | T | L | G | D | I | K | S | S | P | G | R |
| SEQ ID NO:13 | G | C | Q | P | G | E | F | T | L | G | G | I | K | S | G | P | G | R |

| | 104 | 105 | 106 | 107 | 108 | 109 | 110 | 111 | 112 | 113 | 114 | 115 | 116 | 117 | 118 |
|---|---|---|---|---|---|---|---|---|---|---|---|---|---|---|---|
| | | | * | | | | | | | | | | | | |
| phNGAL98 | T | S | Y | L | V | R | V | V | S | T | N | Y | N | Q | H |
| SEQ ID NO:1 | T | S | G | L | V | R | V | V | S | T | N | Y | N | Q | H |
| SEQ ID NO:8 | T | S | G | L | V | R | V | V | S | T | N | Y | N | Q | H |
| SEQ ID NO:9 | T | S | G | L | V | R | V | V | S | T | N | Y | N | Q | H |
| SEQ ID NO:10 | T | S | G | L | V | R | V | V | S | T | N | Y | N | Q | H |
| SEQ ID NO:11 | T | S | G | L | V | R | V | V | S | T | N | Y | N | Q | H |
| SEQ ID NO:12 | T | S | G | L | V | R | V | V | S | T | N | Y | N | Q | H |
| SEQ ID NO:13 | T | S | G | L | V | R | V | V | S | T | N | Y | N | Q | H |

| | 119 | 120 | 121 | 122 | 123 | 124 | 125 | 126 | 127 | 128 | 129 | 130 | 131 | 132 | 133 |
|---|---|---|---|---|---|---|---|---|---|---|---|---|---|---|---|
| | | | | | | | * | | * | | | | | * | |
| phNGAL98 | A | M | V | F | F | K | K | V | S | Q | N | R | E | Y | F |
| SEQ ID NO:1 | A | M | V | F | F | K | T | V | W | Q | N | R | E | V | F |
| SEQ ID NO:8 | A | M | V | F | F | K | V | V | W | Q | N | R | E | V | F |
| SEQ ID NO:9 | A | M | V | F | F | K | V | V | W | Q | N | R | E | V | F |
| SEQ ID NO:10 | A | M | V | F | F | K | V | V | W | Q | N | R | E | V | F |
| SEQ ID NO:11 | A | M | V | F | F | K | V | V | W | Q | N | R | E | V | F |
| SEQ ID NO:12 | A | M | V | F | F | K | V | V | W | Q | N | R | E | V | F |
| SEQ ID NO:13 | A | M | V | F | F | K | V | V | W | Q | N | R | E | V | F |

| | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|
| | * | | | | | | | | | | | | | | |
| phNGAL98 | K | I | T | L | Y | G | R | T | K | E | L | T | S | E | L |
| SEQ ID NO:1 | W | I | T | L | Y | G | R | T | K | E | L | T | S | E | L |
| SEQ ID NO:8 | W | V | T | L | Y | G | R | T | K | E | L | T | S | E | L |
| SEQ ID NO:9 | W | I | T | L | Y | G | R | T | K | E | L | T | S | G | L |
| SEQ ID NO:10 | W | I | T | L | Y | G | R | T | K | E | L | T | P | E | L |
| SEQ ID NO:11 | W | I | T | L | Y | G | R | T | K | E | L | T | S | G | L |
| SEQ ID NO:12 | W | I | T | L | Y | G | R | T | K | E | L | T | S | E | L |
| SEQ ID NO:13 | W | V | T | L | Y | G | R | T | K | E | L | T | S | E | L |

FIG. 3H

| SEQ ID NO | 149 | 150 | 151 | 152 | 153 | 154 | 155 | 156 | 157 | 158 | 159 | 160 | 161 | 162 | 163 | 164 |
|---|---|---|---|---|---|---|---|---|---|---|---|---|---|---|---|---|
| (phNGAL98) | K | E | N | F | I | R | F | S | K | S | L | G | L | P | E | N |
| 1 | K | E | N | F | I | R | F | S | K | S | L | G | L | P | E | N |
| 8 | K | E | N | F | I | R | F | S | K | S | L | G | L | P | E | N |
| 9 | K | E | N | F | I | R | F | S | K | S | L | G | L | P | E | N |
| 10 | K | E | N | F | I | R | F | S | K | S | L | G | L | P | E | N |
| 11 | K | E | N | F | I | R | F | S | K | S | L | G | L | P | E | N |
| 12 | K | K | N | F | I | R | F | S | K | S | L | G | L | P | E | N |
| 13 | K | E | N | F | I | R | F | S | K | S | L | G | L | P | E | N |

| SEQ ID NO | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|
| (phNGAL98) | H | I | V | F | P | V | P | I | D | Q | C | I | D | G | S |
| 1 | H | I | V | F | P | V | P | I | D | Q | C | I | D | G | S |
| 8 | H | I | V | F | P | V | P | I | D | Q | C | I | D | G | S |
| 9 | H | I | V | F | P | V | P | I | D | Q | C | I | D | G | S |
| 10 | H | I | V | F | P | V | P | I | D | Q | C | I | D | G | S |
| 11 | H | I | V | F | P | V | P | I | D | Q | C | I | D | G | S |
| 12 | H | I | V | F | P | V | P | I | D | Q | C | I | D | G | S |
| 13 | H | I | V | F | P | V | P | I | D | Q | C | I | D | G | S |

| | 180 | 181 | 182 | 183 | 184 | 185 | 186 |
|---|---|---|---|---|---|---|---|
| phNGAL98 | A | W | S | H | P | Q | F |
| SEQ ID NO:1 | A | W | S | H | P | Q | F |
| SEQ ID NO:8 | A | W | S | H | P | Q | F |
| SEQ ID NO:9 | A | W | S | H | P | Q | F |
| SEQ ID NO:10 | A | W | S | H | P | Q | F |
| SEQ ID NO:11 | A | W | S | H | P | Q | F |
| SEQ ID NO:12 | A | W | S | H | P | Q | F |
| SEQ ID NO:13 | A | W | S | H | P | Q | F |

QDSTSDLIPAPPLSKVPLQQNFQDNQFHGKWYVVGLAGNEVLREDKDPMKMWATIYELEEDK
SYNVTIVMFLAKKCEYLFQTFVPGSQPGEFTLGDIKSSPGRTSGLVRVVSTNYNQHAMVFFK
TVWQNREVFWITLYGRTKELTSELKENFIRFSKSLGLPENHIVFPVPIDQCIDG*SAGAVDAN*
*S*LAEAKVLANRELDKYGVSDYYKNLINNAKTVEGVKALIDEILAALP*SAWSHP*QFEK

Fig. 4A (SEQ ID NO:15)

*MASMTGGQQMG*QDSTSDLIPAPPLSKVPLQQNFQDNQFHGKWY
VVGLAGNAILREDKDPQKMYATIYELKEDKSYNVTSVLFRKKK
CDYWIRTFVPGSQPGEFTLGNIKSYPGLTSYLVRVVSTNYNQH
AMVFFKKVSQNREYFKITLYGRTKELTSELKENFIRFSKSLGL
PENHIVFPVPIDQCIDG*SAWSHPQF*

Fig. 4B

| | $K_D$ (M) | |
|---|---|---|
| Lipocalin Mutein | human hep-25 | cynomolgus hep-25 |
| SEQ ID NO: 1 | 0.26 | 0.43 |
| SEQ ID NO: 2 | 2.12 | 3.15 |
| SEQ ID NO: 3 | 0.84 | 0.59 |
| SEQ ID NO: 4 | 1.39 | 2.03 |
| SEQ ID NO: 5 | 4.13 | 6.83 |
| SEQ ID NO: 6 | 0.76 | 0.79 |
| SEQ ID NO: 7 | 0.48 | 0.22 |
| SEQ ID NO: 8 | 0.66 | 0.67 |
| SEQ ID NO: 9 | 0.75 | 1.14 |
| SEQ ID NO: 10 | 0.75 | 0.82 |
| SEQ ID NO: 11 | 0.64 | 0.61 |
| SEQ ID NO: 12 | 0.64 | 0.96 |
| SEQ ID NO. 14-PEG40 | 2.18 | 1.36 |
| SEQ ID NO. 13-PEG40 | 3.49 | n.d. |
| SEQ ID NO. 15-ABD | 0.48 | 0.22 |

FIG. 5

| Lipocalin Mutein | IC50 (nM) |
|---|---|
| SEQ ID NO: 1 | 0.34 |
| SEQ ID NO: 2 | 9.00 |
| SEQ ID NO: 3 | 0.38 |
| SEQ ID NO: 4 | 0.60 |
| SEQ ID NO: 5 | 10.8 |
| SEQ ID NO: 6 | 1.70 |
| SEQ ID NO: 7 | 1.3 |
| SEQ ID NO: 8 | 0.10 |
| SEQ ID NO: 9 | 0.12 |
| SEQ ID NO: 10 | 0.18 |
| SEQ ID NO: 11 | 0.11 |
| SEQ ID NO: 12 | 0.17 |
| SEQ ID NO. 14-PEG40 | 1.17 |
| SEQ ID NO. 13-PEG40 | 0.24 |
| SEQ ID NO. 15-ABD | 0.37 |

Fig. 6

| target | Lipocalin mutein | $K_{on}$ ($M^{-1}s^{-1}$) | $K_{off}$ ($s^{-1}$) | $K_D$ (M) |
|---|---|---|---|---|
| human Hep-25 | SEQ ID NO: 1 | 1.97 E+06 | 11.6 E-04 | 5.89 E-10 |
| | SEQ ID NO: 8 | 1.45 E+06 | 1.78 E-04 | 1.23 E-10 |
| | SEQ ID NO. 13-PEG40 | 2.98 E+06 | 1.23 E-04 | 4.10 E-11 |
| cyno Hep-25 | SEQ ID NO: 1 | 2.84 E+06 | 9.34 E-04 | 3.32 E-10 |
| | SEQ ID NO: 8 | 3.74 E+06 | 2.45 E-04 | 6.60 E-11 |

Fig. 7

| Lipocalin Mutein | IC50 (nM) |
|---|---|
| SEQ ID NO: 1 | 66 |
| SEQ ID NO: 2 | 62 |
| SEQ ID NO: 4 | 62 |
| SEQ ID NO: 6 | 65 |
| SEQ ID NO: 7 | 79 |
| SEQ ID NO: 8 | 31 |
| SEQ ID NO: 10 | 25 |
| SEQ ID NO: 11 | 31 |
| SEQ ID NO. 14-PEG40 | 25 |
| SEQ ID NO. 15-ABD | 39 |
| SEQ ID NO. 13-PEG40 | 34 |

FIG. 8

| Lipocalin Mutein | species | route | dose | T½ [h] |
|---|---|---|---|---|
| SEQ ID NO. 14-PEG | mouse | i.v. | 2mg/kg | 27.9 |
| SEQ ID NO. 15-ABD | mouse | i.v. | 2mg/kg | 30 |
| SEQ ID NO. 14-PEG | Cyno | i.v. | 0.3mg/kg | 88 |

FIG. 10

```
                         SEQUENCE LISTING


<160> NUMBER OF SEQ ID NOS: 48

<210> SEQ ID NO 1
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Glu Glu Asp Lys Ser Tyr
    50                  55                  60
```

```
Asn Val Thr Ile Val Met Phe Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Thr Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 2
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Thr Ala Gly Asn Ser Ile Leu Arg Glu Asp Lys Asp Pro
        35                  40                  45

Gln Lys Met Trp Ala Thr Ile Tyr Glu Leu Lys Glu Asp Lys Ser Tyr
    50                  55                  60

Asn Val Thr Arg Val Phe Phe Glu Gly Lys Lys Cys Arg Tyr Val Ile
65                  70                  75                  80

Glu Thr Phe Val Pro Gly Ser Gln Pro Gly Glu Phe Thr Leu Gly Lys
                85                  90                  95

Ile Lys Ser Ala Pro Gly Gly Thr Ser Ile Leu Val Arg Val Val Ser
            100                 105                 110

Thr Asn Tyr Asn Gln His Ala Met Val Phe Phe Lys Val Val Trp Gln
        115                 120                 125

Asn Arg Glu Leu Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 3
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL
```

<400> SEQUENCE: 3

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Gly Leu Leu Arg Glu Asp Lys Asp Pro
        35                  40                  45

Leu Lys Met His Ala Thr Ile Tyr Glu Leu Lys Glu Asp Lys Ser Tyr
    50                  55                  60

Asn Val Thr Arg Val Leu Phe Val Arg Lys Lys Cys Arg Tyr Tyr Ile
65                  70                  75                  80

Ser Thr Phe Val Pro Gly Ser Gln Pro Gly Glu Phe Thr Leu Gly Arg
                85                  90                  95

Ile Lys Ser Glu Pro Gly Arg Thr Ser Phe Leu Val Arg Val Val Ser
            100                 105                 110

Thr Asn Tyr Asn Gln His Ala Met Val Phe Phe Lys Met Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 4
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 4

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Met Leu Arg Glu Asp Lys Asp Pro
        35                  40                  45

Leu Lys Met Leu Ala Thr Ile Tyr Glu Leu Lys Glu Asp Lys Ser Tyr
    50                  55                  60

Asn Val Thr Arg Val Met Phe Glu Tyr Lys Lys Cys Val Tyr Leu Ile
65                  70                  75                  80

Glu Thr Phe Val Pro Gly Ser Gln Pro Gly Glu Phe Thr Leu Gly Thr
                85                  90                  95

Ile Lys Ser Val Pro Gly Leu Thr Ser Gly Leu Val Arg Val Val Ser
            100                 105                 110

Thr Asn Tyr Asn Gln His Ala Met Val Phe Phe Lys Arg Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
                165                 170                 175

Asp Gly


<210> SEQ ID NO 5
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ala Ala Gly Asn Ser Leu Leu Arg Glu Asp Lys Asp Pro
        35                  40                  45

Met Lys Met Trp Ala Thr Ile Tyr Glu Leu Lys Glu Asp Lys Ser Tyr
    50                  55                  60

Asn Val Thr Arg Val Asn Phe Gly Gly Lys Lys Cys Ser Tyr Leu Ile
65                  70                  75                  80

Glu Thr Phe Val Pro Gly Ser Gln Pro Gly Glu Phe Thr Leu Gly Ser
                85                  90                  95

Ile Lys Ser Arg Pro Gly Ala Thr Ser Val Leu Val Arg Val Val Ser
            100                 105                 110

Thr Asn Tyr Asn Gln His Ala Met Val Phe Phe Lys Leu Val Thr Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 6
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Ile Leu Arg Glu Asp Lys Asp Pro
        35                  40                  45

Leu Lys Met Trp Ala Thr Ile Tyr Glu Leu Lys Glu Asp Lys Ser Tyr
    50                  55                  60

Asn Val Thr Arg Val Gln Phe Gly Glu Lys Lys Cys Gly Tyr Gly Ile
65                  70                  75                  80

Glu Thr Phe Val Pro Gly Ser Gln Pro Gly Glu Phe Thr Leu Gly Ser
                85                  90                  95
```

```
Ile Lys Ser Val Pro Gly Gly Thr Ser Arg Leu Val Arg Val Val Ser
            100                 105                 110

Thr Asn Tyr Asn Gln His Ala Met Val Phe Phe Lys Phe Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 7
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Val Leu Arg Glu Asp Lys Asp Pro
        35                  40                  45

Gln Lys Met Phe Ala Thr Ile Tyr Glu Leu Lys Glu Asp Lys Ser Tyr
    50                  55                  60

Asn Val Thr Gly Val Asp Phe Arg Thr Lys Lys Cys Leu Tyr Ser Ile
65                  70                  75                  80

Gly Thr Phe Val Pro Gly Ser Gln Pro Gly Glu Phe Thr Leu Gly Val
                85                  90                  95

Ile Lys Ser Gln Pro Gly Trp Thr Ser Tyr Leu Val Arg Val Val Ser
            100                 105                 110

Thr Asn Tyr Asn Gln His Ala Met Val Phe Phe Lys Thr Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 8
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Leu Ala Gly Asn Glu Val Leu Arg Glu Asp Lys Asp Pro
        35                  40                  45

Met Lys Met Trp Ala Thr Ile Tyr Glu Leu Lys Glu Asp Lys Ser Tyr
    50                  55                  60

Asn Val Thr Ile Val Met Pro Leu Ala Glu Lys Cys Glu Tyr Leu Phe
65                  70                  75                  80

Gln Thr Phe Val Pro Gly Ser Gln Pro Gly Glu Phe Thr Leu Gly Gly
                85                  90                  95

Ile Lys Ser Gly Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Val Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 9
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Lys Glu Asp Lys Ser Tyr
    50                  55                  60

Asn Val Thr Ile Val Met Ser Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Ile Thr Leu Tyr Gly Arg Thr Lys Glu Leu
    130                 135                 140

Thr Ser Gly Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 10
<211> LENGTH: 179
<212> TYPE: PRT
<213> ORGANISM: Artificial Sequence
<220> FEATURE:
<223> OTHER INFORMATION: Description of Artificial Sequence: Synthetic Mutein of hNGAL

<400> SEQUENCE: 10

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Ile Leu Arg Glu Asp Lys Asp Pro
        35                  40                  45

Met Lys Met Trp Ala Thr Ile Tyr Glu Leu Lys Glu Asp Arg Ser Tyr
    50                  55                  60

Asn Val Thr Ile Val Met Phe Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Ile Thr Leu Tyr Gly Arg Thr Lys Glu Leu
    130                 135                 140

Thr Pro Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Phe
```

<210> SEQ ID NO 11
<211> LENGTH: 178
<212> TYPE: PRT
<213> ORGANISM: Artificial Sequence
<220> FEATURE:
<223> OTHER INFORMATION: Description of Artificial Sequence: Synthetic Mutein of hNGAL

<400> SEQUENCE: 11

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Ile Leu Arg Glu Asp Lys Asp Pro
        35                  40                  45

Met Lys Met Trp Ala Thr Ile Tyr Glu Leu Lys Glu Asp Lys Ser Tyr
    50                  55                  60

Asn Val Thr Ile Val Met Phe Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125
```

```
Asn Arg Glu Val Phe Trp Ile Thr Leu Tyr Gly Arg Thr Lys Glu Leu
    130                 135                 140

Thr Ser Gly Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 12
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Lys Glu Asp Lys Ser Tyr
    50                  55                  60

Asn Val Thr Ile Val Met Phe Leu Ala Glu Glu Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Lys Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 13
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Lys Glu Asp Lys Ser Tyr
    50                  55                  60
```

```
Asn Val Thr Ile Val Met Pro Leu Ala Glu Lys Cys Glu Tyr Leu Phe
65                  70                  75                  80

Gln Thr Phe Val Pro Gly Cys Gln Pro Gly Glu Phe Thr Leu Gly Gly
                85                  90                  95

Ile Lys Ser Gly Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Val Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 14
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL

<400> SEQUENCE: 14

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Glu Glu Asp Lys Ser Tyr
    50                  55                  60

Asn Val Thr Ile Val Met Phe Leu Ala Lys Lys Cys Glu Tyr Leu Phe
65                  70                  75                  80

Gln Thr Phe Val Pro Gly Cys Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Thr Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 15
<211> LENGTH: 243
<212> TYPE: PRT
<213> ORGANISM: Artificial Sequence
<220> FEATURE:
<223> OTHER INFORMATION: Description of Artificial Sequence: Synthetic
      Mutein of hNGAL with ABD domain and STREP tag
```

-continued

<400> SEQUENCE: 15

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Glu Val Leu Arg Glu Asp Lys Asp Pro
        35                  40                  45

Met Lys Met Trp Ala Thr Ile Tyr Glu Leu Glu Glu Asp Lys Ser Tyr
    50                  55                  60

Asn Val Thr Ile Val Met Phe Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Gly Ala Val Asp Ala Asn Ser Leu Ala Glu Ala Lys
            180                 185                 190

Val Leu Ala Asn Arg Glu Leu Asp Lys Tyr Gly Val Ser Asp Tyr Tyr
        195                 200                 205

Lys Asn Leu Ile Asn Asn Ala Lys Thr Val Glu Gly Val Lys Ala Leu
    210                 215                 220

Ile Asp Glu Ile Leu Ala Ala Leu Pro Ser Ala Trp Ser His Pro Gln
225                 230                 235                 240

Phe Glu Lys
```

<210> SEQ ID NO 16
<211> LENGTH: 88
<212> TYPE: DNA
<213> ORGANISM: Artificial Sequence
<220> FEATURE:
<223> OTHER INFORMATION: Description of Artificial Sequence: Synthetic NNK oligomer for positions 36, 40, 41, 49, 52
<220> FEATURE:
<221> NAME/KEY: modified_base
<222> LOCATION: (20)..(21)
<223> OTHER INFORMATION: a, c, g, or t
<220> FEATURE:
<221> NAME/KEY: modified_base
<222> LOCATION: (32)..(33)
<223> OTHER INFORMATION: a, c, g, or t
<220> FEATURE:
<221> NAME/KEY: modified_base
<222> LOCATION: (35)..(36)
<223> OTHER INFORMATION: a, c, g, or t
<220> FEATURE:
<221> NAME/KEY: modified_base
<222> LOCATION: (59)..(60)
<223> OTHER INFORMATION: a, c, g, or t
<220> FEATURE:
<221> NAME/KEY: modified_base
<222> LOCATION: (68)..(69)
<223> OTHER INFORMATION: a, c, g, or t

<400> SEQUENCE: 16
gaagtggtat gtggtaggtn nkgcagggaa tnnknnkctc agagaagaca aagacccgnn 60
kaagatgnnk gccaccatct atgagctg 88

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic NNK oligomer for positions 68, 70, 72, 73, 77, 79, 81
<220> FEATURE:
<221> NAME/KEY: modified_base
<222> LOCATION: (20)..(21)
<223> OTHER INFORMATION: a, c, g, or t
<220> FEATURE:
<221> NAME/KEY: modified_base
<222> LOCATION: (26)..(27)
<223> OTHER INFORMATION: a, c, g, or t
<220> FEATURE:
<221> NAME/KEY: modified_base
<222> LOCATION: (32)..(33)
<223> OTHER INFORMATION: a, c, g, or t
<220> FEATURE:
<221> NAME/KEY: modified_base
<222> LOCATION: (35)..(36)
<223> OTHER INFORMATION: a, c, g, or t
<220> FEATURE:
<221> NAME/KEY: modified_base
<222> LOCATION: (47)..(48)
<223> OTHER INFORMATION: a, c, g, or t
<220> FEATURE:
<221> NAME/KEY: modified_base
<222> LOCATION: (53)..(54)
<223> OTHER INFORMATION: a, c, g, or t
<220> FEATURE:
<221> NAME/KEY: modified_base
<222> LOCATION: (59)..(60)
<223> OTHER INFORMATION: a, c, g, or t

<400> SEQUENCE: 17
caagagctac aatgtcaccn nkgtcnnktt tnnknnkaag aagtgtnnkt acnnkatcnn 60
kacttttgtt ccaggttcc 79

<210> SEQ ID NO 18
<211> LENGTH: 68
<212> TYPE: DNA
<213> ORGANISM: Artificial Sequence
<220> FEATURE:
<223> OTHER INFORMATION: Description of Artificial Sequence: Synthetic NNK oligomer for positions 96, 100, 103, 106
<220> FEATURE:
<221> NAME/KEY: modified_base
<222> LOCATION: (19)..(20)
<223> OTHER INFORMATION: a, c, g, or t
<220> FEATURE:
<221> NAME/KEY: modified_base
<222> LOCATION: (31)..(32)
<223> OTHER INFORMATION: a, c, g, or t
<220> FEATURE:
<221> NAME/KEY: modified_base
<222> LOCATION: (40)..(41)
<223> OTHER INFORMATION: a, c, g, or t
<220> FEATURE:
<221> NAME/KEY: modified_base
<222> LOCATION: (49)..(50)
<223> OTHER INFORMATION: a, c, g, or t

<400> SEQUENCE: 18
ggcgagttca cgctgggcnn kattaagagt nnkcctggan nkacgagtnn kctcgtccga 60
gtggtgag 68

```
<210> SEQ ID NO 19
<211> LENGTH: 68
<212> TYPE: DNA
<213> ORGANISM: Artificial Sequence
<220> FEATURE:
<223> OTHER INFORMATION: Description of Artificial Sequence: Synthetic
      NNK oligomer for positions 125, 127, 132, 134
<220> FEATURE:
<221> NAME/KEY: modified_base
<222> LOCATION: (19)..(20)
<223> OTHER INFORMATION: a, c, g, or t
<220> FEATURE:
<221> NAME/KEY: modified_base
<222> LOCATION: (25)..(26)
<223> OTHER INFORMATION: a, c, g, or t
<220> FEATURE:
<221> NAME/KEY: modified_base
<222> LOCATION: (40)..(41)
<223> OTHER INFORMATION: a, c, g, or t
<220> FEATURE:
<221> NAME/KEY: modified_base
<222> LOCATION: (46)..(47)
<223> OTHER INFORMATION: a, c, g, or t

<400> SEQUENCE: 19

gctatggtgt tcttcaagnn kgttnnkcaa aacagggagn nkttcnnkat caccctctac     60

gggagaac                                                               68


<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 20

ggtgacattg tagctcttgt cttctttcag ctcatagatg gtggc                      45


<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 21

gcccagcgtg aactcgcctg gctgggaacc tggaacaaaa gt                         42


<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 22

cttgaagaac accatagcat gctggttgta gttggtgctc accactcgga cgag            54


<210> SEQ ID NO 23
<211> LENGTH: 64
<212> TYPE: DNA
<213> ORGANISM: Artificial Sequence
```

```
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 23

ggagaagcgg atgaagttct cctttagttc cgaagtcagc tccttggttc tcccgtagag     60

ggtg                                                                  64


<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      5' flanking PCR-Oligo biotinylated

<400> SEQUENCE: 24

ccaggacaac caattccatg ggaagtggta tgtggtaggt                           40


<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      3' flanking PCR-Oligo biotinylated

<400> SEQUENCE: 25

ttcagggagg cccagagatt tggagaagcg gatgaagttc                           40


<210> SEQ ID NO 26
<211> LENGTH: 4746
<212> TYPE: DNA
<213> ORGANISM: Artificial Sequence
<220> FEATURE:
<223> OTHER INFORMATION: Description of Artificial Sequence: Synthetic
      Phage display vector phNGAL102 with CamR used
      as backbone for NNK-Library

<400> SEQUENCE: 26

ccataacgct cggttgccgc cgggcgtttt ttattggcca gatgattaat tcctaatttt     60

tgttgacact ctatcattgg tagagttatt ttaccactcc ctatcagtga tagagaaaag    120

tgaaatgaat agttcgacaa aaatctagat aacgagggca aaaaatgaaa aagacagcta    180

tcgcgattgc agtggctctg gctggcttcg ctaccgtagc gcaggcccag gactccacct    240

cagacctgat cccagcccca cctctgagca aggtccctct gcagcagaac ttccaggaca    300

accaattcca tgggaagtgg tatgtggtag gtctcgcagg gaatgcaatt ctcagagaag    360

acaaagaccc gcaaaagatg tatgccacca tctatgagct gaaagaagac aagagctaca    420

atgtcacctc cgtcctgttt aggaaaaaga agtgtgacta ctggatcagg acttttgttc    480

caggttccca gccaggcgag ttcacgctgg gcaacattaa gagttaccct ggattaacga    540

gttacctcgt ccgagtggtg agcaccaact acaaccagca tgctatggtg ttcttcaaga    600

aagtttctca aaacagggag tacttcaaga tcaccctcta cgggagaacc aaggagctga    660

cttcggaact aaaggagaac ttcatccgct tctccaaatc tctgggcctc cctgaaaacc    720

acatcgtctt ccctgtccca atcgaccagt gtatcgacgg cagcgctggt ggggcctaga    780

ctgttgaaag ttgtttagca aaaccccata cagaaaattc atttactaac gtctggaaag    840

acgacaaaac tttagatcgt tacgctaact atgagggctg tctgtggaat gctacaggcg    900
```

```
ttgtagtttg tactggtgac gaaactcagt gttacggtac atgggttcct attgggcttg    960
ctatccctga aaatgagggt ggtggctctg agggtggcgg ttctgagggt ggcggttctg   1020
agggtggcgg tactaaacct cctgagtacg gtgatacacc tattccgggc tatacttata   1080
tcaaccctct cgacggcact tatccgcctg gtactgagca aaaccccgct aatcctaatc   1140
cttctcttga ggagtctcag cctcttaata ctttcatgtt tcagaataat aggttccgaa   1200
ataggcaggg ggcattaact gtttatacgg gcactgttac tcaaggcact gaccccgtta   1260
aaacttatta ccagtacact cctgtatcat caaaagccat gtatgacgct tactggaacg   1320
gtaaattcag agactgcgct ttccattctg gctttaatga ggatccattc gtttgtgaat   1380
atcaaggcca atcgtctgac ctgcctcaac ctcctgtcaa tgctggcggc ggctctggtg   1440
gtggttctgg tggcggctct gagggtggtg gctctgtggg tggcggttct gagggtggcg   1500
gctctgaggg aggcggttcc ggtggtggct ctggttccgg tgattttgat tatgaaaaga   1560
tggcaaacgc taataagggg gctatgaccg aaaatgccga tgaaaacgcg ctacagtctg   1620
acgctaaagg caaacttgat tctgtcgcta ctgattacgg tgctgctatc gatggtttca   1680
ttggtgacgt ttccggcctt gctaatggta atggtgctac tggtgatttt gctggctcta   1740
attcccaaat ggctcaagtc ggtgacggtg ataattcacc tttaatgaat aatttccgtc   1800
aatatttacc ttccctccct caatcggttg aatgtcgccc ttttgtcttt ggcgctggta   1860
aaccatatga attttctatt gattgtgaca aaataaactt attccgtggt gtctttgcgt   1920
ttcttttata tgttgccacc tttatgtatg tattttctac gtttgctaac atactgcgta   1980
ataaggagtc ttaataagct tgacctgtga agtgaaaaat ggcgcacatt gtgcgacatt   2040
tttttgtct  gccgtttacc gctactgcgt cacggatctc cacgcgccct gtagcggcgc   2100
attaagcgcg gcgggtgtgg tggttacgcg cagcgtgacc gctacacttg ccagcgccct   2160
agcgcccgct cctttcgctt tcttcccttc ctttctcgcc acgttcgccg gctttccccg   2220
tcaagctcta aatcgggggc tccctttagg gttccgattt agtgctttac ggcacctcga   2280
ccccaaaaaa cttgattagg gtgatggttc acgtagtggg ccatcgccct gatagacggt   2340
ttttcgccct ttgacgttgg agtccacgtt ctttaatagt ggactcttgt tccaaactgg   2400
aacaacactc aaccctatct cggtctattc ttttgattta taagggattt tgccgatttc   2460
ggcctattgg ttaaaaaatg agctgattta acaaaaattt aacgcgaatt ttaacaaaat   2520
ttggcgaaaa tgagacgttg atcggcacgt aagaggttcc aactttcacc ataatgaaat   2580
aagatcacta ccgggcgtat tttttgagtt atcgagattt tcaggagcta aggaagctaa   2640
aatggagaaa aaaatcactg gatataccac cgttgatata tcccaatggc atcgtaaaga   2700
acattttgag gcatttcagt cagttgctca atgtacctat aaccagaccg ttcagctgga   2760
tattacggcc tttttaaaga ccgtaaagaa aaataagcac aagttttatc cggcctttat   2820
tcacattctt gcccgcctga tgaatgctca tccggaattc cgtatggcaa tgaaagacgg   2880
tgagctggtg atatgggata gtgttcaccc ttgttacacc gttttccatg agcaaactga   2940
aacgttttca tcgctctgga gtgaatacca cgacgatttc cggcagtttc tacacatata   3000
ttcgcaagat gtggcgtgtt acggtgaaaa cctggcctat ttccctaaag ggtttattga   3060
gaatatgttt ttcgtctcag ccaatccctg ggtgagtttc accagttttg atttaaacgt   3120
ggccaatatg gacaacttct tcgcccccgt tttcactatg ggcaaatatt atacgcaagg   3180
cgacaaggtg ctgatgccgc tggcgattca ggttcatcat gccgtttgtg atggcttcca   3240
tgtcggcaga atgcttaatg aattacaaca gtactgcgat gagtggcagg gcggggcgta   3300
```

```
ataggaatta atgatgtctc gtttagataa aagtaaagtg attaacagcg cattagagct   3360
gcttaatgag gtcggaatcg aaggtttaac aacccgtaaa ctcgcccaga agctaggtgt   3420
agagcagcct acattgtatt ggcatgtaaa aaataagcgg gctttgctcg acgccttagc   3480
cattgagatg ttagataggc accatactca cttttgccct ttagaagggg aaagctggca   3540
agatttttta cgtaataacg ctaaaagttt tagatgtgct ttactaagtc atcgcgatgg   3600
agcaaaagta catttaggta cacggcctac agaaaaacag tatgaaactc tcgaaaatca   3660
attagccttt ttatgccaac aaggtttttc actagagaat gcattatatg cactcagcgc   3720
agtggggcat tttactttag gttgcgtatt ggaagatcaa gagcatcaag tcgctaaaga   3780
agaaagggaa acacctacta ctgatagtat gccgccatta ttacgacaag ctatcgaatt   3840
atttgatcac caaggtgcag agccagcctt cttattcggc cttgaattga tcatatgcgg   3900
attagaaaaa caacttaaat gtgaaagtgg gtcttaaaag cagcataacc tttttccgtg   3960
atggtaactt cactagttta aaggatcta ggtgaagatc ctttttgata atctcatgac   4020
caaaatccct taacgtgagt tttcgttcca ctgagcgtca gaccccgtag aaaagatcaa   4080
aggatcttct tgagatcctt tttttctgcg cgtaatctgc tgcttgcaaa caaaaaaacc   4140
accgctacca gcggtggttt gtttgccgga tcaagagcta ccaactcttt ttccgaaggt   4200
aactggcttc agcagagcgc agataccaaa tactgttctt ctagtgtagc cgtagttagg   4260
ccaccacttc aagaactctg tagcaccgcc tacatacctc gctctgctaa tcctgttacc   4320
agtggctgct gccagtggcg ataagtcgtg tcttaccggg ttggactcaa gacgatagtt   4380
accggataag gcgcagcggt cgggctgaac ggggggttcg tgcacacagc ccagcttgga   4440
gcgaacgacc tacaccgaac tgagatacct acagcgtgag ctatgagaaa gcgccacgct   4500
tcccgaaggg agaaaggcgg acaggtatcc ggtaagcggc agggtcggaa caggagagcg   4560
cacgagggag cttccagggg gaaacgcctg gtatctttat agtcctgtcg ggtttcgcca   4620
cctctgactt gagcgtcgat ttttgtgatg ctcgtcaggg gggcggagcc tatggaaaaa   4680
cgccagcaac gcggcctttt tacggttcct ggccttttgc tggccttttg ctcacatgac   4740
ccgaca                                                              4746
```

```
<210> SEQ ID NO 27
<211> LENGTH: 4963
<212> TYPE: DNA
<213> ORGANISM: Artificial Sequence
<220> FEATURE:
<223> OTHER INFORMATION: Description of Artificial Sequence: Synthetic
      Phage display vector phNGAL108 with AmpR used
      for Sloning Library

<400> SEQUENCE: 27
```

```
ccatcgaatg gccagatgat taattcctaa tttttgttga cactctatca ttgatagagt     60
tattttacca ctccctatca gtgatagaga aaagtgaaat gaatagttcg acaaaaatct    120
agataacgag ggcaaaaaat gaaaaagaca gctatcgcga ttgcagtggc tctggctggc    180
ttcgctaccg tagcgcaggc ccaggactcc acctcagacc tgatcccagc cccacctctg    240
agcaaggtcc ctctgcagca gaacttccag gacaaccaat tccatgggaa gtggtatgtg    300
gtaggtctcg cagggaatgc aattctcaga gaagacaaag acccgcaaaa gatgtatgcc    360
accatctatg agctgaaaga agacaagagc tacaatgtca cctccgtcct gtttaggaaa    420
aagaagtgtg actactggat caggactttt gttccaggtt cccagccagg cgagttcacg    480
ctgggcaaca ttaagagtta ccctggatta acgagttacc tcgtccgagt ggtgagcacc    540
```

```
aactacaacc agcatgctat ggtgttcttc aagaaagttt ctcaaaacag ggagtacttc    600
aagatcaccc tctacgggag aaccaaggag ctgacttcgg aactaaagga gaacttcatc    660
cgcttctcca aatctctggg cctccctgaa aaccacatcg tcttccctgt cccaatcgac    720
cagtgtatcg acggcagcgc ttggcgtcac ccgcagttcg gtggggccta gactgttgaa    780
agttgtttag caaaacccca tacagaaaat tcatttacta acgtctggaa agacgacaaa    840
actttagatc gttacgctaa ctatgagggc tgtctgtgga atgctacagg cgttgtagtt    900
tgtactggtg acgaaactca gtgttacggt acatgggttc ctattgggct tgctatccct    960
gaaaatgagg gtggtggctc tgagggtggc ggttctgagg gtggcggttc tgagggtggc   1020
ggtactaaac ctcctgagta cggtgataca cctattccgg gctatactta tatcaaccct   1080
ctcgacggca cttatccgcc tggtactgag caaaaccccg ctaatcctaa tccttctctt   1140
gaggagtctc agcctcttaa tactttcatg tttcagaata ataggttccg aaataggcag   1200
ggggcattaa ctgtttatac gggcactgtt actcaaggca ctgaccccgt taaaacttat   1260
taccagtaca ctcctgtatc atcaaaagcc atgtatgacg cttactggaa cggtaaattc   1320
agagactgcg ctttccattc tggctttaat gaggatccat tcgtttgtga atatcaaggc   1380
caatcgtctg acctgcctca acctcctgtc aatgctggcg gcggctctgg tggtggttct   1440
ggtggcggct ctgagggtgg tggctctgag ggtggcggtt ctgagggtgg cggctctgag   1500
ggaggcggtt ccggtggtgg ctctggttcc ggtgattttg attatgaaaa gatggcaaac   1560
gctaataagg gggctatgac cgaaaatgcc gatgaaaacg cgctacagtc tgacgctaaa   1620
ggcaaacttg attctgtcgc tactgattac ggtgctgcta tcgatggttt cattggtgac   1680
gtttccggcc ttgctaatgg taatggtgct actggtgatt ttgctggctc taattcccaa   1740
atggctcaag tcggtgacgg tgataattca cctttaatga ataatttccg tcaatattta   1800
ccttccctcc ctcaatcggt tgaatgtcgc ccttttgtct ttggcgctgg taaaccatat   1860
gaattttcta ttgattgtga caaaataaac ttattccgtg gtgtctttgc gtttctttta   1920
tatgttgcca cctttatgta tgtattttct acgtttgcta acatactgcg taataaggag   1980
tcttaataag cttgacctgt gaagtgaaaa atggcgcaca ttgtgcgaca ttttttttgt   2040
ctgccgttta ccgctactgc gtcacggatc tccacgcgcc ctgtagcggc gcattaagcg   2100
cggcgggtgt ggtggttacg cgcagcgtga ccgctacact tgccagcgcc ctagcgcccg   2160
ctcctttcgc tttcttccct tcctttctcg ccacgttcgc cggctttccc cgtcaagctc   2220
taaatcgggg gctcccttta gggttccgat ttagtgcttt acggcacctc gaccccaaaa   2280
aacttgatta gggtgatggt tcacgtagtg ggccatcgcc ctgatagacg gtttttcgcc   2340
ctttgacgtt ggagtccacg ttctttaata gtggactctt gttccaaact ggaacaacac   2400
tcaaccctat ctcggtctat tcttttgatt tataagggat tttgccgatt tcggcctatt   2460
ggttaaaaaa tgagctgatt taacaaaaat ttaacgcgaa ttttaacaaa atattaacgc   2520
ttacaatttc aggtggcact tttcggggaa atgtgcgcgg aacccctatt tgtttatttt   2580
tctaaataca ttcaaatatg tatccgctca tgagacaata accctgataa atgcttcaat   2640
aatattgaaa aaggaagagt atgagtattc aacatttccg tgtcgccctt attccctttt   2700
ttgcggcatt ttgccttcct gtttttgctc acccagaaac gctggtgaaa gtaaaagatg   2760
ctgaagatca gttgggtgca cgagtgggtt acatcgaact ggatctcaac agcggtaaga   2820
tccttgagag ttttcgcccc gaagaacgtt ttccaatgat gagcactttt aaagttctgc   2880
```

```
tatgtggcgc ggtattatcc cgtattgacg ccgggcaaga gcaactcggt cgccgcatac   2940

actattctca gaatgacttg gttgagtact caccagtcac agaaaagcat cttacggatg   3000

gcatgacagt aagagaatta tgcagtgctg ccataaccat gagtgataac actgcggcca   3060

acttacttct gacaacgatc ggaggaccga aggagctaac cgcttttttg cacaacatgg   3120

gggatcatgt aactcgcctt gatcgttggg aaccggagct gaatgaagcc ataccaaacg   3180

acgagcgtga caccacgatg cctgtagcaa tggcaacaac gttgcgcaaa ctattaactg   3240

gcgaactact tactctagct tcccggcaac aattgataga ctggatggag gcggataaag   3300

ttgcaggacc acttctgcgc tcggcccttc cggctggctg gtttattgct gataaatctg   3360

gagccggtga gcgtggctct cgcggtatca ttgcagcact ggggccagat ggtaagccct   3420

cccgtatcgt agttatctac acgacgggga gtcaggcaac tatggatgaa cgaaatagac   3480

agatcgctga gataggtgcc tcactgatta agcattggta ggaattaatg atgtctcgtt   3540

tagataaaag taaagtgatt aacagcgcat tagagctgct taatgaggtc ggaatcgaag   3600

gtttaacaac ccgtaaactc gcccagaagc taggtgtaga gcagcctaca ttgtattggc   3660

atgtaaaaaa taagcgggct ttgctcgacg ccttagccat tgagatgtta gataggcacc   3720

atactcactt ttgcccttta gaaggggaaa gctggcaaga tttttacgt aataacgcta   3780

aaagttttag atgtgcttta ctaagtcatc gcgatggagc aaaagtacat ttaggtacac   3840

ggcctacaga aaaacagtat gaaactctcg aaaatcaatt agcctttta tgccaacaag   3900

gtttttcact agagaatgca ttatatgcac tcagcgcagt ggggcatttt actttaggtt   3960

gcgtattgga agatcaagag catcaagtcg ctaaagaaga aagggaaaca cctactactg   4020

atagtatgcc gccattatta cgacaagcta tcgaattatt tgatcaccaa ggtgcagagc   4080

cagccttctt attcggcctt gaattgatca tatgcggatt agaaaaacaa cttaaatgtg   4140

aaagtgggtc ttaaaagcag cataaccttt ttccgtgatg gtaacttcac tagtttaaaa   4200

ggatctaggt gaagatcctt tttgataatc tcatgaccaa aatcccttaa cgtgagtttt   4260

cgttccactg agcgtcagac cccgtagaaa agatcaaagg atcttcttga gatccttttt   4320

ttctgcgcgt aatctgctgc ttgcaaacaa aaaaaccacc gctaccagcg gtggtttgtt   4380

tgccggatca agagctacca actctttttc cgaaggtaac tggcttcagc agagcgcaga   4440

taccaaatac tgtccttcta gtgtagccgt agttaggcca ccacttcaag aactctgtag   4500

caccgcctac atacctcgct ctgctaatcc tgttaccagt ggctgctgcc agtggcgata   4560

agtcgtgtct taccgggttg gactcaagac gatagttacc ggataaggcg cagcggtcgg   4620

gctgaacggg gggttcgtgc acacagccca gcttggagcg aacgacctac accgaactga   4680

gatacctaca gcgtgagcta tgagaaagcg ccacgcttcc cgaagggaga aaggcggaca   4740

ggtatccggt aagcggcagg gtcggaacag gagagcgcac gagggagctt ccagggggaa   4800

acgcctggta tctttatagt cctgtcgggt ttcgccacct ctgacttgag cgtcgatttt   4860

tgtgatgctc gtcagggggg cggagcctat ggaaaaacgc cagcaacgcg gcctttttac   4920

ggttcctggc cttttgctgg ccttttgctc acatgacccg aca                     4963
```

<210> SEQ ID NO 28
<211> LENGTH: 25
<212> TYPE: PRT
<213> ORGANISM: Homo sapiens
<220> FEATURE:
<223> OTHER INFORMATION: Hepcidin-25

<400> SEQUENCE: 28

Asp Thr His Phe Pro Ile Cys Ile Phe Cys Cys Gly Cys Cys His Arg
1 5 10 15

Ser Lys Cys Gly Met Cys Cys Lys Thr
20 25

<210> SEQ ID NO 29
<211> LENGTH: 25
<212> TYPE: PRT
<213> ORGANISM: Mus musculus
<220> FEATURE:
<223> OTHER INFORMATION: Hepcidin-25

<400> SEQUENCE: 29

Asp Thr Asn Phe Pro Ile Cys Ile Phe Cys Cys Lys Cys Cys Asn Asn
1 5 10 15

Ser Gln Cys Gly Ile Cys Cys Lys Thr
20 25

<210> SEQ ID NO 30
<211> LENGTH: 25
<212> TYPE: PRT
<213> ORGANISM: Rattus norvegicus
<220> FEATURE:
<223> OTHER INFORMATION: Hepcidin-25

<400> SEQUENCE: 30

Asp Thr Asn Phe Pro Ile Cys Leu Phe Cys Cys Lys Cys Cys Lys Asn
1 5 10 15

Ser Ser Cys Gly Leu Cys Cys Ile Thr
20 25

<210> SEQ ID NO 31
<211> LENGTH: 3745
<212> TYPE: DNA
<213> ORGANISM: Artificial Sequence
<220> FEATURE:
<223> OTHER INFORMATION: Description of Artificial Sequence: Synthetic
Expression vector phNGAL98 with AmpR encoding
wild type Lcn2 with the C-terminal Strep-tagII

<400> SEQUENCE: 31
ccatcgaatg gccagatgat taattcctaa tttttgttga cactctatca ttgatagagt 60
tattttacca ctccctatca gtgatagaga aaagtgaaat gaatagttcg acaaaaatct 120
agataacgag ggcaaaaaat gaaaaagaca gctatcgcga ttgcagtggc tctggctggc 180
ttcgctaccg tagcgcaggc ccaggactcc acctcagacc tgatcccagc cccacctctg 240
agcaaggtcc ctctgcagca gaacttccag gacaaccaat tccatgggaa gtggtatgtg 300
gtaggtctcg cagggaatgc aattctcaga gaagacaaag acccgcaaaa gatgtatgcc 360
accatctatg agctgaaaga agacaagagc tacaatgtca cctccgtcct gtttaggaaa 420
aagaagtgtg actactggat caggactttt gttccaggtt cccagccagg cgagttcacg 480
ctgggcaaca ttaagagtta ccctggatta acgagttacc tcgtccgagt ggtgagcacc 540
aactacaacc agcatgctat ggtgttcttc aagaaagttt ctcaaaacag ggagtacttc 600
aagatcaccc tctacgggag aaccaaggag ctgacttcgg aactaaagga gaacttcatc 660
cgcttctcca aatctctggg cctccctgaa aaccacatcg tcttccctgt cccaatcgac 720
cagtgtatcg acggcagcgc ttggtctcac ccgcagttcg aaaaataata agcttgacct 780
gtgaagtgaa aaatggcgca cattgtgcga catttttttt gtctgccgtt taccgctact 840

```
gcgtcacgga tctccacgcg ccctgtagcg gcgcattaag cgcggcgggt gtggtggtta    900
cgcgcagcgt gaccgctaca cttgccagcg ccctagcgcc cgctcctttc gctttcttcc    960
cttcctttct cgccacgttc gccggctttc cccgtcaagc tctaaatcgg gggctccctt   1020
tagggttccg atttagtgct ttacggcacc tcgaccccaa aaaacttgat tagggtgatg   1080
gttcacgtag tgggccatcg ccctgataga cggtttttcg ccctttgacg ttggagtcca   1140
cgttctttaa tagtggactc ttgttccaaa ctggaacaac actcaaccct atctcggtct   1200
attcttttga tttataaggg attttgccga tttcggccta ttggttaaaa aatgagctga   1260
tttaacaaaa atttaacgcg aattttaaca aaatattaac gtttacaatt tcaggtggca   1320
cttttcgggg aaatgtgcgc ggaaccccta tttgtttatt tttctaaata cattcaaata   1380
tgtatccgct catgagacaa taaccctgat aaatgcttca ataatattga aaaaggaaga   1440
gtatgagtat tcaacatttc cgtgtcgccc ttattccctt ttttgcggca ttttgccttc   1500
ctgtttttgc tcacccagaa acgctggtga aagtaaaaga tgctgaagat cagttgggtg   1560
cacgagtggg ttacatcgaa ctggatctca acagcggtaa gatccttgag agttttcgcc   1620
ccgaagaacg ttttccaatg atgagcactt ttaaagttct gctatgtggc gcggtattat   1680
cccgtattga cgccgggcaa gagcaactcg gtcgccgcat acactattct cagaatgact   1740
tggttgagta ctcaccagtc acagaaaagc atcttacgga tggcatgaca gtaagagaat   1800
tatgcagtgc tgccataacc atgagtgata acactgcggc caacttactt ctgacaacga   1860
tcggaggacc gaaggagcta accgcttttt tgcacaacat gggggatcat gtaactcgcc   1920
ttgatcgttg ggaaccggag ctgaatgaag ccataccaaa cgacgagcgt gacaccacga   1980
tgcctgtagc aatggcaaca acgttgcgca aactattaac tggcgaacta cttactctag   2040
cttcccggca acaattgata gactggatgg aggcggataa agttgcagga ccacttctgc   2100
gctcggccct tccggctggc tggtttattg ctgataaatc tggagccggt gagcgtggct   2160
ctcgcggtat cattgcagca ctggggccag atggtaagcc ctcccgtatc gtagttatct   2220
acacgacggg gagtcaggca actatggatg aacgaaatag acagatcgct gagataggtg   2280
cctcactgat taagcattgg taggaattaa tgatgtctcg tttagataaa agtaaagtga   2340
ttaacagcgc attagagctg cttaatgagg tcggaatcga aggtttaaca acccgtaaac   2400
tcgcccagaa gctaggtgta gagcagccta cattgtattg gcatgtaaaa aataagcggg   2460
ctttgctcga cgccttagcc attgagatgt tagataggca ccatactcac ttttgccctt   2520
tagaagggga aagctggcaa gattttttac gtaataacgc taaaagtttt agatgtgctt   2580
tactaagtca tcgcgatgga gcaaaagtac atttaggtac acggcctaca gaaaaacagt   2640
atgaaactct cgaaaatcaa ttagcctttt tatgccaaca aggtttttca ctagagaatg   2700
cattatatgc actcagcgca gtggggcatt ttactttagg ttgcgtattg gaagatcaag   2760
agcatcaagt cgctaaagaa gaaagggaaa cacctactac tgatagtatg ccgccattat   2820
tacgacaagc tatcgaatta tttgatcacc aaggtgcaga gccagccttc ttattcggcc   2880
ttgaattgat catatgcgga ttagaaaaac aacttaaatg tgaaagtggg tcttaaaagc   2940
agcataacct tttccgtga tggtaacttc actagtttaa aaggatctag gtgaagatcc    3000
tttttgataa tctcatgacc aaaatccctt aacgtgagtt ttcgttccac tgagcgtcag   3060
accccgtaga aaagatcaaa ggatcttctt gagatccttt ttttctgcgc gtaatctgct   3120
gcttgcaaac aaaaaaacca ccgctaccag cggtggtttg tttgccggat caagagctac   3180
caactctttt tccgaaggta actggcttca gcagagcgca gataccaaat actgtccttc   3240
```

```
tagtgtagcc gtagttaggc caccacttca agaactctgt agcaccgcct acatacctcg   3300

ctctgctaat cctgttacca gtggctgctg ccagtggcga taagtcgtgt cttaccgggt   3360

tggactcaag acgatagtta ccggataagg cgcagcggtc gggctgaacg gggggttcgt   3420

gcacacagcc cagcttggag cgaacgacct acaccgaact gagataccta cagcgtgagc   3480

tatgagaaag cgccacgctt cccgaaggga gaaaggcgga caggtatccg gtaagcggca   3540

gggtcggaac aggagagcgc acgagggagc ttccaggggg aaacgcctgg tatctttata   3600

gtcctgtcgg gtttcgccac ctctgacttg agcgtcgatt tttgtgatgc tcgtcagggg   3660

ggcggagcct atggaaaaac gccagcaacg cggccttttt acggttcctg gccttttgct   3720

ggccttttgc tcacatgacc cgaca                                          3745


<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

cccaggactc cacctcagac c                                                21


<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

actgcgggtg ggaccaagcg ctgccgt                                          27


<210> SEQ ID NO 34
<211> LENGTH: 197
<212> TYPE: PRT
<213> ORGANISM: Artificial Sequence
<220> FEATURE:
<223> OTHER INFORMATION: Description of Artificial Sequence: Synthetic
      hNGAL with T7 tag encoded by phNGAL 101

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asp
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Thr Val Ser Gln
        115                 120                 125
```

```
Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Met Ala Ser Met Thr Gly
            180                 185                 190

Gly Gln Gln Met Gly
        195


<210> SEQ ID NO 35
<211> LENGTH: 178
<212> TYPE: PRT
<213> ORGANISM: Artificial Sequence
<220> FEATURE:
<223> OTHER INFORMATION: Description of Artificial Sequence: Synthetic
      wild type hNGAL

<400> SEQUENCE: 35

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly


<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 36

ccannnnnnt gg                                                          12
```

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
5xHis tag

<400> SEQUENCE: 37

His His His His His
1 5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 38

His His His His His His
1 5

<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (59)..(60)
<223> OTHER INFORMATION: a, c, t, g, unknown or other

<400> SEQUENCE: 39
caagagctac aatgtcacan nkgtcnnktt tnnknnkaag aagtgtnnkt acnnkatcnn 60
kacttttgtt ccaggttcc 79

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
ggtgacattg tagctcttat cttctttcag ctcatagatg gtggc 45

<210> SEQ ID NO 41
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
ggagaagcgg atgaagttct cctttagttc cgaagccagc tccttggttc tcccgtagag 60
ggtg 64

<210> SEQ ID NO 42
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(564)

<400> SEQUENCE: 42

```
cag gac tcc acc tca gac ctg atc cca gcc cca cct ctg agc aag gtc       48
Gln Asp Ser Thr Ser Asp Leu Ile Pro Ala Pro Pro Leu Ser Lys Val
1               5                   10                  15

cct ctg cag cag aac ttc cag gac aac caa ttc cat ggg aag tgg tat       96
Pro Leu Gln Gln Asn Phe Gln Asp Asn Gln Phe His Gly Lys Trp Tyr
            20                  25                  30

gtg gta ggt ctc gca ggg aat gca att ctc aga gaa gac aaa gac ccg      144
Val Val Gly Leu Ala Gly Asn Ala Ile Leu Arg Glu Asp Lys Asp Pro
        35                  40                  45

caa aag atg tat gcc acc atc tat gag ctg aaa gaa gac aag agc tac      192
Gln Lys Met Tyr Ala Thr Ile Tyr Glu Leu Lys Glu Asp Lys Ser Tyr
    50                  55                  60

aat gtc acc tcc gtc ctg ttt agg aaa aag aag tgt gac tac tgg atc      240
Asn Val Thr Ser Val Leu Phe Arg Lys Lys Lys Cys Asp Tyr Trp Ile
65                  70                  75                  80

agg act ttt gtt cca ggt tcc cag cca ggc gag ttc acg ctg ggc aac      288
Arg Thr Phe Val Pro Gly Ser Gln Pro Gly Glu Phe Thr Leu Gly Asn
                85                  90                  95

att aag agt tac cct gga tta acg agt tac ctc gtc cga gtg gtg agc      336
Ile Lys Ser Tyr Pro Gly Leu Thr Ser Tyr Leu Val Arg Val Val Ser
            100                 105                 110

acc aac tac aac cag cat gct atg gtg ttc ttc aag aaa gtt tct caa      384
Thr Asn Tyr Asn Gln His Ala Met Val Phe Phe Lys Lys Val Ser Gln
        115                 120                 125

aac agg gag tac ttc aag atc acc ctc tac ggg aga acc aag gag ctg      432
Asn Arg Glu Tyr Phe Lys Ile Thr Leu Tyr Gly Arg Thr Lys Glu Leu
    130                 135                 140

act tcg gaa cta aag gag aac ttc atc cgc ttc tcc aaa tct ctg ggc      480
Thr Ser Glu Leu Lys Glu Asn Phe Ile Arg Phe Ser Lys Ser Leu Gly
145                 150                 155                 160

ctc cct gaa aac cac atc gtc ttc cct gtc cca atc gac cag tgt atc      528
Leu Pro Glu Asn His Ile Val Phe Pro Val Pro Ile Asp Gln Cys Ile
                165                 170                 175
```

```
gac ggc agc gct tgg tcc cac ccg cag ttc gaa aaa taa                 567
Asp Gly Ser Ala Trp Ser His Pro Gln Phe Glu Lys
            180                 185


<210> SEQ ID NO 43
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185


<210> SEQ ID NO 44
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

ttatttttcg aactgcgggt gggaccaagc gctgccgtcg atacactggt cgattgggac     60

agggaagacg atgtggtttt cagggaggcc cagagatttg gagaagcgga tgaagttctc    120

ctttagttcc gaagccagct ccttggttct cccgtagagg gtgatcttga agtactccct    180

gttttgagaa actttcttga agaacaccat agcatgctgg ttgtagttgg tgctcaccac    240

tcggacgagg taactcgtta atccaggtta actcttaatg ttgcccagcg tgaactcgcc    300

tggctgggaa cctggaacaa aagtcctgat ccagtagtca cacttctttt tcctaaacag    360

gacggaggtg acattgtagc tcttgtcttc tttcagctca tagatggtgg catacatctt    420

ttgcgggtct ttgtcttctc tgagaattgc attccctgcg agacctacca cataccactt    480
```

```
cccatggaat tggttgtcct ggaagttctg ctgcagaggg accttgctca gaggtggggc    540

tgggatcagg tctgaggtgg agtcctg                                        567


<210> SEQ ID NO 45
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(403)
<220> FEATURE:
<221> NAME/KEY: modified_base
<222> LOCATION: (32)..(34)
<223> OTHER INFORMATION: a, c, t, g, unknown or other
<220> FEATURE:
<221> NAME/KEY: modified_base
<222> LOCATION: (44)..(49)
<223> OTHER INFORMATION: a, c, t, g, unknown or other
<220> FEATURE:
<221> NAME/KEY: modified_base
<222> LOCATION: (71)..(73)
<223> OTHER INFORMATION: a, c, t, g, unknown or other
<220> FEATURE:
<221> NAME/KEY: modified_base
<222> LOCATION: (80)..(82)
<223> OTHER INFORMATION: a, c, t, g, unknown or other
<220> FEATURE:
<221> NAME/KEY: modified_base
<222> LOCATION: (128)..(130)
<223> OTHER INFORMATION: a, c, t, g, unknown or other
<220> FEATURE:
<221> NAME/KEY: modified_base
<222> LOCATION: (134)..(136)
<223> OTHER INFORMATION: a, c, t, g, unknown or other
<220> FEATURE:
<221> NAME/KEY: modified_base
<222> LOCATION: (140)..(145)
<223> OTHER INFORMATION: a, c, t, g, unknown or other
<220> FEATURE:
<221> NAME/KEY: modified_base
<222> LOCATION: (155)..(157)
<223> OTHER INFORMATION: a, c, t, g, unknown or other
<220> FEATURE:
<221> NAME/KEY: modified_base
<222> LOCATION: (161)..(163)
<223> OTHER INFORMATION: a, c, t, g, unknown or other
<220> FEATURE:
<221> NAME/KEY: modified_base
<222> LOCATION: (167)..(169)
<223> OTHER INFORMATION: a, c, t, g, unknown or other
<220> FEATURE:
<221> NAME/KEY: modified_base
<222> LOCATION: (212)..(214)
<223> OTHER INFORMATION: a, c, t, g, unknown or other
<220> FEATURE:
<221> NAME/KEY: modified_base
<222> LOCATION: (224)..(226)
<223> OTHER INFORMATION: a, c, t, g, unknown or other
<220> FEATURE:
<221> NAME/KEY: modified_base
<222> LOCATION: (233)..(235)
<223> OTHER INFORMATION: a, c, t, g, unknown or other
<220> FEATURE:
<221> NAME/KEY: modified_base
<222> LOCATION: (242)..(244)
<223> OTHER INFORMATION: a, c, t, g, unknown or other
<220> FEATURE:
<221> NAME/KEY: modified_base
<222> LOCATION: (299)..(301)
<223> OTHER INFORMATION: a, c, t, g, unknown or other
<220> FEATURE:
<221> NAME/KEY: modified_base
<222> LOCATION: (305)..(307)
<223> OTHER INFORMATION: a, c, t, g, unknown or other
```

```
<220> FEATURE:
<221> NAME/KEY: modified_base
<222> LOCATION: (320)..(322)
<223> OTHER INFORMATION: a, c, t, g, unknown or other
<220> FEATURE:
<221> NAME/KEY: modified_base
<222> LOCATION: (326)..(328)
<223> OTHER INFORMATION: a, c, t, g, unknown or other

<400> SEQUENCE: 45

c caa ttc cat ggg aaa tgg tat gtc gtg ggc nnn gcc gga aat nnn nnn     49
  Gln Phe His Gly Lys Trp Tyr Val Val Gly Xaa Ala Gly Asn Xaa Xaa
  1               5                   10                  15

ctg cgt gag gat aag gat ccg nnn aaa atg nnn gcg acc att tac gag       97
Leu Arg Glu Asp Lys Asp Pro Xaa Lys Met Xaa Ala Thr Ile Tyr Glu
            20                  25                  30

ttg aaa gaa gat aaa tca tat aac gtc acc nnn gtg nnn ttt nnn nnn      145
Leu Lys Glu Asp Lys Ser Tyr Asn Val Thr Xaa Val Xaa Phe Xaa Xaa
        35                  40                  45

aag aaa tgc nnn tac nnn att nnn acc ttt gtg ccg ggg agc cag ccg      193
Lys Lys Cys Xaa Tyr Xaa Ile Xaa Thr Phe Val Pro Gly Ser Gln Pro
    50                  55                  60

ggc gag ttt act tta ggc nnn att aaa agt nnn ccg ggc nnn aca tca      241
Gly Glu Phe Thr Leu Gly Xaa Ile Lys Ser Xaa Pro Gly Xaa Thr Ser
65                  70                  75                  80

nnn ttg gtc cgc gtc gtg agc acc aac tac aac cag cat gcc atg gtg      289
Xaa Leu Val Arg Val Val Ser Thr Asn Tyr Asn Gln His Ala Met Val
                85                  90                  95

ttc ttc aag nnn gtg nnn cag aac cgc gag nnn ttt nnn atc aca ctg      337
Phe Phe Lys Xaa Val Xaa Gln Asn Arg Glu Xaa Phe Xaa Ile Thr Leu
            100                 105                 110

tac ggg cgc acg aaa gaa ctg aca agc gag ctg aag gaa aat ttt atc      385
Tyr Gly Arg Thr Lys Glu Leu Thr Ser Glu Leu Lys Glu Asn Phe Ile
        115                 120                 125

cgc ttt tcc aaa tct ctg g                                            404
Arg Phe Ser Lys Ser Leu
    130


<210> SEQ ID NO 46
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (43)..(43)
<223> OTHER INFORMATION: Any amino acid
```

<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (107)..(107)
<223> OTHER INFORMATION: Any amino acid
<220> FEATURE:
<221> NAME/KEY: MOD_RES
<222> LOCATION: (109)..(109)
<223> OTHER INFORMATION: Any amino acid

<400> SEQUENCE: 46

```
Gln Phe His Gly Lys Trp Tyr Val Val Gly Xaa Ala Gly Asn Xaa Xaa
1               5                   10                  15

Leu Arg Glu Asp Lys Asp Pro Xaa Lys Met Xaa Ala Thr Ile Tyr Glu
            20                  25                  30

Leu Lys Glu Asp Lys Ser Tyr Asn Val Thr Xaa Val Xaa Phe Xaa Xaa
        35                  40                  45

Lys Lys Cys Xaa Tyr Xaa Ile Xaa Thr Phe Val Pro Gly Ser Gln Pro
    50                  55                  60

Gly Glu Phe Thr Leu Gly Xaa Ile Lys Ser Xaa Pro Gly Xaa Thr Ser
65                  70                  75                  80

Xaa Leu Val Arg Val Val Ser Thr Asn Tyr Asn Gln His Ala Met Val
                85                  90                  95

Phe Phe Lys Xaa Val Xaa Gln Asn Arg Glu Xaa Phe Xaa Ile Thr Leu
            100                 105                 110
```

```
Tyr Gly Arg Thr Lys Glu Leu Thr Ser Glu Leu Lys Glu Asn Phe Ile
        115                 120                 125

Arg Phe Ser Lys Ser Leu
    130


<210> SEQ ID NO 47
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

ccagagattt ggaaaagcgg ataaaatttt ccttcagctc gcttgtcagt tctttcgtgc     60

gcccgtacag tgtgatctta aagtactcgc ggttctggga cactttcttg aagaacacca    120

tggcatgctg gttgtagttg gtgctcacga cgcggaccaa gtatgatgtc aggcccgggt    180

aacttttaat gttgcctaaa gtaaactcgc ccggctggct ccccggcaca aaggtacgaa    240

tccagtagtc gcatttcttt ttgcgaaaca acacggaggt gacgttatat gatttatctt    300

ctttcaactc gtaaatggtc gcatacattt tctgcggatc cttatcctca cgcagaatgg    360

catttccggc caggcccacg acataccatt tcccatggaa ttgg                      404


<210> SEQ ID NO 48
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Ser Met Thr Gly Gly Gln Gln Met Gly Gln Asp Ser Thr Ser
1               5                   10                  15

Asp Leu Ile Pro Ala Pro Pro Leu Ser Lys Val Pro Leu Gln Gln Asn
            20                  25                  30

Phe Gln Asp Asn Gln Phe His Gly Lys Trp Tyr Val Val Gly Leu Ala
        35                  40                  45

Gly Asn Ala Ile Leu Arg Glu Asp Lys Asp Pro Gln Lys Met Tyr Ala
    50                  55                  60

Thr Ile Tyr Glu Leu Lys Glu Asp Lys Ser Tyr Asn Val Thr Ser Val
65                  70                  75                  80

Leu Phe Arg Lys Lys Lys Cys Asp Tyr Trp Ile Arg Thr Phe Val Pro
                85                  90                  95

Gly Ser Gln Pro Gly Glu Phe Thr Leu Gly Asn Ile Lys Ser Tyr Pro
            100                 105                 110

Gly Leu Thr Ser Tyr Leu Val Arg Val Val Ser Thr Asn Tyr Asn Gln
        115                 120                 125

His Ala Met Val Phe Phe Lys Lys Val Ser Gln Asn Arg Glu Tyr Phe
    130                 135                 140

Lys Ile Thr Leu Tyr Gly Arg Thr Lys Glu Leu Thr Ser Glu Leu Lys
145                 150                 155                 160

Glu Asn Phe Ile Arg Phe Ser Lys Ser Leu Gly Leu Pro Glu Asn His
                165                 170                 175
```

-continued

```
Ile Val Phe Pro Val Pro Ile Asp Gln Cys Ile Asp Gly Ser Ala Trp
            180                 185                 190

Ser His Pro Gln Phe
        195
```

HUMAN NEUTROPHIL GELATINASE-ASSOCIATED LIPOCALIN (HNGAL) MUTEINS THAT BIND HEPCIDIN AND NUCLEIC ACID ENCODING SUCH

CROSS-REFERENCE TO RELATED APPLICATIONS

This application is a National Stage application of PCT/EP2011/064085, filed Aug. 16, 2011, which claims priority from U.S. Provisional Application No. 61/374,199, filed Aug. 16, 2010.

The instant application contains a Sequence Listing which has been submitted in ASCII format via EFS-WEB and is hereby incorporated by reference in its entirety. Said ASCII copy, created on Feb. 7, 2013, is named sequence.txt and is 51 KB.

SEQUENCE LISTING

The instant application contains a Sequence Listing which has been submitted in ASCII format via EFS-WEB and is hereby incorporated by reference in its entirety. Said ASCII copy, created on Oct. 31, 2014 is named 029029-0142 SL.txt and is 70,879 bytes in size.

BACKGROUND

Hepcidin, a peptide hormone typically existing in two forms made of either 20 or 25 amino acids, is expressed and secreted by a number of cells in response to iron loading and inflammation. Hepcidin is produced predominantly in hepatocytes of the liver, plays a central role in the regulation of iron homeostasis, acts as an antimicrobial peptide and is directly or indirectly involved in the development of most iron-deficiency/overload syndromes. A major action of hepcidin is to internalize and degrade the iron exporter ferroportin, which is expressed on all iron-exporting cells. Hepcidin directly binds to ferroportin. A high hepcidin level thus leads to the suppression of intestinal iron absorption and iron release from macrophages and hepatocytes, while a low concentration of hepcidin leads to acceleration of iron release from these cells.

Hepcidin is also suspected to play role in pathogenesis of anemia of inflammation and iron-deficiency anemia. Anemia of inflammation, also known as anemia of chronic disease (ACD) or anemia of chronic disorders, currently is the most frequent anemia among hospitalized patients and a common syndrome complicating many infectious, non-infectious inflammatory and neoplastic disorders. ACD is a normocytic, normochromic anemia characterized by decreased iron and iron-binding capacity (transferrin), increased ferritin and the presence of iron in bone marrow macrophages, indicating impaired mobilization of iron from its stores. While in anemia of inflammation hepcidin levels are increased, in iron-deficiency anemia low hepcidin levels are found. Hence, hepcidin could be used as a marker to distinguish these diseases. Hepcidin may also be a useful marker for screening, prognosis and monitoring hereditary hemochromatosis and iron loading anemias. Hepcidin levels may further be useful in monitoring EPO treatment and predicting a response to EPO.

Methods of isolating, analyzing and quantifying hepcidin as well as agents for the treatment of diseases and conditions associated with hepcidin have been described in international patent applications WO 2008/011158, WO 2008/097461, WO 2009/094551A1, WO 2009/139822, WO 2009/058797 and WO 2010/017070. However, no hepcidin-binding protein having the features attendant to the proteins provided by present invention has been previously described.

SUMMARY OF THE INVENTION

One embodiment of the current relates to a lipocalin mutein that is capable of binding hepcidin with an affinity measured by a $K_D$ of about 10 nM or lower. More preferably, the lipocalins can have an affinity measured by a $K_D$ of about 1 nM or lower. In another embodiment, the lipocalin mutein is capable of neutralizing the bioactivity of human hepcidin-25, preferably with an IC50 value of about 80 nM or lower as determined by a cell-based assay for hepcidin-induced internalization and degradation of ferroportin.

In particular embodiments, a lipocalin mutein according to the current invention comprises an amino acid sequence selected from the group consisting of SEQ ID NOs: 1-14. In another embodiment, the mutein has at least 75% identity to the sequence of a wild-type human lipocalin, including human Lipocalin 2.

In another embodiment, the mutein of the current invention is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold. The mutein can be fused at its N-terminus and/or its C-terminus to a fusion partner which is a protein, a protein domain, or a peptide.

In another embodiment, the mutein is conjugated to a compound that extends the serum half-life of the mutein. More preferably, the mutein is conjugated to a compound selected from the group consisting of a polyalkylene glycol molecule, a hydroethylstarch, an Fc part of an immunoglubolin, a $C_H3$ domain of an immoglobulin, a $C_H4$ domain of an immunoglubolin, an albumin binding peptide, and an albumin binding protein.

In another embodiment, the mutein of the current invention is an antagonist of a Hepcidin. The hepcidin can be mature human Hepcidin.

In another embodiment, the current invention relates to a nucleic acid molecule comprising a nucleotide sequence encoding a mutein of the current invention.

In another embodiment, the lipocalin mutein of the current invention is selected from the group consisting of muteins of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (hNGAL), human tear lipocalin (hTLPC), human apolipoprotein D (APO D) and the bilin-binding protein of *Pieris brassicae.*

In another embodiment, the invention relates to a lipocalin mutein which prevents human hepcidin-25 induced reduction of serum iron levels in a subject.

The invention also includes a method of treating a disease or disorder associated with an altered level of a Hepcidin, the method comprising administering a pharmaceutical composition containing a mutein as described herein to a subject in need thereof. In related embodiments, the disease or disorder involves a disorder of iron homeostasis or an inflammatory condition associated with an elevated level of hepcidin.

DESCRIPTION OF FIGURES

FIG. 1 illustrates the PCR assembly strategy for the simultaneous random mutagenesis of the 20 amino acid positions 36, 40, 41, 49, 52, 68, 70, 72, 73, 77, 79 81, 96, 100, 103, 106, 125, 127, 132, and 134 (underlined and numbered) in the amino acid sequence of the mature Lcn 2. These 20 positions were divided into four sequence subsets. For randomization of the amino acids in each subset an oligodeoxynucleotide was synthesized (SEQ ID NO: 16, SEQ ID NO: 39, SEQ ID NO: 18, SEQ ID NO: 19) wherein NNK mixtures of the nucleotides were employed at the mutated codons. N means a mixture of all four bases A, C, G, and T while K means a mixture of only the two bases G and T; hence such a triplet encodes all 20 natural amino acids as well as the amber stop codon TAG, which is translated as glutamine in the *E. coli* supE-strains XL1-blue (Bullock et al., BioTechniques 5 (1987), 376-378) or TG1 (Sambrook et al., Molecular Cloning. A Laboratory Manual (1989), Cold Spring Harbor Press) that were used for phagemid production and gene expression. Four additional oligodeoxynucleotides (SEQ ID NO: 40, SEQ ID NO: 21, SEQ ID NO: 22, SEQ ID NO: 41) with fixed nucleotide sequences corresponding to the non-coding strand (written below the DNA double strand sequence in 3'-5' direction) and filling the gaps between the aforementioned oligodeoxynucleotides were also used in the assembly reaction. Two shorter flanking oligodeoxynucleotides (SEQ ID NO: 24 and SEQ ID NO: 25), which were added in excess and carried biotin groups, served as primers for the PCR amplification of the assembled, entirely synthetic gene fragment. The two flanking primers each encompassed a BstXI restriction site (CCANNNNNNTGG) (SEQ ID NO: 36), giving rise to mutually non-compatible overhangs upon enzyme digestion. This special arrangement of restriction sites enabled a particularly efficient ligation and cloning of the synthetic gene. Substitution of the amino acid Gln28 to His with respect to the original Lcn2 sequence was necessary to introduce the first BstXI site, while the second one naturally occurs in the cDNA of Lcn2. Furthermore, the unpaired residue Cys87 was replaced by Ser during the gene assembly. After one pot PCR the resulting gene fragment was inserted into a vector providing the missing parts of the Lcn2 structural gene. This illustration also depicts two short primers (SEQ ID NO: 32 and SEQ ID NO: 33) upstream and downstream, respectively, of the cassette flanked by the two BstXI restriction sites, which served for double stranded DNA sequencing. Figure discloses full-length DNA sequences as SEQ ID NOS 42 and 44, respectively, in order of appearance and discloses protein sequence as SEQ ID NO: 43.

FIG. 2 illustrates the nucleotide sequence of a library of synthetic Lcn2 genes (only the central cassette flanked by the two BstXI restriction sites, as in FIG. 1, is shown). This gene fragment was prepared by Sloning BioTechnology GmbH. Compared with the DNA library described in FIG. 1 there are two differences. First, whenever possible, codons optimized for *E. coli* expression were used throughout for the non-mutated amino acid positions. Second, a mixture of 19 different triplets (GAC, TTC, CTG, CAC, AAT, AGC, ACC, GCA, ATG, CCT, GTT, TGG, GAG, CAA, ATC, GGA, CGT, GCA, TAC), each encoding a different amino acid except Cys, was employed at the 20 randomized positions, which are identical to the ones depicted in FIG. 1 . Numbering of amino acids corresponds here to an internal scheme employed by Sloning BioTechnology GmbH, whereby Gly No. 1 is the first amino acid codon directly following the upstream BstX1 restriction site. Figure discloses full-length DNA sequences as SEQ ID NOS 45 and 47, respectively, in order of appearance and discloses protein sequence as SEQ ID NO: 46.

FIG. 3A-3H depicts an alignment of certain amino acid sequences of hHepcidin-specific, NGAL-based lipocalin muteins in comparison with the polypeptide sequence of wildtype NGAL lipocalin. The NGAL-derived, hepdicin binding muteins comprise residues 1 to 178, meaning they have the length of the mature wildtype proteins. Residues 179 to 186 are the sequence of a streptavidin binding tag, Strep-tag™, used in the isolation of generated muteins.

FIG. 4A depicts the amino acid sequence of the lipocalin mutein of SEQ ID NO: 1 fused, via a linker (greyish bold italic) to an ABD domain (bold) and a streptavidin binding tag, Strep-tag™ (italic) (SEQ ID NO: 15).

FIG. 4B depicts the amino acid sequence of the lipocalin hNGAL (SEQ ID NO: 48), as encoded by the vector phNGAL 98, fused to a streptavidin binding tag, the Strep-tag™ (italic) and an N-terminal T7 tag (bold italic) (SEQ ID NO: 34). This polypeptide is encoded by phNGAL 101.

FIG. 5 shows the results of a direct ELISA of selected Lcn2 muteins.

FIG. 6 depicts the results of a competitive binding assay of selected Lcn2 muteins.

FIG. 7 depicts the affinities of selected muteins for human and cynomolgus Hepcidin-25 as determined by surface-plasmon-resonance (SPR).

FIG. 8 depicts the in vitro neutralization activity of anti-Hepcidin-25 lipocalin muteins.

FIG. 10 depicts pharmacokinetic parameters for SEQ ID NO: 14-PEG and SEQ ID NO: 1-ABD (equal to SEQ ID NO: 15).

DETAILED DESCRIPTION OF THE INVENTION

Figure 9:
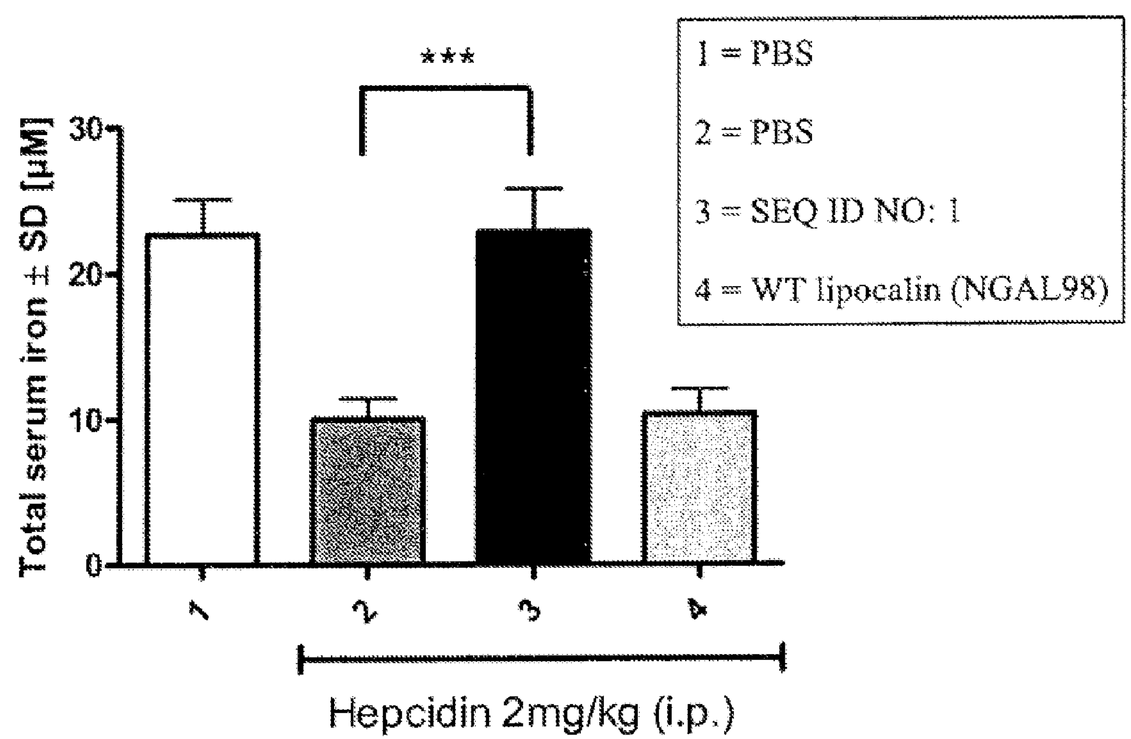
FIG. 9 demonstrates that a lipocalin mutein directed against hepcidin neutralizes human hepcidin injected into mice.

In one aspect, the present invention relates to novel, specific-binding proteins directed against or specific for hepcidin. Proteins of the invention may be used for therapeutic and/or diagnostic purposes. As used herein, a protein of the invention "specifically binds" a target (here, hepcidin) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

Proteins of the invention, which are directed against or specific for hepcidin, include any number of specific-binding protein muteins that are based on a defined protein scaffold. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold.

A protein of the invention can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). As used herein, a "lipocalin" is defined as monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

In a preferred embodiment, a protein of the invention is a mutein of Lipocalin 2 (Lcn 2; also known as human neutrophil gelatinase-associated lipocalin, hNGAL, or as siderocalin). The term "human neutrophil gelatinase-associated lipocalin" or "hNGAL" or "lipocalin 2" or "Lcn2" as used herein to refer to the mature hNGAL with the SWISS-PROT/UniProt Data Bank Accession Number P80188 or the mature hNGAL shown in SEQ ID NO:35. The mature form of this protein has amino acids 21 to 198 of the complete sequence, since a signal peptide of amino acids 1-20 is cleaved off. The protein further has a disulfide bond formed between the amino acid residues at positions 76 and 175 of the mature protein.

In a more preferred embodiment, the invention relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind a hepcidin as given non-natural target with detectable affinity. Preferably, said lipocalin mutein has one or more such as 1, 2, 3, 4, 6, 7, 8, 9, 10, 11, 12, 13, 14, 15, 16, 17, 18, 19 or 20 amino acid replacements at a position corresponding to position 36, 40, 41, 49, 52, 68, 70, 72, 73, 77, 79, 81, 96, 100, 103, 106, 125, 127, 132, and/or 134 of the linear polypeptide sequence of NGAL.

In this context, the inventors identified a specific group of Lipocalin 2 muteins with mutations at specific positions which show detectable affinity as well as specificity for Hepcidin. Suitable amino acid positions for mutation include sequence positions 96, 100, and 106, of the linear polypeptide sequence of human Lipocalin 2. The present invention also relates to nucleic acids encoding these proteins.

Other protein scaffolds that can be engineered in accordance with the present invention to provide protein muteins that bind hepcidin with detectable affinity include: an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J. 13:5303-9 (1994)), "Diabodies" (Holliger et al. "'Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer WP 2005, Nat Biotech, December; 23(12):1556-61, E-Publication in Nat. Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

A protein of the invention may include the wild type (natural) amino acid sequence of the "parental" protein scaffold (such as a lipocalin) outside the mutated amino acid sequence positions; alternatively, a lipocalin mutein may also contain amino acid mutations outside the sequence positions subjected to mutagenesis that do not interfere with the binding activity and the folding of the mutein. Such mutations can be accomplished on a DNA level using established standard methods (Sambrook, J. et al. (1989) *Molecular Cloning: A Laboratory Manual,* 2nd Ed., Cold Spring Harbor Laboratory Press, Cold Spring Harbor, N.Y.). Possible alterations of the amino acid sequence are insertions or deletions as well as amino acid substitutions.

Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled worker.

The skilled worker will appreciate methods useful to prepare protein muteins contemplated by the present invention but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the invention also includes functional variants of proteins disclosed herein, which have a threshold sequence identity or sequence homology to a reference protein. By "identity" or "sequence identity" is meant a property of sequences that measures their similarity or relationship. The term "sequence identity" or "identity" as used in the present invention means the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins. Most preferred, the amino acid sequence shown in SEQ ID NO:35 is preferred as a "reference sequence". SEQ ID NO:35 shows the mature hNGAL. The term "reference sequence" and "wild type sequence" (of NGAL) is used interchangeably herein. Alternatively, the amino acid sequence with the SWISS-PROT/UniProt Data Bank Accession Number P80188 can be used as reference sequence.

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

It is also possible to deliberately mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages. With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of hNGAL. In some embodiments where a human Lipocalin 2 mutein of the invention has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein.

The term "position" when used in accordance with the invention means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the invention which may be substituted may very due to deletion or addition of amino acids elsewhere in a (mutant or wild-type) lipocalin. Similarly, the position of a given nucleotide in accordance with the present invention which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the invention it is preferably to be understood that nucleotides/amino acids may differ in the indicated number but may still have similar neighboring nucleotides/amino acids. Said nucleotides/amino acids which may be exchanged, deleted or added are also comprised by the term "corresponding position". When used herein "at a position corresponding to a position" a position in a "query" amino acid (or nucleotide) sequence is meant that corresponds to a position in a "subject" amino acid (or nucleotide) sequence.

Specifically, in order to determine whether a nucleotide residue or amino acid residue of the amino acid sequence of a lipocalin different from a NGAL lipocalin mutein of the invention corresponds to a certain position in the nucleotide sequence or the amino acid sequence of a NGAL lipocalin mutein as described, in particular any of SEQ ID NOs: 1-14 or that having one or more amino acid substitutions such as 2, 3, 4, 5, 6, 7, 8, 9, 10, 11, 12, 13, 14, 15, 16, 17, 18, 19 or 20 at position 36, 40, 41, 49, 52, 68, 70, 72, 73, 77, 79, 81, 96, 100, 103, 106, 125, 127, 132, and/or 134 of the linear polypeptide sequence of NGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a lipocalin mutein of any of SEQ ID Nos: 1-14 or that having one or more amino acid substitutions such as 2, 3, 4, 5, 6, 7, 8, 9, 10, 11, 12, 13, 14, 15, 16, 17, 18, 19 or 20 at position 36, 40, 41, 49, 52, 68, 70, 72, 73, 77, 79, 81, 96, 100, 103, 106, 125, 127, 132, and/or 134 or any other position described herein of the linear polypeptide sequence of NGAL can serve as "subject sequence", while the amino acid sequence of a lipocalin different from NGAL serves as "query sequence".

Given the above, a skilled artisan is thus readily in a position to determine which amino acid position mutated in Lcn2 as described herein corresponds to an amino acid of a scaffold other than Lcn2, preferably such as one of those described herein. Specifically, a skilled artisan can align the amino acid sequence of a mutein as described herein, in particular a NGAL mutein (or anticalin) of the invention with the amino acid sequence of a different lipocalin to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position(s) 36, 40, 41, 49, 52, 68, 70, 72, 73, 77, 79, 81, 96, 100, 103, 106, 125, 127, 132, and/or 134 or to an amino acid at any other position as described herein of the linear polypeptide sequence of NGAL.

Proteins of the invention, which are directed against or specific for hepcidin, include any number of specific-binding protein muteins that are based on a defined protein scaffold. Preferably, the scaffold is hNGAL. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50. However, it is preferred that a mutein of the invention is still capable of binding hepcidin.

In some embodiments, a protein according to the invention binds a hepcidin with a $K_D$ of 100 μM or less, including 5 μM or less, about 500 nM, about 200 nM or less, 100 nM or less, 1 nM or less, or 0.1 nM or less. A protein of the invention may specifically bind one or more continuous, discontinuous or conformation epitope(s) of the mature, folded bioactive form of a hepcidin.

A protein of the invention is able to bind a hepcidin with detectable affinity, i.e. with a dissociation constant of at least 200 nM, i.e. $K_D$ of about 200 nM or less. In some embodiments, a protein of the invention binds a hepcidin with a dissociation constant of at least about 100 nM, about 50 nM, about 25 nM, about 15 nM, about 5 nM, about 2 nM, about 0.5 nM, about 0.25 nM, about 0.1 nM, about 0.05 nM or even less. A protein of the invention preferably binds to a mature human hepcidin molecule with an affinity by a $K_D$ of about 10 nM or stronger. Binding affinities have been found by the present inventors to often be of a $K_D$ below about 1 nM and, in some cases, about 0.1 nM and below.

The binding affinity of a protein of the invention (e.g. a mutein of a lipocalin) to a selected target (in the present case, hepcidin), can be measured (and thereby $K_D$ values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

The amino acid sequence of a protein of the invention may have a high sequence identity to mature human Lipocalin 2 or other lipocalins. In this context, a protein of the invention may have at least 70%, at least 75%, at least 80%, at least 82%, at least 85%, at least 87%, at least 90% identity, including at least 95% identity to a protein selected from the group consisting of the sequence of SEQ ID NOS: 1-14. It is preferred that a structural homolog has still an amino acid replacement at one or more such as 2, 3, 4, 5, 6, 7, 8, 9, 10, 11, 12, 13, 14, 15, 16, 17, 18, 19 or 20 positions corresponding to position 36, 40, 41, 49, 52, 68, 70, 72, 73, 77, 79, 81, 96, 100, 103, 106, 125, 127, 132, and/or 134 of the linear polypeptide sequence of NGAL.

The invention also includes structural homologues of the proteins selected from the group consisting of the sequence of SEQ ID NOS: 1-14, which have an amino acid sequence homology or sequence identity of more than about 60%, preferably more than 65%, more than 70%, more than 75%, more than 80%, more than 85%, more than 90%, more than 92% and most preferably more than 95% in relation thereto. It is preferred that a structural homolog has still an amino acid replacement at one or more such as 2, 3, 4, 5, 6, 7, 8, 9, 10, 11, 12, 13, 14, 15, 16, 17, 18, 19 or 20 positions corresponding to position 36, 40, 41, 49, 52, 68, 70, 72, 73, 77, 79, 81, 96, 100, 103, 106, 125, 127, 132, and/or 134 of the linear polypeptide sequence of NGAL.

The term "hepcidin" refers to the protein also termed liver-expressed antimicrobial peptide 1 or putative liver tumor regressor, of which the human form has the UniProtKB/Swiss-Prot accession number P81172. On a general basis the term "hepcidin" refers to any form of the hepcidin protein known to be present in vertebrate species, including in mammals The human unprocessed protein has a length of 84 amino acids and is encoded by the gene "HAMP," also known as "HEPC" or "LEAP1." It is cleaved into two chains, which are herein also included in the term "Hepcidin." These two chains are of amino acids 60-84, which is Hepcidin-25 (Hepc25) and of amino acids 65-84, which is Hepcidin-20 (Hepc20). Hepcidin-25 is arranged in the form of a bent hairpin, stabilized by four disulfide bonds. Natural variants also included in the term "hepcidin" have, for example, the amino acid replacement 59 R→G (VAR_0425129); the amino acid replacement 70 C→R (VAR_042513); the amino acid replacement 71 G→D (VAR_026648) or the amino acid replacement 78 C→Y (VAR_042514). A further natural variant is Hepcidin-22, another N-terminally truncated isoform (besides Hecidin-20) of Hepcidin-25.

The term "mature hepcidin" as used herein refers to any mature, bioactive form of the hepcidin protein expressed in a vertebrate such as a mammal. The term "human hepcidin" refers to any form of the hepcidin protein present in humans. The expression "human hepcidin-25" refers to the mature form of human hepcidin with the amino acid sequence as depicted in SEQ ID NO: 28. In the present invention lipocalin muteins are provided that are able to bind each given form of hepcidin including proteolytic fragments thereof, regardless of whether the respective hepcidin molecule displays biological/physiological activity. Thus, the hepcidin molecule may only be present in a biological sample, without having any measurable physiological relevance. See, for example, Hepcidin-22 that so far has only been detected in urine found in urine and that so far is assumed to merely be a urinary degradation product of Hepcidin-25 (reviewed in Kemna et al., Haematologica. 2008 Jan.; 93:$(1)_{9\text{-}0}$-97). A mutein of the invention may of course also bind physiological active species such as the mature, bioactive Hepcidin-25. Accordingly, a mutein of the invention may be used as diagnostic and/or pharmaceutical, depending on the hepcidin form chosen to be recognized.

In line with the above, a protein of the invention preferably acts as an antagonist of a hepcidin molecule. In some embodiments, a protein of the invention (e.g., a human Lipocalin 2 mutein) may act as an antagonist of a hepcidin molecule by inhibiting the ability of the hepcidin molecule to bind to or otherwise interact with ferroportin. The hepcidin may be a mature human hepcidin format such as hepcidin-25 or hepcidin-20. Binding of a mature hepcidin to ferroportin leads to internalization and degradation of ferroportin, standard processes of a protein with a cell surface/membrane location.

In yet another aspect, the present invention includes various lipocalin muteins, including muteins of human Lipocalin 2 that specifically bind hepcidin. In this sense, hepcidin can be regarded a non-natural ligand of wild type human Lipocalin 2, where "non-natural ligand" refers to a compound that does not bind to wildtype lipocalins, including human Lipocalin 2 under physiological conditions. By engineering wildtype lipocalins such as human Lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, 11, 12, 13, 14, 15, 16, 17, 18, 19, and/or 20 nucleotide triplet(s) encoding for any of the sequence positions 36, 40, 41, 49, 52, 68, 70, 72, 73, 77, 79, 81, 96, 100, 103, 106, 125, 127, 132, and/or 134 of the linear polypeptide sequence of hLcn2, or other parallel sites on lipocalins, a random mutagenesis can be carried out by allowing substitution at this positions by a subset of nucleotide triplets.

The amino acid replacements in the lipocalin muteins of the invention as described herein are preferably within one, two, three or four loop regions of a lipocalin, preferably hNGAL. The loop regions are from positions 33 to 54 (loop 1), 66 to 83 (loop 2), 94 to 106 (loop 3), and 123 to 136 (loop 4) of hNGAL. 24-36, 53-66, 79-84, and 103-110

Further, the lipocalins can be used to generate muteins that have a mutated amino acid residue at any one or more, including at least at any two or all three, of the sequence positions of the sequence positions corresponding to the sequence positions 96, 100 and 106 of the linear polypeptide sequence of a mature human Lipocalin 2. A substitution at sequence position 96 may for example be a substitution Asn 96→Arg, Asp, Gln, Gly, Lys, Ser, Thr or Val. A substitution at sequence position 100 may for example be a substitution Tyr 100→Ala, Arg, Glu, Gln, Gly, Ser and Val. A substitution at sequence position 106 may for example be a substitution Tyr 106→Ile, Gly, Phe, Val or Arg. A mutein of the invention may in some embodiments have the set of amino acid substitutions, relative to the linear polypeptide sequence of a mature human Lipocalin 2, of Asn 96→Val, and Tyr 100→Gln. In such an embodiment the tyrosine at position 106 may be unchanged. A mutein of the invention may in some embodiments have the set of amino acid substitutions, relative to the linear polypeptide sequence of a mature human Lipocalin 2, of Asn 96→Arg, Tyr 100→Glu, and Tyr 106→Phe. In some embodiments a mutein of the invention may have the set of amino acid substitutions of Asn 96→Asp, Tyr 100→Ser and Tyr 106→Gly. A mutein of the invention may in some embodiments have the set of amino acid substitutions of Asn 96→Gly, Tyr 100→Gly and Tyr 106→Gly. A mutein of the invention may in some embodiments have the set of amino acid substitutions of Asn 96→Lys, Tyr 100→Ala and Tyr 106→Ile. In some embodiments a mutein of the invention may have the set of amino acid substitutions of Asn 96→Ser, Tyr 100→Arg and Tyr 106→Val. A mutein of the invention may in some embodiments have the set of amino acid substitutions of Asn 96→Ser, Tyr 100→Val and Tyr 106→Arg. In some embodiments a mutein of the invention may have the set of amino acid substitutions of Asn 96→Thr, Tyr 100→Val and Tyr 106→Gly. In some embodiments a mutein of the present invention further includes a mutated amino acid residue at position 134 within the linear polypeptide sequence of the mature human Lipocalin 2. In one embodiment this substitution is Lys 134→Trp.

In some embodiments, a mutein of the present invention includes, typically in addition to a mutation at one or more of sequence positions 96, 100 and 106 (supra), a mutated amino acid residue at any one or more of the sequence positions corresponding to the sequence positions 52, 68, 81, 127 of the linear polypeptide sequence of the mature human Lipocalin 2. The mutein may, for instance, include within the linear polypeptide sequence of the mature human Lipocalin 2, a substitution Tyr 52→His, Leu, Phe or Trp. The mutein may also include within the linear polypeptide sequence of the mature human Lipocalin 2 a substitution Ser 68→Arg, Gly or Ile. The mutein may also include a substitution Arg 81-Glu, Gly or Gln. The mutein may, for instance, include within the linear polypeptide sequence of the mature human Lipocalin 2 a substitution Ser 127→Thr or Trp. A mutein of the invention may in some embodiments have the set of amino acid substitutions, relative to the linear polypeptide sequence of a mature human Lipocalin 2, of Tyr 52→His, Ser 68→Arg, Arg 81→Ser and Ser 127→Trp. In some embodiments a mutein of the invention may have the set of amino acid substitutions of Tyr 52→Leu, Ser 68→Arg, Arg 81→Glu and Ser 127→Trp. A mutein of the invention may in some embodiments have the set of amino acid substitutions of Tyr 52→Phe, Ser 68→Gly, Arg 81→Gly and Ser 127→Trp. A mutein of the invention may in some embodiments have the set of amino acid substitutions of Tyr 52→Trp, Ser 68→Ile, Arg 81→Gln and Ser 127→Trp. In some embodiments a mutein of the invention may have the set of amino acid substitutions of Tyr 52→Trp, Ser 68→Arg, Arg 81→Glu and Ser 127→Trp. A mutein of the invention may in some embodiments have the set of amino acid substitutions, in relation to the sequence of a mature human Lipocalin 2, of Tyr 52→Trp, Ser 68→Arg, Arg 81→Glu and Ser 127→Thr. In some embodiments a mutein of the invention may have the set of amino acid substitutions of Tyr 52→Trp, Ser 68→Arg, Arg 81→Glu and Ser 127→Trp.

In a further embodiment of the invention, the mutein includes at least 1, 2, 3, 4, 5, 6, 7, 8, 9, 10, 11, 12, 13, 14, 15, 16, 17, 18, 19 or 20 mutated amino acid residues at any of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL or the corresponding sites on other lipocalins. In a further embodiment, the mutein includes at least 2, 3, 4, 5, 6, 7, 8, 9, 10, 11, 12, 13, 14, 15, 16, 17, 18, 19, or 20 mutated amino acid residues at any one of the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL or the corresponding sites on other lipocalins. In still a further embodiment, the mutein includes 18, 19 or 20 mutated amino acid residues at any one of the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of human Lipocalin 2 or the corresponding sites on other lipocalins.

A mutein of the invention may, for example, with respect to the mature hLcn2 wild type amino acid sequence, include one or more amino acid replacements such as 2, 3, 4, 5, 6, 7, 8, 9, 10, 11, 12, 13, 14, 15, 16, 17, 18, 19 or 20 of the group: Leu36→Ala, Cys, Thr, Val; Ala 40→Arg, Glu, Gly and Ser; Ile 41→Ile, Leu, Met or Val; Gln 49→Leu or Met; Leu 70→Asp, Asn, Gln, Met or Phe; Arg 72→Glu, Gly, Leu or Val; Lys 73→Ala, Arg, Glu, Gly, Leu, Thr or Tyr; Asp 77→Arg, Glu, Gly, Leu, Ser or Val; Trp 79→Gly, Leu, Ser, Tyr or Val; Leu 103→Ala, Arg, Gly or Trp; Tyr 106→Gly, Ile, Phe or Val; Lys 125→Arg, Leu, Met, Phe, Thr, or Val; and Tyr 132→Leu or Val. A mutein of the invention may, for instance, have the set of amino acid combinations, in relation to the linear polypeptide sequence of a mature human Lipocalin 2, of Ala 36, Ser 40, Leu 41, Met 49, Asn 70, Gly 72, Gly 73, Ser 77, Leu 79, Leu 125 and Val 132. A mutein of the invention may, for example, have the set of amino acid combinations, in relation to the sequence of a mature human Lipocalin 2, of Leu 36, Arg 40, Val 41, Gln 49, Asp 70, Arg 72, Thr 73, Leu 77, Ser 79, Thr 125 and Val 132. In some embodiments a mutein of the invention may have the set of amino acid combinations of Leu 36, Glu 40, Ile 41, Leu 49, Gln 70, Gly 72, Glu 73, Gly 77, Gly 79, Phe 125 and Val 132. A mutein of the invention may also have the set of amino acid combinations of Leu 36, Glu 40, Ile 41, Met 49, Met 70, Leu 72, Ala 73, Glu 77, Leu 79, Val 125, Val 132 or the set of amino acid combinations of Leu 36, Glu 40, Val 41, Met 49, Met 70, Leu 72, Ala 73, Glu 77, Leu 79, Thr 125 and Val 132. In some embodiments a mutein of the invention may have the set of amino acid combinations of Leu 36, Glu 40, Val 41, Met 49, Met 70, Leu 72, Ala 73, Glu 77, Leu 79, Val 125 and Val 132 or the set of amino acid combinations of Thr 36, Ser 40, Ile 41, Gln 49, Phe 70, Glu 72, Gly 73, Arg 77, Val 79, Val 125 and Leu 132. As a further example, a mutein of the invention may have the set of amino acid combinations of Val 36, Glu 40, Met 41, Leu 49, Met 70, Glu 72, Tyr 73, Val 77, Leu 79, Arg 125 and Val 132. A mutein of the invention may also have the set of amino acid combinations of Val 36, Gly 40, Leu 41, Leu 49, Leu 70, Val 72, Arg 73, Arg 77, Tyr 79, Met 125 and Val 132.

In one embodiment of the present invention, the mutein includes mutated amino acid residues at at least any 10, 14, 15, 20, 22, 24, 26, 28, 29, 30, 31, 32, 33, 35 or all 45 of the above-listed sequence positions.

A mutein of the invention, which binds to Hepcidin, can include with respect to the mature human Lipocalin 2 wild type amino acid sequence (Lcn2) at least 2, 3, 4, 5, 6, 7, 8, 9, 10, 11, 12, 13, 14, 15, 16 or 17 amino acid replacements which include, but are not limited to, Leu36—Val or Cys; Ala40→Tyr or Lys or Val; Ile41→Thr or Ser or Leu; Gln49→Leu or Trp; Leu70→Gly; Arg72→Gly or Asp; Lys73→Leu or Thr or Asp; Asp77→Asn or His or Leu; Trp79→Lys; Asn96→Ile or Arg; Tyr100→Gln or Arg or Glu; Leu103→Met or Arg or Gly; Tyr106→Tyr or Ala or Trp; Lys125→Thr or Val or Glu; Ser127→Gly or Gln or Ala; Tyr132→Met or Ser or Thr; and Lys134→Asn In one embodiment, a mutein of the invention, which binds to Hepcidin includes the following amino acid replacements: Leu36→Val; Ala40→Tyr; Ile41→Thr; Gln49→Leu; Leu70→Gly; Lys73→Leu; Asp77→Asn; Trp79→Lys; Asn96→Ile; Tyr100→Gln; Leu103→Met; Lys125→Thr; Ser127→Gly; Tyr132→Met; and Lys134→Asn. In a further embodiment, a mutein of the invention, which binds to Hepcidin, includes the following amino acid replacements Leu36→Val; Ala40→Lys; Ile41→Ser; Gln49→Trp; Leu70→Gly; Arg72→Gly; Lys73→Thr; Asp77→His; Trp79→Lys; Asn96→Arg; Tyr100→Arg; Leu103→Arg; Tyr106→Ala; Lys125→Val; Ser127→Gln; Tyr132→Ser; and Lys134→Asn. In another embodiment, a mutein of the invention, which binds to Hepcidin, includes the following amino acid replacements Leu36→Cys; Ala40→Val; Ile41→Leu; Gln49→Leu; Leu70→Gly; Arg72→Asp; Lys73→Asp; Asp77→Leu; Trp79→Lys; Asn96→Arg; Tyr100→Glu; Leu103→Gly; Tyr106→Trp; Lys125→Glu; Ser127→Ala; Tyr132→Thr; and Lys134→Asn.

A mutein according to the present invention may further include, with respect to the mature hLcn2 wild type amino acid sequence, the amino acid replacement Gln 28→His. A mutein according to the invention may also include, relative to the mature hLcn2 wild type amino acid sequence, the amino acid replacement Lys 62→Arg. Further, a mutein according to the present invention may include, relative to the mature hLcn2 wild type amino acid sequence, the amino acid replacement Phe 71→Pro or Ser. A further amino acid replacement that may be present in a mutein of the present invention, relative to the mature hLcn2 wild type amino acid sequence, is the replacement Lys 74→Glu. Yet a further amino acid replacement that may be included in a mutein of the invention is the replacement Lys 75→Glu. A mutein of the invention may also include, with respect to the mature hLcn2 wild type amino acid sequence, the amino acid replacement Cys 87→Ser. A mutein of the invention may also include the amino acid replacement Ser 146→Pro. A further amino acid replacement that may be present in a mutein of the present invention, relative to the mature hLcn2 wild type amino acid sequence, is the replacement Glu 147→Gly. A mutein of the invention may include further amino acid replacements. The muteins can further include amino acid replacements, such as Tyr52→Gln or Val; Ser68→Lys or Asn; or Arg81→Trp, Asn or His.

A mutein of the invention typically exists as monomeric protein. However, it is also possible that a lipocalin mutein of the invention is able to spontaneously dimerise or oligomerise. Although the use of lipocalin muteins that form stable monomers may be preferred for some applications, e.g. because of faster diffusion and better tissue penetration, the use of lipocalin muteins that form stable homodimers or multimers may be advantageous in other instances, since such multimers can provide for a (further) increased affinity and/or avidity to a given target. Furthermore, oligomeric forms of the lipocalin mutein may have slower dissociation rates or prolonged serum half-life.

It is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

In one embodiment, the muteins disclosed herein can be linked, either N- or C-terminal to an affinity tag such as pentahistidine tag (SEQ ID NO: 37), a hexahistidine tag (SEQ ID NO: 38) or a steptavidin tag (e.g. Streptae®). Thus, the present application encompasses also all explicitly and generic described muteins equipped with such tags.

The term "fragment" as used in the present invention in connection with the feature lipocalin mutein fragment relates to proteins or peptides derived from full-length mature Lcn 2 that are N-terminally and/or C-terminally shortened, i.e. lacking at least one of the N-terminal and/or C-terminal amino acids. Such fragments include preferably at least 10, more preferably 20, most preferably 30 or more consecutive amino acids of the primary sequence of mature Lcn 2 and are usually detectable in an immunoassay of mature Lcn 2. The word "detect" or "detecting" as used herein is understood both on a quantitative and a qualitative level, as well as a combination thereof. It thus includes quantitative, semi-quantitative and qualitative measurements of a molecule of interest. Accordingly, the presence or absence of a molecule such as a hepcidin, e.g. in a sample, as well as its concentration or level may be determined.

Also included in the scope of the present invention are the above muteins, which have been altered with respect to their immunogenicity, to reduce any detected immunogenicity by employing methods known to the skilled worker in the field.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. To reduce the immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class 1 molecules (Altuvia et al. (1995) *J. Mol. Biol.* 249: 244-250). Such an approach may also be utilized to identify potential T-cell epitopes in the muteins of the invention and to make, depending on its intended use, a selection of a specific mutein on the basis of its predicted immunogenicity. It may be furthermore possible to subject peptide regions that have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19(6):463-471) and may be adapted to the muteins of the present invention. The muteins thus obtained may possess a minimized immunogenicity, which is desirable for their use in therapeutic and diagnostic applications, such as those described below.

For some applications, it is also useful to employ the muteins of the invention in a conjugated form. Accordingly, the invention is also directed to lipocalin muteins which are conjugated to a compound which can include, but is not limited to organic molecules, an enzyme label, a colored label, a cytostatic agent, a toxin, a label that can be photoactivated and which is suitable for use in photodynamic therapy, a fluorescent label, a radioactive label, a chromogenic label, a luminescent label, metal complexes, metal, such as colloidal gold, haptens, digoxigenin, biotin, a chemotherapeutic metal, or a chemotherapeutic metal, to name only a few evocative examples. The mutein may also be conjugated to an organic drug molecule. The conjugation can be carried out using any conventional coupling method known in the art.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

In general, it is possible to label a lipocalin mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al. (2005) *International Congress Series*. 1277,185-198 or Gaillard P J, et al. (2005) *Expert Opin Drug Deliv.* 2(2), 299-309). Such compounds are for example available under the trade name 2B-Trans™ (to-BBB technologies BV, Leiden, NL). Other exemplary targeting molecules to which the muteins of the present invention may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of the invention may in some embodiments be conjugated to a compound that extends the serum half-life of the mutein (in this regard see also PCT publication WO 2006/56464 where such conjugation strategies are described with references to muteins of human neutrophil gelatinase-associated lipocalin with binding affinity for CTLA-4). The compound that extends the serum half-life may be a polyalkylene glycol molecule, such as polyethylene (PEG) or an activated derivative thereof; hydroxyethyl starch, fatty acid molecules, such as palmitic acid (Vajo & Duckworth (2000) *Pharmacol. Rev.* 52, 1-9), an Fc part of an immunoglobulin, a $C_H3$ domain of an immunoglobulin, a $C_H4$ domain of an immunoglobulin, albumin or a fragment thereof, an albumin binding peptide, an albumin binding protein, transferrin, or the tag Pro-Ala-Ser, to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation compounds for extending the half-life of a lipocalin mutein of the invention include albumin (Osborn et al. (2002) *J. Pharmacol. Exp. Ther.* 303, 540-548), or an albumin binding protein, for example, a bacterial albumin binding domain, such as the one of streptococcal protein G (König, T. and Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

In other embodiments, albumin itself or a biological active fragment of albumin can be used as compound of a lipocalin mutein of the invention that extends the serum half-life of the mutein. The term "albumin" includes all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example comprise two copies of the mutein linked to the Fc region of an antibody to improve pharmacokinetics, solubility, and production efficiency.

Yet another alternative to prolong the half-life of a mutein of the invention is to fuse the N- or C-terminus of a mutein of the invention to long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as compound that extends the half-life of the mutein, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) "The Clinical Efficacy of Poly(Ethylene Glycol)-Modified Proteins" J. Control. Release 11, 139-148). The molecular weight of such a polymer, preferrably polyethylene glycol, may range from about 300 to about 70.000 Dalton, including, for example, polyethylene glycol with a molecular weight of about 10.000, of about 20.000, of about 30.000 or of about 40.000 Dalton. Moreover, e.g. as described in U.S. Pat. No. 6,500,930 or 6,620,413, carbohydrate oligo- and polymers such as starch or hydroxyethyl starch (HES) can be conjugated to a mutein of the invention for the purpose of serum half-life extension.

In another embodiment, in order to provide suitable amino acid side chains for conjugating one of the above compounds to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein, it may be advantageous to use them in the form of fusion proteins. In some embodiments, the inventive mutein is fused at its N-terminus and/or it's C-terminus to a protein, a protein domain or a peptide such as a signal sequence and/or an affinity tag.

For pharmaceutical applications, a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugated compounds described above, the fusion partner may be an Fc part of an immunoglobulin, a $C_H3$ domain of an immunoglobulin, a $C_H4$ domain of an immunogloubulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra J. Pharmacol. Exp. Ther. 303, 540-548), or an albumin binding protein, for example, a bacterial albumin binding domain, such as streptococcal protein G (König, T. and Skerra, A. (1998) supra J. Immunol. Methods 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" includes all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-5-transferase, the albumin-binding domain of protein G, protein A, antibody fragments, oligomerization domains, lipocalin muteins of same or different binding specificity (which results in the formation of "duocalins," cf. Schlehuber, S., and Skerra, A. (2001), Duocalins, engineered ligand-binding proteins with dual specificity derived from the lipocalin fold (Biol. Chem. 382, 1335-1342), or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-tag® or Strep-tag® II (Schmidt, T.G.M. et al. (1996) J. Mol. Biol. 255, 753-766), the myc-tag, the FLAG-tag, the His6-tag (SEQ ID NO: 38) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also includes lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra).

Thus, the invention is also directed to a host cell containing a nucleic acid molecule as disclosed herein.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then enriched, purified or isolated from this host organism or its culture. It is also possible to produce a protein in vitro, for example by use of an in vitro translation system. The term "enriched" means that the mutein or a functional fragment thereof constitutes a significantly higher fraction of the total protein present in a sample or solution of interest than in a sample or solution from which it was taken. Enrichment may for instance include the isolation of a certain fraction from a cell extract. This may be obtained by standard techniques such as centrifugation. Examples of other means of enrichment are filtration or dialysis, which may for instance be directed at the removal of undesired molecules below a certain molecular weight, or a precipitation using organic solvents or ammonium sulphate. Purification may for instance include a chromatographic technique, for example gel filtration, ion exchange chromatography, affinity purification, hydrophobic interaction chromatography or hydrophobic charge induction chromatography. Another example for a purification is an electrophoretic technique, such as preparative capillary electrophoresis. Isolation may include the combination of similar methods. As used herein, "substantially pure" or "substantially purified" means a compound or species that is the predominant species present (i.e., on a molar basis it is more abundant than any other individual species in the composition). In some embodiments, a substantially purified composition is a composition in which the species includes at least about 50 percent (on a molar basis) of all molecular or, as applicable, all macromolecular species present. In certain embodiments, a substantially pure composition will have more than about 80%, about 85%, about 90%, about 95%, or about 99% of all molecular or, as applicable, all macromolar species present in the composition.

When producing the mutein in vivo, a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In one aspect, the present invention relates to a method for the generation of a mutein which binds hepcidin, comprising:

subjecting a nucleic acid molecule encoding a lipocalin to mutagenesis, resulting in one or more mutein nucleic acid molecule(s).

The method can further include:

expressing the one more mutein nucleic acid molecule(s) obtained in (a) in a suitable expression system, bringing the plurality of muteins into contact with at least a fragment or a mature form of hepcidin, and enriching the one or more mutein(s) having a detectable binding affinity for a given target by means of selection and/or isolation.

The term "mutagenesis" as used herein means that the experimental conditions are chosen such that the amino acid naturally occurring at a given sequence position of the lipocalin, including Lcn 2 (hNGAL; Swiss-Prot data bank entry P80188) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

In one non-limiting approach, the coding sequence of human Lipocalin 2 can be used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (1989), supra). A commonly used technique is the introduction of mutations by means of PCR (polymerase chain reaction) using mixtures of synthetic oligonucleotides, which bear a degenerate base composition at the desired sequence positions. Other similar techniques are well known to those of skill in the art.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a further embodiment, the method includes subjecting the nucleic acid molecule to mutagenesis at nucleotide triplets coding for at least any 1, 2, 3, 4, 5, 6, 7, 8, 9, 10, 11, 12, 13, 14, 15, 16, 17, 18, 19 or 20 of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and/or 138 of the linear polypeptide sequence of the lipocalin, or, for example, human Lipocalin 2. Such a nucleic acid may subjected to mutagenesis and introduced into a suitable bacterial or eukaryotic host organism by using recombinant DNA technology. Obtaining a nucleic acid library of a lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in their entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, another embodiment of the above methods comprises:

(i) providing at least a fragment of hepcidin as a given target/ligand for example, contacting the plurality of muteins with said target/ligand in order to allow formation of complexes between said ligand and muteins having binding affinity for said target/ligand, and removing muteins having no or no substantial binding affinity.

In one embodiment of the methods of the invention, the selection binding affinity is carried out under competitive conditions. Competitive conditions as used herein means that selection of muteins encompasses at least one step in which the muteins and the fragment of hepcidin or a mature hepcidin such as Hepcidin-25 (target) are brought in contact in the presence of an additional ligand, which competes with binding of the muteins to the target (hepcidin). This additional target may be another form of hepcidin, for example Hepcidin-20 (in case muteins are to be selected that selectively bind Hepcidin-25 or even the five N-terminal residues of Hepcidin-25 (as indicated earlier, it is presently assumed that the iron-regulating bioactivity is almost exclusively due to the 25 amino acid form Hepcidin-25, indicating that the five N-terminal amino acids are essential for this activity, Kenma et al., supra), an excess of the target itself or any other non-physiological ligand of the hepcidin that binds at least an overlapping epitope to the epitope recognized by the muteins of the invention and thus interferes with target (hepcidin) binding of the muteins. Alternatively, the additional ligand competes with binding of the muteins by complexing an epitope distinct from the binding site of the muteins to the target by allosteric effects. Accordingly, any fragment, precursor or mature form of Hepcidin can be used in the generation of muteins of the invention.

A further embodiment of the methods of the invention involves operably fusing a nucleic acid coding for the plurality of muteins of the invention and resulting from mutagenesis at the 3' end with a gene coding for the coat protein pill of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described here can be used for the preparation of a phagemid library encoding muteins of the invention. The inventive nucleic acid molecules coding for muteins of the invention can be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation," can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertion/deletion (RID) mutagenesis as described by Murakami et al. (2002) *Nat. Biotechnol.* 20, 76-81 or nonhomologous random recombination (NRR) as described by Bittker et al. (2002) *Nat. Biotechnol.* 20, 1024-1029. If desired, affinity maturation can also be carried out according to the procedure described in WO 00/75308 or Schlehuber et al. (2000) *J. Mol. Biol.* 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at at least one of any of the sequence positions that correspond to sequence positions 14, 21, 60, 84, 88, 116, 141, 145, 143, 146 or 158 of the wild type sequence of human Lipocalin 2 and coupling a moiety that is able to modify the serum half time of said mutein via the thiol group of a Cys residue introduced at at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

Where a protein of the invention is a human Lipocalin 2 mutein of the invention, the naturally occurring disulfide bond between Cys 76 and Cys 175 may be removed. Accordingly, such muteins (or any other human Lipocalin 2 mutein that does not include an intramolecular disulfide bond) can be produced in a cell compartment having a reducing redox milieu, for example, in the cytoplasma of Gram-negative bacteria.

In case a lipocalin mutein of the invention includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. (1997) *Chemical Approaches to the Synthesis of Peptides and Proteins*. CRC Press, Boca Raton, Fields, GB, and Colowick (1997) *Solid-Phase Peptide Synthesis*. Academic Press, San Diego, or Bruckdorfer et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition that includes at least one inventive mutein referred to in the claims or a fusion protein or conjugates thereof and, optionally, a pharmaceutically acceptable excipient.

The lipocalin muteins according to the invention can be administered via any parenteral or non-parenteral (e.g. enteral) route that is therapeutically effective for proteinaceous drugs.

Accordingly, the muteins of the present invention can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used.

A protein of the invention of the invention may also be used to target a compound to a pre-selected site. In one such embodiment, a protein of the invention is used for the targeting of a pharmaceutically active compound to a pre-selected site in an organism or tissue, comprising:

a) conjugating the protein with said compound, and b) delivering the protein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment with binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

In a further aspect, the present invention also encompasses the use of a mutein according to the invention for the manufacture of a pharmaceutical composition. The pharmaceutical composition thus obtained may be suited for reducing the level of a Hepcidin. The pharmaceutical composition may be used as monotherapy or as combination therapy. Accordingly, the invention also relates to a mutein as defined above for the treatment of a disease or disorder associated with an altered, e.g. increased or reduced, level of a Hepcidin.

Diseases Associated with Hepcidin

Anemia is a disease associated with serum iron depletion leading to a decrease of hematological parameters such as red blood cell (RBC) counts, hematocrit (Ht), hemoglobin (Hb), serum iron level and transferrin (Tf) saturation. This results in a decreased oxygen level in the blood and is associated with a declined quality of life (QOL) described by weakness, poor concentration, shortness of breath and dyspnea. Severe anemia can lead to a fast heart rate, cardiac enlargement and heart failure. Anemia is often associated with chronic kidney disease/established chronic kidney disease (CKD), anemia of cancer (AC), chemotherapy induced anemia (CIA) and anemia of chronic disease (ACD).

The effective management of anemia has a major impact on quality of life and may influence the survival of patients. The declined quality of life can be described by weakness, fatigue, poor concentration, shortness of breath up to dyspnea. Severe anemia is associated with a fast heart rate, and can lead to cardiac enlargements and heart failure.

The standard treatment of care are transfusions and the administration of ESAs and iron. Nevertheless, new therapeutic approaches are desired since the standard treatments are associated with the following disadvantages or potential draw backs. Transfusion bears the risk of hemolysis, infections and allergic reactions due to an incompatible blood type. Iron treatment can lead to iron overload in long term treatments and is not recommended for the treatment of anemia of inflammation since iron contributes to inflammatory responses (e.g. inflammatory joint disease). As far as ESAs are concerned, about 40-50% of anemic patients are ESA non-responder with no or delayed Hb-response only after high dose ESA-treatment that are associated with safety concerns like poorer survival and shorter progression free survival time in cancer patients.

Iron deficiency anemia is a disorder of iron homeostasis that is easily cured by iron administration in contrast to anemia associated with inflammatory disease. Hepcidin is a parameter that allows distinguishing between these two disorders since the hepcidin level is only upregulated in combination with inflammation.

Anemias associated with chronic inflammatory disease like chronic infections, rheumatologic and systemic autoimmune disorders and inflammatory bowel disease are called anemia of inflammation (AI) or anemia of chronic disease (ACD). Hepcidin expression is induced by the inflammatory cytokine IL-6, as part of the inflammatory response, resulting in iron deficiency induced anemia and a blunted response to ESAs.

Patients with established chronic kidney disease (chronic renal failure (CRF)) develop uremic anemia as one of the most obvious signs of the disease. This symptom is caused by impeded renal production of erythropoietin (EPO). EPO controls red blood cell (RBC) production by promoting survival, proliferation and differentiation of erythroid progenitors in the bone marrow. Effective management of anemia in chronic renal failure (CRF) has a major impact on quality of life and may influence survival. Supplementation with recombinant human erythropoietin (rhEPO) is currently the standard treatment for anemia in those patients. A response rate of 70-90% to various ESA's (erythropoesis stimulating agents) has been observed in clinical trials with CRF patients. Only in patients with additional inflammatory disease hepcidin plays a prominent role in the anemia associated with CKD.

Anemia is common in patients with cancer and has a multifactorial aetiology. It may be related to the malignancy itself and its extent, as well as to the type, duration and intensity of myelosuppressive chemotherapy. Moreover, most patients with cancer have been shown to have inappropriately low levels of circulating EPO for their degree of anemia, reflecting a change in this homeostatic mechanism. The incidence of anemia severe enough to result in blood transfusions may be as high as 60% in certain tumor types. Anemic patients with cancer may experience symptoms as fatigue, dizziness, shortness of breath, and cardiovascular symptoms such as palpitations and cardiac failure. Such clinical sequelae may decrease the quality of life of these patients. Furthermore, a potential relationship between the correction of anemia and increased survival in patients receiving chemotherapy has recently been discussed. Currently, therapeutic options for anemia in cancer patients are RBC transfusions or ESA's. Transfusion of RBCs can be associated with non-hemolytic and hemolytic transfusion reactions, iron overload in heavily transfused patients, or the transmission of infections. Safety and screening requirements in transfusion therapy have increased the logistics and cost of transfusion therapy thus restricting transfusions to cases of severe and/or symptomatic anemia. ESA's have provided an alternative to blood transfusions in the treatment of symptomatic anemia which is still not severe enough to merit transfusions with current policies. However, a clear dose response relationship for ESA's has not been established, and 40% to 50% of patients show no Hb response at all or a delayed response. During the last years important concerns have emerged regarding the impact of ESAs on cancer patients' survival as well as their potential to increase the risk of thromboembolism (in march 2007 the FDA instituted a black-box warning about the possible association of ESAs with tumor promotion and thromboembolic events). There is raising evidence from the literature that ESA-resistance of cancer patients is not only predicted by a missing increase in Hb-response within 4 weeks of ESA administration but also by an elevated hepcidin level—presumably as part of an inflammatory response.

As explained above, Hepcidin is the central negative regulator of iron homeostasis. Hepcidin production increases with iron loading and inflammation and decreases under low iron conditions and hypoxia. Hepcidin acts via binding to the only known mammalian cellular iron exporter, ferroportin, and induces its internalization and degradation. Since ferroportin is expressed in the duodenal enterocytes, spleen, and liver, hepcidin increase, and the subsequent decrease of ferroportin, results in the inhibition of duodenal iron absorption, release of recycled iron from macrophages, and mobilization of iron stores in the liver. Hepcidin is thought to play a critical role in the development of anemia associated with inflammatory disease. Acute or chronic inflammatory conditions result in the up-regulation of hepcidin expression, leading to iron deficiency, which can cause anemia associated with inflammatory disease (ACD), cancer (AC, CIA) and Chronic Kidney Disease (CKD) (anemia of CKD).

A lipocalin mutein according to the invention may be used as an antagonist of a hepcidin (supra). In this regard a lipocalin mutein according to the invention, typically an isolated lipocalin mutein, may be used in therapy, such as human therapy. A respective mutein is capable of forming a complex with a hepcidin, e.g. a human hepcidin, typically with high affinity. Thereby the lipocalin mutein typically blocks the interaction with the hepcidin receptor ferroportin. As a result internalization and degradation of ferroportin are prevented. The lipocalin mutein thereby supports erythropoiesis by allowing mobilization of stored iron and improved enteral iron absorption. An illustrative example of a subject in need of application of a respective antagonist of a hepcidin according to the invention is a subject hyporesponsive to ESA-therapy (about 40-50% of patients) which is thought to be caused by the decreased availability of iron for the synthesis of hemoglobin due to upregulated hepcidin. The term "subject" refers to a vertebrate animal, including a mammal, and in particular a human, in which case the term "patient" can also be used. In some embodiments, the subject may have a disorder that would benefit from a decreased level of a hepcidin such as hepcidin-25, a decrease in bioactivity of a hepcidin (e.g. hepcidin-25 bioactivity), and/or an increase in serum iron level, reticulocyte count, red blood cell count, hemoglobin, and/or hematocrit.

A lipocalin mutein according to the invention may be used to increase iron levels in a body fluid such as serum. It may also be used to increase reticulocyte count, red blood cell count, hemoglobin, and/or hematocrit in a subject, e.g. a human. A pharmaceutical composition comprising a lipocalin mutein of the invention may be used in this regard.

Another aspect of the present invention relates to a method of treating a subject suffering from a disease or disorder that is associated with an altered level of a Hepcidin, such as an increased or a decreased level of a Hepcidin. A respective disease or disorder may include a genetic or a non-genetic disease/disorder causing iron deficiency or overload. A disease state or disorder may include an infectious disease involving e.g. bacteria, fungi, yeast or viruses. As explained above, in some embodiments the disease or disorder is anemia, including, but not limited to, anemia resulting from infection, inflammation, chronic disease, and/or cancer. It may in some embodiments include an inflammatory disease such as arthritis and certain cancer types, a liver disease or a haematological disease. In some embodiments of the disease associated with an incerased level of a Hepcidin is an anemia or a chronic kidney disease or an anemia associated with chronic kidney disease. As already explained above, such a method involves administering a respective mutein of the invention or a pharmaceutical composition comprising a mutein of the invention to a subject in need thereof.

A lipocalin mutein of the invention may for instance be used to treat a subject having an elevated level of hepcidin, a hepcidin-related disorder, a disorder of iron homeostasis, anemia or inflammatory condition associated with an elevated level of hepcidin. The subject may, for example, be a mammal such as a human suffering from African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (in particular anemia associated with chronic kidney disease), including end stage renal disease or chronic renal/kidney failure, cirrhosis of liver, classic hemochromatosis, collagen-induced arthritis (CIA), a condition involving hepcidin excess (elevated hepcidin), congenital dyserythropoietic anemia, congestive heart failure, Crohn's disease, diabetes, a disorder of iron biodistribution, a disorder of iron homeostasis, a disorder of iron metabolism, ferroportin disease, ferroportin mutation hemochromatosis, folate deficiency, Friedrich's ataxia, funicular myelosis, gracile syndrome, a bacterial infection such as *H. pyelori* infection, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, a viral infection such as HIV, Huntington's disease, hyperferritinemia, hypochromic microcytic anemia, hypoferremia, insulin resistance, iron deficiency anemia, an iron deficiency disorder, an iron overload disorder, an iron-deficiency condition with hepcidin excess, juvenile hemochromatosis (HFE2), multiple sclerosis, a mutation of a gene involved in iron metabolism, for instance expressing a protein involved therein such as transferrin receptor 2, HFE, hemojuvelin or ferroportin, neonatal hemochromatosis, a neurodegenerative disease related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, a red blood cell disorder, rheumatoid arthritis, sepsis, sideroblastic anemia, systemic lupus erythematosus, thalassemia, thalassemia intermedia, transfusional iron overload, a tumor, vasculitis, vitamin B6 deficiency, vitamin B12 deficiency Wilson's disease, or inflammatory condition associated with an elevated level of hepcidin.

As a further illustrative example a mutein according to the present invention can in some embodiments be used in combination with erythropoietin. Anemia in patients with cancer (AC) and anemia of chronic disease (ACD) are associated with high concentrations of hepcidin (about 30 nmol/L) leading to serum iron deficiency and thus to reduced erythropoiesis. Subjects with baseline hepcidin concentrations below 13 nmol/L in serum have been reported to show a better response to erythropoietin (EPO) therapy than subjects with concentrations above 13 nmol/L. Therefore the treatment of anemic cancer patients with a hepcidin antagonist can improve their response to erythropoietin.

Furthermore a widespread phenomenon among anemic subjects is resistance to recombinant erythropoietin (rhEPO), a therapeutic problem that can be overcome by combinatorial therapy with a mutein according to the present invention. Hepcidin likely plays a major role in this rhEPO resistance. Sasu et al. (Blood (2010) 115, 17, 3616-3624) have shown a distinct correlation between increased hepcidin level and resistance to erythropoiesis-stimulating agents (ESAs) in mice. They also were able to restore ESA-responsiveness by the administration of a hepcidin-specific antibody.

In yet another aspect the invention relates to the use of a mutein according to the invention in diagnosis. The use of a mutein according to the invention is typically for the diagnosis of a disease or disorder associated with an altered level of a Hepcidin as well as a respective method of diagnosis. The use may in some embodiments involve assessing the level of a hepcidin in a body fluid of a subject. For this purpose body fluid may have been taken from the respective subject. The level of the Hepcidin may be compared to a control sample, which is known to include a normal level of the Hepcidin. It may thereby be determined whether non-physiological levels of the Hepcidin are present in the subject.

Accordingly, the invention also relates to a mutein as defined above for the diagnosis of a disease or disorder associated with an altered, e.g. increased or reduced, level of a Hepcidin. In some embodiments the disease is an anemia, including, but not limited to, anemia resulting from infection, inflammation, chronic disease, and/or cancer. The disease or disorder may for instance be associated with decreased levels of a Hepcidin, such as hereditary hemochromatosis, an iron-loading anemia or Hepatitis C. The disease or disorder may also be associated with increased levels of a Hepcidin, e.g. anemia of inflammation, iron-refractory iron deficiency anemia or a chronic kidney disease. Hepatitis C for instance typically involves a hepatic iron overload, generally via hepcidin synthesis suppression. In the context of diagnosis a mutein according to the invention can be used to assess hepcidin levels in body fluid of a subject. Since anemic cancer patients with low hepcidin concentrations (<13 nmol/L) have been observed to show a better response to erythropoietin therapy than patients with high hepcidin concentrations (>13 nmol/L) hepcidin serum concentrations can for instance be used for predicting the response to epoetin therapy (about 50% of the patients are EPO resistant).

In still another aspect, the present invention features a diagnostic or analytical kit comprising a mutein according to the present invention.

The subject in need of such a treatment may be a mammal, such as a human, a dog, a mouse, a rat, a pig, an ape such as cynomolgous monkeys to name only a few illustrative examples.

In still another aspect, the present invention features a method for in vivo imaging in a subject, including administering to said subject a mutein of the invention or a pharmaceutical composition comprising a mutein of the invention. The subject may be defined as above.

The invention is further illustrated by the following non-limiting Examples and the attached drawings.

Unless otherwise indicated, established methods of recombinant gene technology were used, for example, as described in Sambrook et al. (supra).

EXAMPLE 1

Construction of a Mutant Lcn2 Phage Display Library

A combinatorial library of Lcn2 variants was generated on the basis of the cloned cDNA (Breustedt et al. (2006) *Biochim. Biophys. Acta* 1764, 161-173), which carried the amino acid substitutions Cys87Ser, to remove the single unpaired thiol side chain (Goetz et al. (2000) *Biochemistry* 39, 1935-1941), as well as Gln28His to introduce a second BstXI restriction site. Mutagenesis and polymerase chain reaction (PCR) assembly of this region was essentially performed according to a published strategy (Beste et al. (1999) *Proc. Natl. Acad. Sci. USA* 96, 1898-1903; Skerra (2001) *J. Biotechnol.* 74, 257-275), this time using a one pot amplification reaction with oligodeoxynucleotides (sequences of SEQ ID NO: 16 to SEQ ID NO: 25) as illustrated in FIG. 1. Oligodeoxynucleotides were designed such that the primers with sequences of SEQ ID NO: 16 to SEQ ID NO: 19 corresponded to the coding strand and carried degenerate codons at the amino acid positions 36, 40, 41, 49, 52, or 68, 70, 72, 73, 77, 79, 81, or 96, 100, 103, 106, or 125, 127, 132, 134 respectively, while primers with sequences of SEQ ID NO: 20 to SEQ ID NO: 23 corresponded to the non-coding strand and did not carry degenerate codons or anticodons. The two flanking primers with SEQ ID NO: 24 and SEQ ID NO: 25 were used in excess and served for the amplification of the assembled randomized gene fragment. All PCR steps were performed using Go-Taq Hot Start DNA polymerase (Promega, Mannheim, Germany) as described (Schlehuber et al. (2000) *J. Mol. Biol.* 297, 1105-1120).

Oligodeoxynucleotides that did not carry degenerate codons were purchased in HPLC grade from Metabion (Munich, Germany). NNK-containing oligodeoxynucleotides were purchased desalted from the same vendor and further purified by urea PAGE. The resulting DNA library was cut with BstXI (Promega, Mannheim, Germany) and cloned on the phagemid vector phNGAL102 (SEQ ID NO: 26), which is based on the generic expression vector pASK111 (Vogt and Skerra (2001) *J. Mol. Recognit.* 14 (1), 79-86) and codes for a fusion protein composed of the OmpA signal peptide, the modified mature Lcn2, followed by an amber codon, and the C-terminal fragment of the gene III coat protein of the filamentous bacteriophage M13, i.e. similar as previously described for the bilin-binding protein (Beste et al., supra; Skerra, supra). After electroporation of *E. coli* XL1-Blue (Bullock et al. (1987) *Biotechniques* 5, 376-378) with the ligation mixture of 8.4 μg digested PCR product and 94 μg digested plasmid DNA, $1\times10^{10}$ transformants were obtained.

Alternatively, a cloned synthetic Lcn2 random library, which is described in FIG. 2, was obtained from Sloning BioTechnology GmbH (Puchheim, Germany). The central gene cassette flanked by the two BstXI restriction sites was amplified via PCR in 20 cycles using appropriate primers (SEQ ID NO: 24 and SEQ ID NO: 25) and subcloned on phNGAL108 (SEQ ID NO: 27), which is based on the generic expression vector pASK75 (Skerra (1994) *Gene* 151, 131-135) and carries essentially the same features as phNGAL102 (SEQ ID NO: 26) but mediates ampicillin resistance instead of chloramphenicol resistance, in the same way, yielding a library with a complexity corresponding to $1.7\times10^{10}$ independent transformants.

The following steps in library generation were performed identically for both Lcn2 libraries. 100 ml of the culture, containing the cells which were transformed with the phasmid vectors on the basis of phNGAL102 or phNGAL108, respectively, coding for the library of the lipocalin muteins as phage pIII fusion proteins, were transferred to a sterile Erlenmeyer flask and incubated for one hour at 37° C., 160 rpm in 2YT medium without antibiotic selection pressure. Before infection with VCS-M13 helper phage the culture was diluted in 2YT medium to an OD550 of 0.1 with the corresponding antibiotic added and further grown under identical conditions until an OD550 of 0.6 was reached. After infection with VCS-M13 helper phage (Agilent Technologies, La Jolla, USA) at a multiplicity of infection of approximately 10 the culture was shaken for additional 30 min at 37° C., 100 rpm. Then the incubator temperature was lowered to 26° C. and the shaker speed was increased again to 160 rpm, after 10 min kanamycin (70 μg/ml) was added, followed by induction of gene expression via addition of anhydrotetracycline (ACROS Organics, Geel, Belgium) at 25 μg/l (125 μl of a 200 μg/ml stock solution in dimethylformamide, DMF per liter of culture). Incubation continued for another 12-15 h at 26° C., 160 rpm.

Cells from the complete culture were sedimented by centrifugation (30 min, 18000 g, 4° C.). The supernatant containing the phagemid particles was sterile-filtered (0.45 μm), mixed with 1/4 volume 20% w/v PEG 8000, 15% w/v NaCl, and incubated on ice for at least 2 h. After centrifugation (30 min, 18000 g, 4° C.) the precipitated phagemid particles from 1 liter of culture were dissolved in 30 ml of cold BBS/E (200 mM Na-borate, 160 mM NaCl, 1 mM EDTA pH 8.0) containing 50 mM benzamidine (Sigma) and Pefabloc 1 μg/ml (Roth, Karlsruhe, Germany). The solution was incubated on ice for 1 h. After centrifugation of undissolved components (10 min, 43000 g, 4° C.) each supernatant was transferred to a new reaction vessel.

Addition of 1/4 volume 20% w/v PEG 8000, 15% w/v NaCl and incubation for 60 min on ice served to reprecipitate the phagemid particles until the phagemids were aliquoted and frozen at −80° C. for storage. For the first selection cycle phagemids were thawed and centrifuged (30 min, 34000 g, 4° C.), the supernatant was removed, and the precipitated phagemid particles were dissolved and combined in a total of 400 μl PBS containing 50 mM benzamidine. After incubation for 30 min on ice the solution was centrifuged (5 min, 18500 g, 4° C.) in order to remove residual aggregates and the supernatant was used directly for the phage display selection.

EXAMPLE 2

Procurement of Soluble Hepcidin 25 Peptides

Synthetic non-modified Hepcidin-25 (human DTHFPICIFCCGCCHRSKCGMCCKT, SEQ ID NO: 28, 2789.4 g/mol; mouse DTNFPICIFCCKCCNNSQCGICCKT, SEQ ID NO: 29, 2754.2 g/mol; rat DTNFPICLFCCKCCKNSSCGLCCIT, SEQ ID NO: 30, 2711.9 g/mol) and the C-terminal biotinylated rat Hepcidin-25 (DTNFPICLFCCKCCKNSSCGLCCIT (SEQ ID NO: 30)-Mini-PEG-linker-K-Biotin, 3210.5 g/mol) was obtained from PeptaNova GmbH (Sandhausen, GE).

The human and mouse C-terminal biotinylated Hepcidin-25 was obtained from Bachem AG (Bubendorf, CH). Analogous to the rat Hepcidin-25 these targets were biotinylated via a Lysine residue coupled to the C-terminus via a Mini-PEG linker.

EXAMPLE 3

Generation of a Library with 10 Billion Independent NGAL Muteins

A random library of NGAL lipocalin (Lcn2) with high complexity was prepared essentially as described in Example 1 above. The amplification reaction is illustrated in FIG. 1, the phagemid vector phNGAL102 is of SEQ ID NO: 26.

EXAMPLE 4

Phagemid Presentation and Selection of NGAL Muteins with Affinity for Human Hepcidin Phagemid display and selection was performed employing the phagemids obtained from Example 1 essentially as described in international patent application WO/2005/019256. The library was subjected to 3 cycles of phage display selection against the soluble, C-terminal biotinylated human Hepcidin-25 target peptide.

$2\times10^{12}$ to $1\times10^{13}$ phagemids of the library obtained in Example 1 were used. In brief, the phagemids were centrifuged (21460×g, 4° C., 20 min) and resuspended in 1 ml PBS (4 mM $KH_2PO_4$, 16 mM $Na_2BPO_4$, 115 mM NaCl, pH 7.4)

containing 50 mM benzamidine. PBS containing 1% w/v Casein (Sigma) and 0.1% Tween 20® was used as blocking buffer. Prior to the incubation with the target protein, phagemids from the library were incubated with casein-blocked Streptavidin beads for 30 minutes for the depletion of phagemids representing multi-reactive or misfolded lipocalin mutein or Streptavidin bead-specific muteins.

In different Panning approaches a 1 μM solution of target was either captured on Streptavidin™-coated, 1% Casein-blocked magnetic beads prior to the incubation with phagemids (solid in solution approach) or 500 nM Hepcidin-25 was incubated in solution with 3·1012 phagemids from the NGAL library blocked with 1% Casein (solution approach). In the solution approach peptide bound phagemids were captured via Streptavidin™-coated magnetic beads (Invitrogen/Dynal) within 20 min, followed by 8 wash cycles and elution with either 300 μL 70 mM Triethylamin for 10 min, and neutralization with an appropriate amount of 1 M Tris/HCl, pH 7.4 (basic elution) or with 300 μL 0.1 M Glycin/HCl pH 2.2 for 10 min. and neutralization with an appropriate amount of 0.5 M Tris-Base (acidic elution).

In the solid in solution approach blocked phagemids were incubated with the Streptavidin bead-coated target followed by 8 wash cycles and elution as described above [0199]. Beginning with the second enrichment cycle, only half of the combined phagemid solutions were used for phagemid amplification.

Phagemid amplification between each panning cycle was performed as described in Schlehuber, S. et al. (*J. Mol. Biol.* (2000), 297, 1105-1120).

Two further selection rounds against Hepcidin-25 were carried out in this way employing the preparation of amplified phagemids from the respective previous enrichment cycle with the exception that only about 1×10 phagemids were utilized beginning with the second enrichment cycle.

EXAMPLE 5

Identification of hHepcidin-Specific Muteins Using High-Throughput ELISA Screening Screening of the muteins selected according to Example 4 was performed essentially as described in Example 3 of international patent application WO 2006/56464.

Lipocalin muteins were selected in a HT-screening ELISA. Therein, NGAL variants equipped with a T7 detection tag (Novagen) as well as a Strep-tag II affinity tag (IBA) were soluble expressed in a 96 well microtiter plate using the *E. coli* strain TG1/ $F^-$ with phNGAL 101. This vector corresponds to phNGAL 98 (SEQ ID NO: 31) with an N-terminal T7 tag consisting of 11 amino acids (MASMTGGQQMG) (residues 187-197 of SEQ ID NO: 34, see also FIG. 4B). Lipocalin mutein expression was induced onvernight at 22° C. at 700 rpm with anhydrotetracycline (0,2μg/ml) at an $OD_{550}$ of 0.6. Afterwards, cells were lysed (100 mM Na-borate, pH 8.0, 80 mM NaCl, 1 mM EDTA, 0.025% w/v lysozyme) for 1 h under agitation. To minimize non-specific binding in the subsequent ELISA screen, the crude cell lysates were supplemented with 2% w/v BSA and 0.1% v/v Tween 20 and tested in ELISA for binding to human Hepcidin-25. Therefore, soluble C-terminal biotinylated human Hepcidin-25 was immobilized on wells of black Fluotrac 600 ELISA plates (Greiner; 384 well) with 1 μg/ml via capturing by Neutravidin (5μg/ml, Thermo Scientific). Neutravidin, Streptavidin, 5 μg/ml each, and 3% milk were used as negative control. Plates were blocked with PBST/0.1 containing 2% w/v BSA , and subsequently incubated with the bacterial cell extract for 1 h at room temperature plates were washed five times and bound Lipocalin muteins were detected via an anti-T7 monoclonal antibody-HRP conjugate (Novagen), diluted 1:10.000 in PBST/0.1. Therefore, QuantaBlu™ (Pierce; 1:2 diluted in PBS/T 0.1%) was used as fluorogenic HRP substrate. After 45 min of signal development at room temperature fluorescence was excited at a wavelength of 320 nm (±12.5 nm) and measured at 430 nm (±17.5 nm) in a GENiosPlus plate reader (Tecan).

In a reverse ELISA approach soluble expressed muteins from the crude cell lysate were captured in ELISA plates via their T7-tag following incubation with varying amounts of C-terminal biotinylated hHepcidin to reach target-limiting conditions in order to differentiate the muteins by their affinity. Binding of the target was detected via Extravidin-HRP conjugate (Sigma). One could compete for mutein binding by the addition of 100 nM non-biotinylated human Hepcidin-25 indicating, that the muteins bind the non-modified hHepcidin-25 as well.

Screening of 2160 clones, selected as described in Example 4, led to the identification of more then 1000 primary hits indicating the successful isolation of target-specific muteins. The reverse ELISA approach under target-limiting conditions and the competition ELISA allowed for a differentiation of hepcidin-specific muteins in terms of their target affinity. Using these ELISA approaches the clones with SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 8, SEQ ID NO: 9, SEQ ID NO: 10, SEQ ID NO: 11, and SEQ ID NO: 12 were identified. The sequences of these muteins are depicted in FIG. 3.

EXAMPLE 6

Production of Hepcidin-Binding Muteins (NGAL)

The recombinant Lcn2 and the hHepcidin-specific Lcn2 variants were produced by periplasmic secretion in *E. coli* K12 strain JM83 (Yanisch-Perron et al. (1985) Gene 33, 103-119), the *E. coli* supE strain TG1-F— (a derivative of *E. coli* K12 TG1 [Kim et al. (2009) J. Am. Chem. Soc. 131, 3565-3576] that was cured from its episome using acridinium orange), *E. coli* BL21 (Studier and Moffat (1986) J. Mol. Biol. 189, 113-130), or *E. coli* W3110 (Bachmann (1990) Microbiol. Rev. 54, 130-197).

For a small scale soluble protein expression the plasmid phNGAL98 (SEQ ID NO: 31) was used, encoding a fusion of the OmpA signal peptide with the respective mutein and the C-terminal Strep-tag II, whereby the plasmid carries the two non-compatible BstXI restriction sites for unidirectional subcloning of the mutated gene cassette. Growth was allowed to occur in a 2 L shaking flask culture in the presence of LB-Ampicillin medium according to the protocol described in Schlehuber, S. et al. (*J. Mol. Biol.* (2000), 297, 1105-1120). For larger amounts of protein the periplasmatic production was performed with the same vector expressed in the *E. coli* strain W3110 via bench top fermenter cultivation in a 1 l or 10 l vessel based on the protocol described in Schiweck, W., and Skerra, A. *Proteins* (1995) 23, 561-565).

In order to increase the in vivo half-life, selected lipocalin muteins were exemplarily modified by the following procedures.

An ABD-fusion protein was constructed and periplasmatically expressed for the mutein of SEQ ID NO: 1. The albumin binding domain from the streptococcal protein G was fused to the C-terminus of the mutein via the original linker derived from streptococcal protein G as described in SEQ ID NO: 15.

In the case of site-directed PEGylation the hNGAL muteins having a free cystein residue at amino acid position 87 (SEQ ID NO: 13, SEQ ID NO: 14) were used for PEGylation with branched 40k PEG-maleimide. To this aim, the Serine at position 87 was back-mutated to a Cysteine that originally occurs in hNGAL wildtype by site-directed mutagenesis (Quick-change mutagenesis Kit, Stratagene). Prior to the PEGylation reaction the free cysteine residue was reduced in a 1:1 molar ratio of Anticalin with TCEP for 3 h at RT. Thereafter, PEGylation was performed by mixing the protein with >2 molar excess of PEG40-maleimide reagent for 1.5 h at RT.

The Lcn2 variants were purified from the periplasmic fraction in a single step via streptavidin affinity chromatography (Strep-Tactin™ Superflow, IBA) using a column of appropriate bed volume according to the procedure described by Skerra, A. & Schmidt, T. G. M. (2000) (Use of the Strep-tag and streptavidin for detection and purification of recombinant proteins. *Methods Enzymol.* 326A, 271-304). To achieve higher purity and to remove any aggregated recombinant protein, a gel filtration of the muteins was finally carried out on a Superdex 75 HR 10/30 column (24-ml bed volume, Amersham Pharmacia Biotech, Freiburg, Germany) in the presence of PBS buffer. The monomeric protein fractions were pooled, analysed for purity by SDS-PAGE (Fling and Gregerson (1986) *Anal. Biochem.* 155, 83-88), and used for further biochemical characterization.

The pegylated versions of hNGAL muteins were purified by chromatography and, where necessary, a further reduction of bacterial endotoxins was achieved by MustangE membrane (Pall Corporation, US) filtration.

EXAMPLE 7

Affinity Measurement Using ELISA Techniques

A “direct” ELISA was performed to verify the binding affinity and specificity of the selected Lcn2 muteins. Therefore, a constant concentration of 1 μg/ml C-terminal biotinylated hepcidin (Bachem AG, CH) was captured on the surface of a polystyrol plate (Greiner, GE) via Neutravidin (Thermo Scientific, 5 μg/ml). Two step dilution series of purified Lcn2 muteins were incubated with the captured hepcidin for 1 h at room temperature and detected either via the Strep-tag II using a rabbit anti-strep-tag II polyconal antibody (GenScript, USA) or by using a scaffold-specific polyclonal rabbit antibody. In both cases an anti rabbit IgG-HRP conjugate (Abcam, UK) was employed as secondary detection antibody.

The absorption ΔA at 320 nm was measured in an ELISA reader (Tecan, GE) and the data were fitted with Graphpad Prism software (Statcom, USA).

Results from measurements employing the muteins of the sequences of SEQ ID NO: 1 to SEQ ID NO: 12, as well as of SEQ ID NO: 14, linked to PEG40, of SEQ ID NO: 13, linked to PEG40 and of SEQ ID NO: 1, linked to albumine-binding domain (ABD) (SEQ ID NO: 15) are summarized in FIG. 5.

$K_D$ values of the selected Lcn2 muteins vary from 220 pM up to 6.8 nM. All muteins bound human and cynomolgus hepcidin-25 with comparable affinity. Serum half-life extension of the lipocalin mutein of SEQ ID NO: 1 via C-terminal fusion of the albumine-binding domain had no significant effect on the binding affinity of the mutein whereas pegylation reduced the binding affinities in this ELISA format significantly by a factor of 5 for SEQ ID NO: 8 and a factor of 8 for the mutein of SEQ ID NO: 1.

The binding affinity of the Lcn2 muteins to non-modified hepcidin-25 in solution was evaluated in a competition ELISA approach. Therefore, a constant concentration of 1 μg/ml C-terminal biotinylated human hepcidin (Bachem AG, CH) was captured on the surface of a polystyrol plate (Greiner, GE) via Neutravidin (Thermo Scientific, 5 μg/ml, GE). In parallel a two step dilution series of non-biotinylated human hepcidin starting from 1 μM was incubated with a constant concentration of hepcidin-specific mutein for 1 h at room temperature in a non-protein binding 96 well polypropylene plate (Nunc, GE). The constant concentration of lipocalin muteins corresponds to the $EC_{50}$ of the respective muteins as determined in a direct ELISA as described above in this example. In the following the mixture of non-modified human hepcidin and lipocalin mutein was transferred onto the hepcidin-captured Neutravidin plate. The C-terminal biotinylated hepcidin was allowed to compete with the non-modified hepcidin for Anticalin binding for 20 min. at room temperature. During these 20 min, free lipcocalin mutein was bound to the captured hepcidin and detected via a rabbit anti-strep-tag II polyconal antibody (GenScript, USA). A goat anti-rabbit IgG-HRP conjugate (Abcam, UK) was employed as secondary detection antibody. Parallel to the competition assay, anticalin binding was determined on the same plate in a “direct” ELISA, in order to obtain a standard curve linking the RFU values to anticalin concentration. This curve was then used to standardize competition data to the level of anticalins bounds to the plate and fitted with Graphpad software. $IC_{50}$ values correspond to the half-maximum amount of lipocalin mutein bound to the plate.

Results from measurements employing the muteins of the sequences of SEQ ID NO: 1 to SEQ ID NO: 12, as well as of SEQ ID NO: 14, linked to PEG40, of SEQ ID NO: 13, linked to PEG40 and of SEQ ID NO: 1, linked to ABD (SEQ ID NO: 15), are summarized in FIG. 6.

$IC_{50}$ values of the selected Lcn2 muteins vary from 100 pM up to 10.8 nM. Serum half-life extension via the albumine-binding domain had no effect on the binding affinity of the mutein of SEQ ID NO: 1, whereas pegylation reduced the binding affinities by a factor of 2 for SEQ ID NO: 13-PEG40 and by a factor of 4 for SEQ ID NO: 14-PEG40, respectively.

EXAMPLE 8

Affinity Measurement Using Surface-Plasmon-Resonance (SPR)

Surface plasmon resonance was used to measure binding kinetics and affinity of the lipocalin muteins disclosed herein.

Lipocalin muteins were immobilized to a CM5 sensor chip using standard amine chemistry: The surface of the chip was activated using EDC and NHS. Subsequently, 20 μg/mL lipocalin mutein solutions in 10 mM sodium acetate pH 4.5 (60 μg/mL in 10 mM sodium acetate pH 4.0 for peglyted lipocalin mutein) were applied at a flow rate of 5 μL/min until a surface density of 500-700 resonance units (RU) for non-modified lipocalin muteins and of approximately 1600 RU for pegylated lipocalin with the sequence of SEQ ID NO: 13 was achieved. Residual activated groups were saturated with ethanolamine. The reference channels were treated with EDC/NHS following ethanolamine (blank immobilization). All reagents and materials were purchased from GE Healthcare.

Serial dilutions of human and cynomolgus Hepcidin-25 in running buffer (HBS-EP+, GE Healthcare, BR-1006-68) were applied to the prepared surface. The following parameters were used for the binding assay: contact time 60 s, dissociation time 180-360 s, flow rate 30 μL/min. All measurements were performed on a Biacore T100 instrument (GE Healthcare) at 25° C. Regeneration of the surfaces having lipocalins immobilized thereon were achieved with subsequent injections of 2 M/4 M Guanidinium-HCl (120-600 s) and 10 mM glycine-HCl pH 1.5/2.0 (40-240 s) followed by an extra wash with running buffer and a stabilization period of 120 s.

Data were evaluated with Biacore T100 Evaluation software (V 2.0.1). Double referencing was used. The 1:1 Binding model (Langmuir) was used to fit the raw data.

Duplicates were reproducible and no binding to the reference channel was detected. The binding parameters of the lipocalin muteins with the sequences of SEQ ID NO: 1, SEQ ID NO: 8 as well as of SEQ ID NO: 13, linked to PEG40, to human and cynomolgus Hepcidin-25 are summarized in FIG. 7.

Cynomolgus Hepcidin-25 was binding to immobilized lipocalin muteins with an approximately 2-fold higher affinity compared to the human target. Kinetic analysis of hHepcidin-25 on the immobilized pegylated variant having the sequence of SEQ ID NO: 13 revealed a high affinity of 40 pM.

EXAMPLE 9

Cell-Based Assay for Hepcidin-Induced Internalization and Degradation of Ferroportin An in vitro cell-based assay was used to measure the neutralization activity of the lipocalin muteins of the present invention that are directed against human hepcidin. The assay is based on hepcidin-induced internalisation and degradation of its receptor, ferroportin and was implemented basically as described (Nemeth et al. 2004, 2006).

Briefly, a HEK-293 stable cell line was prepared that allowed for the inducible expression of murine ferroportin (FPN) carboxy-terminally fused with green fluorescent protein (GFP). The inducible expression of the FPN-GFP fusion protein was controlled by Doxycyclin using the commercially available tetracycline-regulated T-REx expression system (Invitrogen, Karlsruhe, Germany). The FPN-GFP coding sequence was cloned into pcDNA 4/TO vector, which contains an inducible promoter and a Zeocin resistance marker. The resulting construct was stably transfected into T-REx-293 cells which express the regulatory protein required for doxycycline-inducible expression.

The assay for hepcidin-induced internalisation of the hepcidin receptor was performed as follows: Cells of the T-REx-293::FPN-GFP stable line were seeded in T75 cell culture flasks at 80% confluence. In the evening FPN-GFP expression was induced with 4 ng/ml Doxycyclin and stabilized with 10 μM Ammonium iron (III) citrate for 16 h at 37° C. On the next morning cells were trypsinized and seeded in a 24-well plate at 0.3 million cells/well in a volume of 450 μl. Cells were allowed to attach for 1 h at 37° C. prior to the addition of hepcidin. Cells were incubated at 37° C. for 24 h and GFP fluorescence of the detached cell suspension was analyzed by flow cytometry.

The EC80 (40 nM) of hepcidin-mediated degradation of the Fpn-GFP fusion protein was used in neutralization assays. For this purpose Anticalins were incubated with hepcidin at room temperature for 30 min prior to addition to the cells. Following the 24 h incubation period fluorescence was quantified as described above.

The anti-hepcidin lipocalin muteins having the sequences of SEQ ID NO: 1, SEQ ID NO: 2, SEQ ID NO: 4, SEQ ID NO: 6, SEQ ID NO: 7, SEQ ID NO: 8, SEQ ID NO: 10, SEQ ID NO: 11, as well as of SEQ ID NO: 14 linked to PEG40 and SEQ ID NO: 13 linked to PEG40 and SEQ ID NO: 1 linked to ABD (SEQ ID NO: 15) neutralized the bioactivity of human hepcidin-25 with IC50 values shown in FIG. 8.

EXAMPLE 10

Anti-Hepcidin Lipocalin Muteins Neutralize Human Hepcidin in Mice

The activity of anti-human hepcidin lipocalin muteins was evaluated in vivo in mice that were administered human hepcidin in an amount sufficient to generate a hypoferremic response as described (Nemeth et al. (2006) *Blood,* 107:328-333).

Two weeks before the experiment C57BL/6 mice were switched to an iron deficient diet to suppress endogenous hepcidin. Prior to the experiment a 3-fold molar excess of lipocalin mutein was allowed to bind synthetic human hepcidin-25 for 30 minutes. In parallel wildtype lipocalin (NGAL 98) was pre-incubated with human hepcidin-25 in the same molar ratio as an isotypic control. Mice received a single intraperitoneal (i.p.) injection of either PBS (vehicle) or 2 mg/kg hepcidin or 2 mg hepcidin/Kg pre-incubated with either lipocalin mutein or wild type lipocalin (negative control). Two hours later, blood was collected under isoflurane anesthesia and total serum iron levels were determined using a colorimetric assay on a KoneLab XTi clinical analyzer.

The results are depicted in FIG. 9 as total serum iron levels in μM concentrations. Hepcidin treatment induced a significant drop of serum iron levels in iron-starved mice. Hepcidin pre-incubated with the wildtype lipocalin also exhibited hypoferremia. The pre-complexation of human hepcidin with the lipocalin mutein protected the animals from the hypoferremic response.

EXAMPLE 11

Determination of Pharmacokinetic (PK) Parameter for Anti-Hepcidin-25 Lipocalin Muteins Pharmacokinetic (PK) parameters (half-life plasma concentration) for the Lcn 2 mutein having the sequence of SEQ ID NO: 14 linked to PEG40 and of SEQ ID NO: 1 linked to ABD (SEQ ID NO: 15) were determined following i.v. single bolus administration in NMRI mice and Cynomolgus (*Macacca fascicularis*) at doses depicted in FIG. 10. Plasma was prepared from terminal blood samples taken at pre-determined timepoints and the concentrations of the lipocalin mutein were determined by ELISA. The elimination rate constant was calculated by least squares linear regression of the terminal portion of the log transformed plasma concentration-time curve. The start of the terminal elimination phase for each individual profile was defined by visual inspection and was the first point at which there was no systematic deviation from the log-linear decline in serum concentrations. T1/2 was calculated according to the following formula:

$$t_{\frac{1}{2}} = \frac{\ln(2)}{\lambda_z}$$

T1/2 SEQ ID NO: 14-PEG (mouse): 27.9 h; T1/2 SEQ ID NO: 1-ABD (mouse): 30 h; T1/2 SEQ ID NO: 14-PEG (Cyno): 88 h.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

It must be noted that as used herein, the singular forms "a", "an", and "the", include plural references unless the context clearly indicates otherwise. Thus, for example, reference to "an antibody" includes one or more of such different antibodies and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The inventions illustratively described herein may suitably be practiced in the absence of any element or elements, limitation or limitations, not specifically disclosed herein. Thus, for example, the terms "comprising," "including," containing," etc. shall be read expansively and without limitation. In each instance herein any of the terms "comprising", "consisting essentially of" and "consisting of" may be replaced with either of the other two terms.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A lipocalin mutein that is capable of binding hepcidin with an affinity by a $K_D$ of about 10 nM or lower, wherein the lipocalin mutein comprises:

(i) a set of mutated amino acid residues at the sequence positions 96, 100, and/or 106 of the linear polypeptide sequence of mature human neutrophil gelatinase-associated lipocalin (hNGAL), selected from the group consisting of (a) Asn 96→Val, Tyr 100→Gln, and Tyr 106→unchanged, (b) Asn 96→Arg, Tyr 100→Glu, and Tyr 106→Phe, (c) Asn 96→Asp, Tyr 100→Ser, and Tyr 106→Gly, (d) Asn 96→Gly, Tyr 100→Gly, and Tyr 106→Gly, (e) Asn 96→Lys, Tyr 100→Ala, and Tyr 106→Ile, (f) Asn 96→Ser, Tyr 100→Arg, and Tyr 106→Val, (g) Asn 96→Ser, Tyr 100→Val, and Tyr 106→Arg, and (h) Asn 96→Thr, Tyr 100→Val, and Tyr 106→Gly; and (ii) at least 1, 2, 3, 4, 5, 6, 7, 8, 9, 10, 11, 12, 13, 14, 15, 16, or 17 mutated amino acid residues at any of the sequence positions corresponding to the sequence positions 36, 40, 41, 49, 52, 68, 70, 72, 73, 77, 79, 81, 103, 125, 127, 132, and 134 of the linear polypeptide sequence of mature hNGAL.

2. The lipocalin mutein according to claim 1, with an IC50 value of about 80 nM or lower as determined by a cell-based assay for hepcidin-induced internalization and degradation of ferroportin.

3. The lipocalin mutein according to claim 1, wherein the lipocalin mutein binds a mature human hepcidin defined by a $K_D$ of 10 nM or lower.

4. The lipocalin mutein according to claim 1, which is capable of neutralizing the bioactivity of human hepcidin-25 and/or preventing human hepcidin-25 induced reduction of serum iron levels in a human.

5. The lipocalin mutein according to claim 1, wherein the lipocalin mutein comprises a mutated amino acid residue at any one or more of the sequence positions corresponding to the sequence positions 52, 68, 81, 127 and 134 of the linear polypeptide sequence of mature hNGAL.

6. The lipocalin mutein according to claim 1, wherein the lipocalin mutein comprises within the linear polypeptide sequence of mature hNGAL one or more of the following substitutions: Leu 36→Ala, Cys, Thr or Val; Ala 40→Arg, Glu, Gly or Ser; Ile 41→Ile, Leu, Met or Val; Gln 49→Leu or Met; Tyr 52→His, Leu, Phe or Trp; Ser 68→Arg, Gly, or Ile; Leu 70→Asp, Asn, Gln, Met or Phe; Arg 72→Glu, Gly, Leu or Val; Lys73→Ala, Arg, Glu, Gly, Leu, Thr or Tyr; Asp 77→Arg, Glu, Gly, Leu, Ser or Val; Trp 79→Gly, Leu, Ser, Tyr or Val; Arg 81→Glu, Gly, or Gln; Asn 96→Arg, Asp, Gln, Gly, Lys, Ser, Thr or Val; Tyr 100→Ala, Arg, Glu, Gln, Gly, Ser or Val; Leu 103→Ala, Arg, Gly or Trp; Tyr 106→Ile, Gly, Phe, Val or Arg; Lys 125→Arg, Leu, Met, Phe, Thr, or Val; Ser 127→Thr or Trp; Tyr 132→Leu or Val; and Lys 134→Trp.

7. The lipocalin mutein according to claim 1, comprising one of the following sets of amino acid combinations:

(a) Leu 36, Glu 40, Val 41; Met 49; Trp 52, Ile 68, Met 70, Leu 72, Ala 73, Glu 77, Leu 79; Gln 81, Asp 96, Ser 100, Arg 103, Gly 106, Thr 125, Trp 127, Val 132, Trp 134;

(b) Leu 36, Glu 40, Val 41, Met 49, Trp 52, Ile 68, Met 70; Leu 72, Ala 73, Glu 77, Leu 79, Gln 81, Gly 96, Gly 100, Arg 103, Gly 106, Val 125, Trp 127, Val 132, Trp 134;

(c) Leu 36, Glu 40, Val 41, Met 49, Trp 52, Ile 68, Met 70, Leu 72, Ala 73, Glu 77, Leu 79; Gln 81, Asp 96, Ser 100, Arg 103, Gly 106, Val 125, Trp 127, Val 132, Trp 134;

(d) Leu 36, Glu 40, Ile 41, Met 49, Trp 52, Ile 68, Met 70, Leu 72, Ala 73, Glu 77; Leu 79; Gln 81, Asp 96, Ser 100, Arg 103, Gly 106, Val 125, Trp 127, Val 132, Trp 134;

(e) Leu 36, Glu 40, Ile 41, Met 49, Trp 52, Ile 68, Met 70, Leu 72, Ala 73, Glu 77, Leu 79, Gln 81, Asp 96, Ser 100, Arg 103, Gly 106, Val 125, Trp 127, Val 132, Trp 134; and (f) Leu 36, Glu 40, Val 41, Met 49, Trp 52, Ile 68, Met 70, Leu 72, Ala 73, Glu 77, Leu 79, Gln 81, Asp 96, Ser 100, Arg 103, Gly 106, Val 125, Trp 127, Val 132, Trp 134.

8. The lipocalin mutein according to claim 1, wherein the lipocalin mutein further comprises, with respect to the amino acid sequence of mature hNGAL, one or more amino acid replacements selected from the group consisting of: Gln 28→His; Lys 59→Glu; Lys 62→Arg; Phe 71→Pro or Ser; Lys 74→Glu; Lys 75→Glu; Ile 80→Phe; Cys 87→Ser; Ile 135→Val; Ser 146→Pro and Glu 147→Gly.

9. The lipocalin mutein according to claim 1, wherein the lipocalin mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

10. The lipocalin mutein according to claim 1, wherein the lipocalin mutein is fused at its N-terminus and/or its C-terminus to a fusion partner which is a protein, or a protein domain or a peptide.

11. The lipocalin mutein according to claim 1, wherein the lipocalin mutein is conjugated to a compound that extends the serum half-life of the lipocalin mutein.

12. A nucleic acid molecule comprising a nucleotide sequence encoding the lipocalin mutein according to claim 1.

13. A pharmaceutical composition comprising a lipocalin mutein according to claim 1 and a pharmaceutically acceptable excipient.

* * * * *